(12) United States Patent
Trushina et al.

(10) Patent No.: US 10,774,045 B2
(45) Date of Patent: Sep. 15, 2020

(54) COMPOUNDS FOR MODULATING MITOCHONDRIAL FUNCTION

(71) Applicant: Mayo Foundation for Medical Education and Research, Rochester, MN (US)

(72) Inventors: Eugenia Trushina, Pine Island, MN (US); Robert Greenhouse, Newark, CA (US); Kevin Greenman, Sunnyvale, CA (US); William Thomas, San Jose, CA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/433,254

(22) Filed: Jun. 6, 2019

(65) Prior Publication Data
US 2019/0352263 A1    Nov. 21, 2019

Related U.S. Application Data

(62) Division of application No. 15/554,767, filed as application No. PCT/US2016/020698 on Mar. 3, 2016, now Pat. No. 10,336,700.

(60) Provisional application No. 62/127,584, filed on Mar. 3, 2015.

(51) Int. Cl.
| | | |
|---|---|---|
| C07D 213/36 | (2006.01) | |
| C07D 235/06 | (2006.01) | |
| C07D 239/26 | (2006.01) | |
| C07D 213/74 | (2006.01) | |
| C07D 213/81 | (2006.01) | |
| C07C 217/52 | (2006.01) | |
| C07D 213/38 | (2006.01) | |
| C07D 213/40 | (2006.01) | |
| C07D 213/82 | (2006.01) | |

(52) U.S. Cl.
CPC .......... *C07D 213/36* (2013.01); *C07C 217/52* (2013.01); *C07D 213/38* (2013.01); *C07D 213/40* (2013.01); *C07D 213/74* (2013.01); *C07D 213/81* (2013.01); *C07D 213/82* (2013.01); *C07D 235/06* (2013.01); *C07D 239/26* (2013.01); *C07B 2200/07* (2013.01); *C07C 2601/14* (2017.05)

(58) Field of Classification Search
CPC ... C07D 213/36; C07D 235/06; C07D 239/26
See application file for complete search history.

(56) References Cited

U.S. PATENT DOCUMENTS

| | | |
|---|---|---|
| 5,523,295 A | 6/1996 | Fasman |
| 7,935,726 B1 | 5/2011 | Hua |
| 2015/0119406 A1 | 4/2015 | Hua et al. |
| 2018/0044295 A1 | 2/2018 | Trushina et al. |

FOREIGN PATENT DOCUMENTS

| | | |
|---|---|---|
| WO | WO 2005/080317 | 9/2005 |
| WO | WO 2015/006520 | 1/2015 |

OTHER PUBLICATIONS

Braak and Braak, "Neuropathological staging of Alzheimer-related changes," Acta Neuropathol., 82(4):239-259, 1991.
Cretu et al., "Plant-Derived Anticancer Agents—Curcumin in Cancer Prevention and Treatment," Rev Med Chir Soc Med Nat Iasi., 116(4):1223-1229, Nov. 4, 2012.
Hardy et al., "The Amyloid Hypothesis of Alzheimer's Disease: Progress and Problems on the Road to Therapeutics," Science., 297:353-356, Jul. 19, 2002.
Hong et al., "Inhibition of Alzheimer's Amyloid Toxicity with a Tricyclic Pyrone Molecule In Vitro and In Vivo," J Neurochem., 108(4):1097-1108, Feb. 2009.
Hosogai et al., "Adipose Tissue Hypoxia in Obesity and Its Impact on Adipocytokine Dysregulation," Diabetes., 56:901-911, Apr. 2007.
Hua et al., "Syntheses and bioactivities of tricyclic pyrones," Tetrahedron, 59(26):4795-803, Jun. 2003.
(Continued)

*Primary Examiner* — Brian E McDowell
(74) *Attorney, Agent, or Firm* — Fish & Richardson P.C.

(57) ABSTRACT
Compounds and compositions that can modulate mitochondrial function in neuronal cells are provided herein, as are methods for using the compounds and compositions to treat or prevent conditions such as Alzheimer's disease. For example, compounds of Formula I, compositions containing the compounds, and methods for using the compounds and compositions are provided herein:

(I)

wherein X is absent, $CH_2$, or $C(O)$; $R^1$ is H, OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, or di($C_{1-3}$ alkyl)amino; $R^2$ is H or $C_{1-6}$ alkyl; $R^3$ is H, $C_{1-6}$ alkyl, —$C(O)(C_{1-3}$ alkyl), or —$C(O)O(C_{1-3}$ alkyl); $R^4$ is $C_{3-10}$ cycloalkyl, $C_{6-10}$ aryl, 5-10 membered heteroaryl, or 5-10 membered heterocycloalkyl, each optionally substituted by 1, 2, 3, or 4 independently selected $R^5$ groups; and $R^5$ is OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, or di($C_{1-3}$ alkyl)amino.

18 Claims, 44 Drawing Sheets

(56) References Cited

OTHER PUBLICATIONS

International Preliminary Report on Patentability in International Application No. PCT/US2016/20698, dated Sep. 5, 2017, 21 pages.
International Search Report and Written Opinion in International Application No. PCT/US2016/20698, dated May 5, 2016, 24 pages.
Lange et al., "Comprehensive method for culturing embryonic dorsal root ganglion neurons for Seahorse Extracellular Flux XF24 analysis," Front Neurol., 3:175, Dec. 2012.
Maezawa et al., "A novel tricyclic pyrone compound ameliorates cell death associated with intracellular amyloid-β oligomeric complexes," J Neurochem., 98:57-67, 2006.
Mondragon-Rodriguez et al., "Amyloid Beta and tau proteins as therapeutic targets for Alzheimer's disease treatment: rethinking the current strategy," Int J Alzheimers Dis., 2012:630182, 2012, 7 pages.
Pokhrel et al., "Inhibition of Acyl-CoA: Cholesterol Acyltransferase (ACAT), Overexpression of Cholesterol Transporter Gene, and Protection of Amyloid β (Aβ) Oligomers-Induced Neuronal Cell Death by Tricyclic Pyrone Molecules," J. Med. Chem., 55(20):8969-8973, Oct. 2012.
Pubchem SID 218184412, Oct. 20, 2014, pp. 1-6 [online], [retrieved on Apr. 14, 2016]. Retrieved from the Internet <URL:https://pubchem.ncbi.nlm.nih.gov/substance/218184412>, 6 pages.
Rana et al., "Syntheses of tricyclic pyrones and pyridinones and protection of Abeta-peptide induced MC65 neuronal cell death," Bioorg Med Chem Lett., 19(3):670-674, Feb. 1, 2009.
Sardi et al. Alzheimer's disease, autoimmunity and inflammation. The good, the bad and the ugly, Autoimmunity Reviews., 11:149-153, 2011.
Snyder et al., "Developing Novel Blood-Based Biomarkers for Alzheimer's Disease," Alzheimer's & Dementia., 10(1):109-114, Jan. 2014.
Spinazzi et al., "Assessment of mitochondrial respiratory chain enzymatic activities on tissues and cultured cells," Nat Protoc., 7(6):1235-1246, May 31, 2012.
Trushina and Mielke., "Recent advances of application of metabolomics in Alzheimer's Disease," Biochim Biophys Acta., 1842(8):1232-1239, Aug. 2013.
Trushina et al., "Identification of Altered Metabolic Pathways in Plasma and CSF in Mild Cognitive Impairment and Alzheimer's Disease Using Metabolomics," PLOS ONE., 8(5):e63644, May 2013.
Trushina et al., "Microtubule destabilization and nuclear entry are sequential steps leading to toxicity in Huntington's disease," PNAS., 100(21):12171-12176, Oct. 14, 2003.
Trushina et al., "Restoration of mitochondrial dynamics attenuates memory phenotype in multiple mouse models of familial Alzheimer's Disease in vivo," Cell Symposia., May 5-7, 2013, Lisbon, Portugal, Abstract only.
Trushina et al., "Tricyclic pyrone compounds prevent aggregation and reverse cellular phenotypes caused by expression of mutant huntingtin protein in striatal neurons," BMC Neurosci., 10:73, 2009.
Trushina., "From metabolic pathways to biomarkers: where are we now with metabolomics in Alzheimer's disease?," Future Neurology., 8(5):491-494, 2013.
Trushina., "Metabolomic signatures of energetic stress and mitochondrial dysfunction in mouse models and patients with early Alzheimer's disease to Disease," Cell Symposia., May 5-7, 2013, Lisbon, Portugal, Abstract only.
Turner et al. "A Mechanism for the action of berberine to activate AMP-activated protein kinase and improve insulin action," Diabetes., 57:1414-1418, May 2008.
Zhang et al., "Modulation of mitochondrial complex I activity averts cognitive decline in multiple animal models of familial Alzheimer's disease," eBioMedicine., 2:294-305, 2015.

FIG. 1

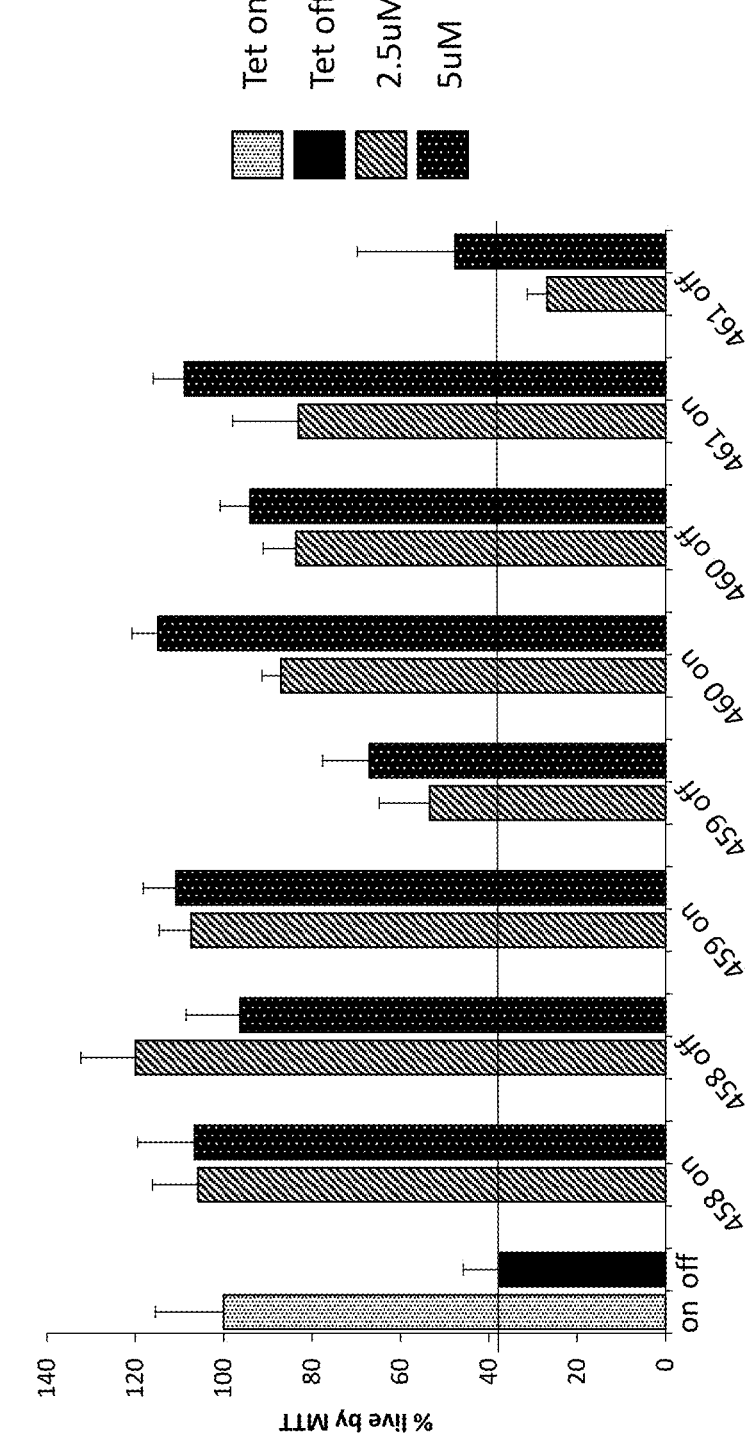

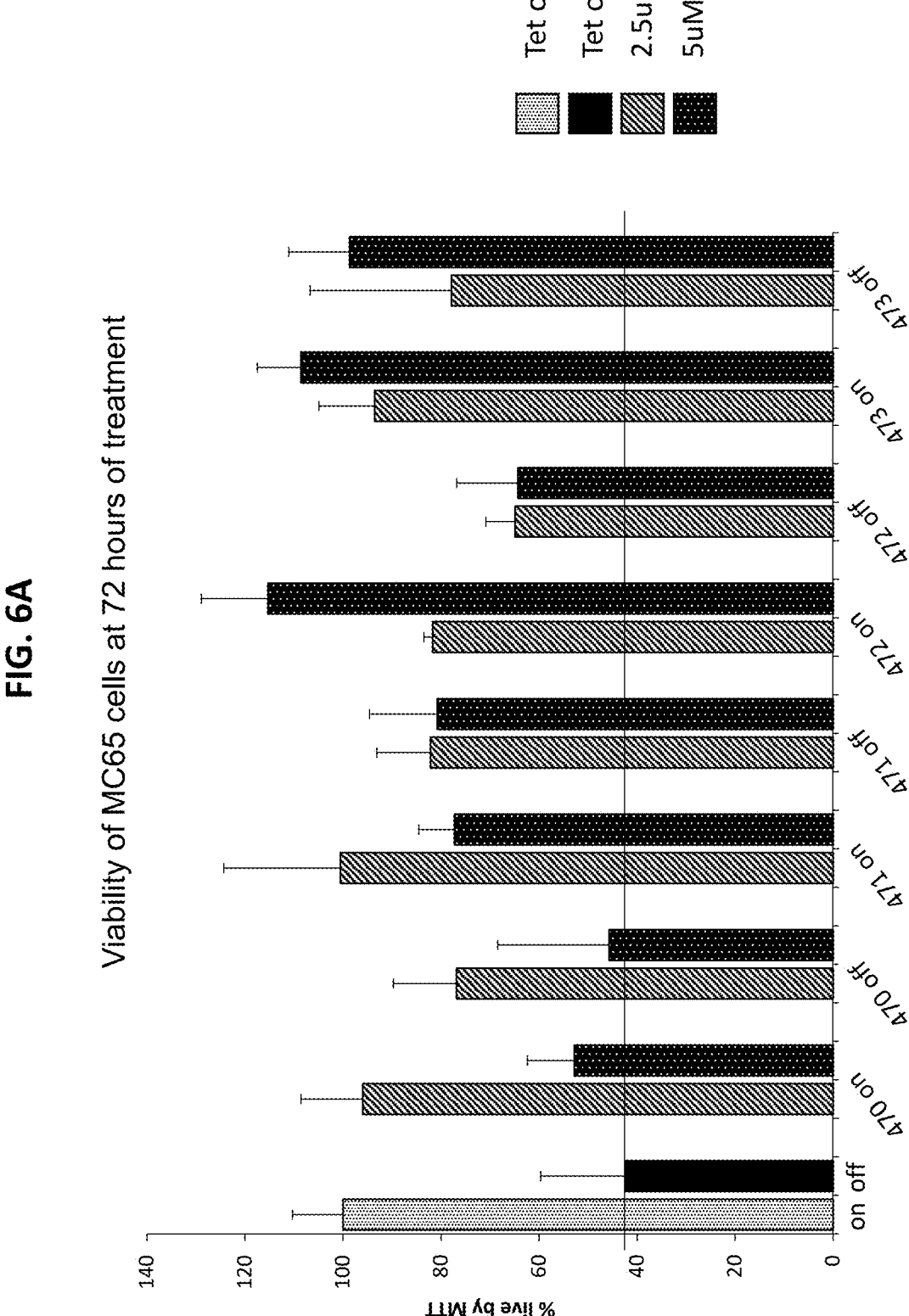

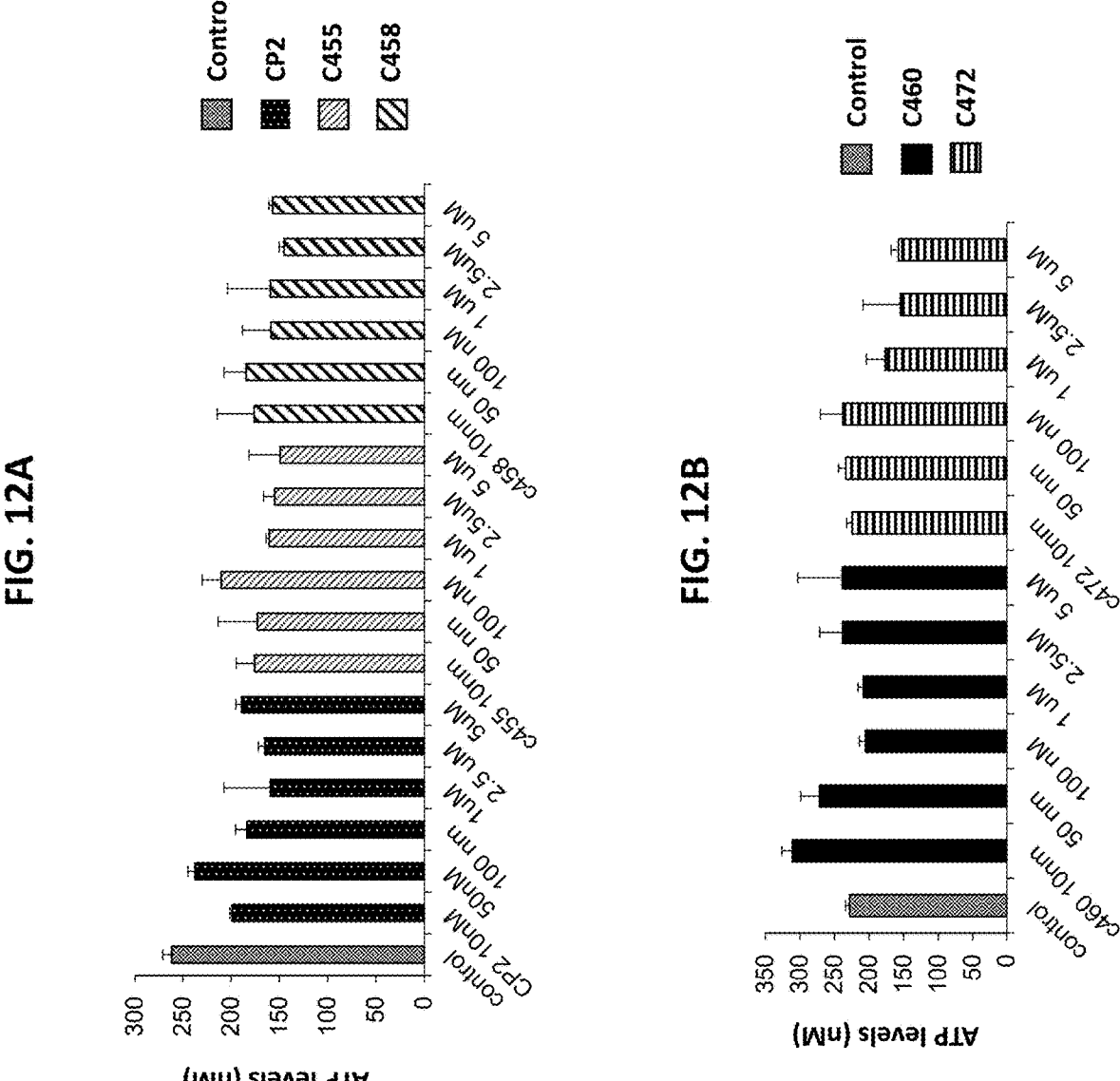

COMPOUNDS FOR MODULATING MITOCHONDRIAL FUNCTION

CROSS-REFERENCE TO RELATED APPLICATIONS

This application is a divisional of U.S. Ser. No. 15/554,767, filed Aug. 31, 2017, now U.S. Pat. No. 10,336,700, which is a National Stage application under 35 U.S.C. § 371 of International Application No. PCT/US2016/020698, having an International Filing Date of Mar. 3, 2016, which claims benefit of priority from U.S. Provisional Application No. 62/127,584, filed on Mar. 3, 2015.

TECHNICAL FIELD

This invention relates to compounds that can be used to treat neurodegenerative diseases, for example, by modulating mitochondrial function in neuronal cells.

BACKGROUND

Neurodegenerative diseases occur when changes in the neurons of the brain and spinal cord cause them to function abnormally, eventually result in their deterioration and death. Symptoms may initially be mild, but they progressively worsen as more and more neurons die. For example, Alzheimer's disease (AD) is a devastating neurodegenerative disorder that has no cure, and is associated with progressive cognitive decline in the aging population. Extracellular amyloid beta (Aβ) plaques and intracellular neurofibrillary tangles (NFTs) comprised of hyperphosphorylated tau (p-tau) protein represent the major hallmarks of AD pathology (Braak and Braak, *Acta Neuropathologica*, 82:239-259, 1991). The etiology of sporadic AD, which represents over 95% of all cases, is unknown, with age being the single risk factor. Familial AD (FAD) is caused by mutations in presenilin 1 and 2 (PS1 and PS2) and amyloid precursor protein (APP), all of which are involved in the abnormal processing of APP, leading to increased levels of Aβ. The specific molecular mechanisms of sporadic and familial AD are still under investigation, hindering the development of effective therapeutic approaches. Emerging data from multiple animal studies and clinical investigations, however, suggest that there is a tight connection between Aβ and p-tau, and development of strategies that target both mechanisms could be beneficial (Mondragon-Rodriguez et al., *Int J Alzheimers Dis*, 2012:630182, 2012).

SUMMARY

Altered mitochondrial dynamics is an underlying and early event in progression of neurodegenerative diseases such as AD, amyotrophic lateral sclerosis (ALS), Huntingon's disease (HD), and Parkinson's disease (PD). This document is based in part on the identification of molecules that can efficiently restore mitochondrial dynamics in neurons and enhance their bioenergetics. A tricyclic pyrone compound (CP2) can restore axonal trafficking of mitochondria in neurons, alleviating the development of behavior and memory phenotypes in multiple transgenic mouse models of FAD. As described herein, an array of new experimental compounds was subjected to biological screening to assess their toxicity, and to identify compounds that possess the ability to restore mitochondrial function in cells that express amyloid beta peptides. Four classes of compounds with properties superior to CP2 were identified, and several of those compounds were characterized in primary neurons. This document provides compounds from those classes, as well as compositions containing one or more of the compounds, and methods for making and using the compounds and compositions to treat, prevent, or delay the onset of AD. It is to be noted that these compounds and compositions also may be beneficial in treating, preventing, or delaying the onset of other diseases and disorders, such as HD, PD, dementia (e.g., frontotemporal dementia), traumatic brain injury (TBI), multiple sclerosis (MS), ALS, diabetes, metabolic syndrome, cancer, chemotherapy-induced peripheral neuropathies, Down Syndrome, and aging. Such compounds also may increase health span and fecundity, promoting a prolonged period of health with increasing age, and delaying the onset of age-related diseases.

In a first aspect, this document features a compound of Formula (I):

(I)

or a pharmaceutically acceptable salt thereof, wherein:

X is absent or selected from the group consisting of $CH_2$ and $C(O)$;

$R^1$ is selected from the group consisting of H, OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino;

$R^2$ is selected from the group consisting of H and $C_{1-6}$ alkyl;

$R^3$ is selected from the group consisting of H, $C_{1-6}$ alkyl, —$C(O)(C_{1-3}$ alkyl), and —$C(O)O(C_{1-3}$ alkyl);

$R^4$ is selected from the group consisting of $C_{3-10}$ cycloalkyl, $C_{6-10}$ aryl, 5-10 membered heteroaryl, and 5-10 membered heterocycloalkyl, each optionally substituted by 1, 2, 3, or 4 independently selected $R^5$ groups; and $R^5$ is selected from the group consisting of OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino.

In some embodiments, X can be $CH_2$. In some embodiments, wherein $R^1$ can be $C_{1-3}$ alkyl. In some embodiments, $R^2$ can be $C_{1-6}$ alkyl. In some embodiments, $R^3$ can be H. In some embodiments, $R^4$ can be unsubstituted 5-10 membered heteroaryl. In some embodiments, $R^4$ can be aryl and $R^5$ can be halo or OH.

The compound of Formula (I) can be a compound of Formula (Ia):

(Ia)

or a pharmaceutically acceptable salt thereof.

The compound of Formula (I) can be a compound of Formula (II):

(II)

or a pharmaceutically acceptable salt thereof.

wherein:

X is absent or selected from the group consisting of $CH_2$ and $C(O)$;

$R^1$ is selected from the group consisting of H, OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino;

$R^2$ is selected from the group consisting of H and $C_{1-6}$ alkyl;

$R^3$ is selected from the group consisting of H, $C_{1-6}$ alkyl, —C(O)($C_{1-3}$ alkyl), and —C(O)O($C_{1-3}$ alkyl);

$R^4$ is selected from the group consisting of $C_{3-10}$ cycloalkyl, $C_{6-10}$ aryl, 5-10 membered heteroaryl, and 5-10 membered heterocycloalkyl, each optionally substituted by 1, 2, 3, or 4 independently selected $R^5$ groups; and $R^5$ is selected from the group consisting of OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino.

In some embodiments, X can be $CH_2$. In some embodiments, $R^1$ can be $C_{1-3}$ alkyl. In some embodiments, $R^2$ can be $C_{1-6}$ alkyl. In some embodiments, $R^3$ can be H. In some embodiments, $R^4$ can be unsubstituted 5-10 membered heteroaryl. In some embodiments, $R^4$ can be aryl and $R^5$ can be halo or OH.

The compound of Formula (II) can be a compound of Formula (IIa)

(IIa)

or a pharmaceutically acceptable salt thereof.

The compound of Formula (I) can be selected from the group consisting of:

-continued or a pharmaceutically acceptable salt thereof.
The compound of Formula (I) can be or a pharmaceutically acceptable salt thereof.

In another aspect, this document features a pharmaceutical composition containing a compound as provided herein, or a pharmaceutically acceptable salt thereof, in combination with a pharmaceutically acceptable carrier.

In another aspect, this document features a method for modulating mitochondrial function in a subject. The method can include administering to the subject a therapeutically effective amount of a compound as provided herein, or a pharmaceutically acceptable salt thereof. The subject can be a human. The subject can be diagnosed as having a neurodegenerative disorder. The subject can be diagnosed as having diabetes, metabolic syndrome, cancer, a chemotherapy-induced peripheral neuropathy, or Down syndrome.

In yet another aspect, this document features a method for treating a neurodegenerative disorder in a subject. The method can include administering to the subject a therapeutically effective amount of a compound of as described herein, or a pharmaceutically acceptable salt thereof. The method can include administering the compound in an amount effective to reduce cognitive decline in the subject. The neurodegenerative disorder can be AD, HD, PD, dementia, MS, or ALS. For example, the neurodegenerative disorder can be AD, and the method can include administering the compound in an amount effective to reduce the formation or amount of Aβ plaques or neurofibrillary tangles (NFTs) in the subject.

In still another aspect, this document features a method for reducing the likelihood of AD in a subject at risk for developing AD. The method can include administering to the subject a therapeutically effective amount of a compound as provided herein, or a pharmaceutically acceptable salt thereof. The subject can be a human. The subject can have been identified as having a mutation in a PS1, PS2, or APP gene that is associated with AD.

This document also features a method for modulating mitochondrial function in a cell. The method can include contacting the cell with an effective amount of a compound as provided herein, or a pharmaceutically acceptable salt thereof. The amount can be effective to modulate ATP production, Complex I activity, NADH levels, and/or $NAD^+/NADH$ ratio in the cell. The contacting can be in vitro. The amount can be effective to reduce Complex I activity. The cell can be within a subject identified as having hypoxia or ischemia.

In addition, this document features a method for treating cancer in a subject. The method can include administering to the subject a therapeutically effective amount of a compound as described herein, or a pharmaceutically acceptable salt thereof. The cancer can be, for example, pancreatic cancer, cervical cancer, or lymphoma. The subject can be a human. The method compound can be administered in an amount effective to reduce the severity, progression, or recurrence of the cancer Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows the structure of the CP2 molecule. $ED_{50}$=0.12 μM, $TD_{50}$=39 TI=325.

FIG. 2B, C462-C473). Cell viability was measured 48 hours later using an MTT assay. Cell viability is expressed as a percent of vehicle-treated (control) cells. All experiments were performed twice in triplicates.

FIG. 3B, vehicle and C464-C473). Cell viability was measured 24 hours later with an MTT assay. Cell viability is expressed as a percent of vehicle-treated (control) cells. All experiments were performed twice in triplicates.

FIG. 4B, C454-C457) at 2.5 μM and 5 μM. Cell viability was measured with an MTT assay 72 hours later. Experiments were performed in triplicates. Every 96-well plate had its own on/off control. Four experimental compounds were tested per each plate. Experiments were repeated independently twice.

FIGS. 5A and 5B are a pair of graphs plotting survival of MC65 cells after treatment with the indicated compounds, in the presence (Tet/off) or absence (Tet/on) of Aβ expression. MC65 cells were cultured for 72 hours in the presence (on) or absence (off) of tetracycline in OPTI-MEM media without serum. Cells (Tet/on and Tet/off) at the time of plating were treated every 24 hours with vehicle (0.05% final DMSO) or experimental compounds (FIG. 5A, C458-C461; FIG. 5B, C462-C465) at 2.5 μM and 5 μM. Cell viability was measured with an MTT assay 72 hours later. Experiments were performed in triplicates. Every 96-well plate had its own on/off control. Four experimental compounds were tested per each plate. Experiments were repeated independently twice.

FIG. 6A is a graph plotting survival of MC65 cells after treatment with the indicated compounds, in the presence (Tet/off) or absence (Tet/on) of Aβ expression. MC65 cells were cultured for 72 hours in the presence (on) or absence (off) of tetracycline in OPTI-MEM media without serum. Cells (Tet/on and Tet/off) at the time of plating were treated every 24 hours with vehicle (0.05% final DMSO) or experimental compounds (C470-C473) at 2.5 μM and 5 μM. Cell viability was measured with an MTT assay 72 hours later. Experiments were performed in triplicates. Every 96-well plate had its own on/off control. Four experimental compounds were tested per each plate. Experiments were repeated independently twice.

FIG. 8A, C455; FIG. 8B, C458; FIG. 8C, C460; FIG. 8D, C472.

FIG. 9A, C455; FIG. 9B, C458; FIG. 9C, C460; FIG. 9D, C472.

FIGS. 11A and 11B are graphs plotting survival of MC65 cells cultured for 72 hours in the presence (on; FIG. 11A) or absence (off; FIG. 11B) of tetracycline in OPTI-MEM media without serum. Cells (Tet/on and Tet/off) at the time of plating were treated with either vehicle (0.05% final DMSO) or experimental compounds at 2.5 μM every 24 hours. Cell viability was measured with an MTT assay 72 hours later. Experiments were performed in triplicate, and every 96-well plate had its own on/off control. Four experimental compounds were tested per plate. Experiments were repeated independently twice.

FIGS. 12A and 12B are a pair of graphs plotting ATP levels in primary embryonic cortical neurons that were seeded on 96-well plates at 30,000 cells per well and treated with the indicated compounds at concentrations ranging from 10 nM to 5 as indicated. ATP levels were measured 24 hours later using an ATP determination Kit (Life Technologies; Carlsbad, Calif.). ATP levels are expressed as a percent of vehicle treated (control) cells. All experiments were performed twice in 6 replicates.

FIG. 20A, HeLa cervical cancer cells; FIG. 20B, Panc1 pancreatic cancer cells; FIG. 20C, P-WT: mouse embryonic fibroblasts (MEFs; control); FIG. 20D, P++: MEFs; FIG. 20E, p53−/− ms T-cell lymphoma (TCL) cells; FIG. 20F, Patu pancreatic cancer cells; FIG. 20G, Su pancreatic cancer cells.

FIG. 21A, HeLa cervical cancer cells; FIG. 21B, Panc1 pancreatic cancer cells; FIG. 21C, P-WT: MEFs; control); FIG. 21D, P++: MEFs; FIG. 21E, p53−/− ms TCL; FIG. 21F, Patu pancreatic cancer cells; FIG. 21G, Su pancreatic cancer cells; FIG. 21H, HPDE control.

DETAILED DESCRIPTION

Definitions

Figure 2A:
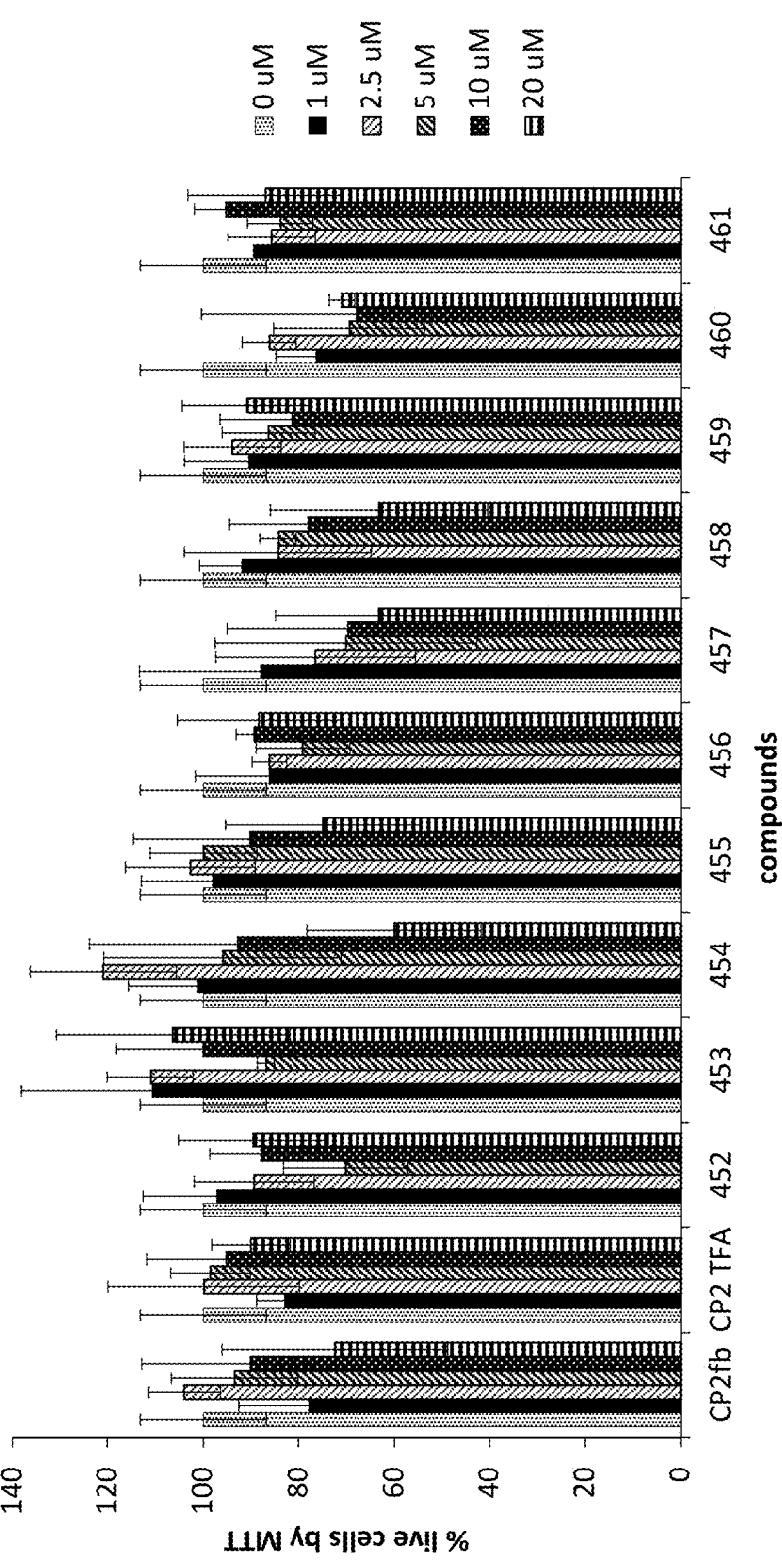
FIGS. 2A and 2B are a pair of graphs plotting survival of SK-N-MC cells after treatment with the indicated compounds. Cells were seeded in 96-well plates at 30,000 cells per well. Twenty four (24) hours later, cells were treated with 1, 2.5, 5, 10, or 20 μM of the indicated compounds (FIG. 2A, CP2 free base, CP2 TFA salt, and C452-C461.

For the terms "for example" and "such as," and grammatical equivalences thereof, the phrase "and without limitation" is understood to follow unless explicitly stated otherwise. All measurements reported herein are understood to be modified by the term "about", whether or not the term is explicitly used, unless explicitly stated otherwise. As used herein, the singular forms "a," "an," and "the" include plural referents unless the context clearly dictates otherwise.

The terms "treating" and "treatment" mean causing a therapeutically beneficial effect, such as ameliorating one or more existing symptoms and/or reducing the severity of symptoms that will or are expected to develop.

A "therapeutically effective" amount of a compound as described herein is typically one that is sufficient to achieve the desired effect and may vary according to the nature and severity of the disease condition, and the potency of the compound. It will be appreciated that different concentrations may be employed for prophylaxis than for treatment of an active disease.

The term "contacting" means bringing at least two moieties together, whether in an in vitro system or an in vivo system.

As used herein, "administration" refers to delivery of a compound or composition containing a compound provided herein by any external route, including, without limitation, IV, intramuscular, SC, intranasal, inhalation, transdermal, oral, buccal, rectal, sublingual, and parenteral administration.

The term "compound" as used herein is meant to include all stereoisomers, geometric isomers, and tautomers of the structures depicted. Compounds herein identified by name or structure as one particular tautomeric form are intended to include other tautomeric forms, unless otherwise specified.

In some embodiments, a compound provided herein, or salt thereof, is substantially isolated. By "substantially isolated" is meant that the compound is at least partially or substantially separated from the environment in which it was formed or detected. Partial separation can include, for example, a composition enriched in the compound provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The phrase "pharmaceutically acceptable" is used herein to refer to those compounds, materials, compositions, and/or dosage forms that are, within the scope of sound medical judgment, suitable for use in contact with the tissues of humans and animals (e.g., non-human mammals such as mice, rats, cats, dogs, pigs, cows, sheep, or horses) without excessive toxicity, irritation, allergic response, or other problem or complication, commensurate with a reasonable benefit/risk ratio.

The term "alkyl" includes substituted or unsubstituted straight-chain alkyl groups (e.g., methyl, ethyl, propyl, butyl, pentyl, hexyl, heptyl, octyl, nonyl, decyl, etc.) and branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl, etc.), alkyl substituted cycloalkyl groups, and cycloalkyl substituted alkyl groups. In certain embodiments, a straight chain or branched chain alkyl has six or fewer carbon atoms in its backbone (e.g., $C_{1-6}$ for straight chain; $C_{3-6}$ for branched chain). The term $C_{1-6}$ includes alkyl groups containing 1 to 6 carbon atoms. In certain embodiments, a straight chain alkyl has three or fewer carbon atoms in its backbone. The term $C_{1-3}$ includes alkyl groups containing one to three carbon atoms.

As used herein, "haloalkyl" means a hydrocarbon substituent, which is a linear or branched or cyclic alkyl, alkenyl or alkynyl substituted with one or more chloro, bromo, fluoro, or iodo atom(s). In some embodiments, a haloalkyl is a fluoroalkyl, wherein one or more of the hydrogen atoms have been substituted by fluoro. In some embodiments, haloalkyls are one to about three carbons in length (e.g., one to about two carbons in length, or one carbon in length).

The term "cycloalkyl" includes a substituted or unsubstituted cyclic aliphatic group which may be saturated or unsaturated. For example, cycloalkyl groups include cyclopropyl, cyclopentyl, cyclohexyl, cycloheptyl, and cyclooctyl. In some embodiments, cycloalkyls can have from three to seven carbon atoms in their ring structure; for example, a cycloalkyl can have three, four, five, six, or seven carbons in the ring structure.

The term "alkoxy" includes groups of the formula —OR, where R is an alkyl as defined herein. Non-limiting examples of alkoxy groups include methoxy, ethoxy, isopropoxy, tert-butoxy, and the like. In some embodiments, an alkoxy group can have from one to three carbons (e.g., methyoxy, ethoxy, or propoxy).

The term "haloalkoxy" includes group of the formula —OR, where R is a haloalkyl as defined herein. Examples of haloalkoxy groups include, without limitation, trifluoromethoxy, difluoromethoxy, etc.

"Alkylamino" includes groups of the formula —NR, where R is an alkyl as defined herein. Non-limiting examples of alkylamino groups include methylamino, ethylamino, isopropylamino, butylamino etc. In some embodiments, an alkylamino group can have from one to three carbons (e.g., methyoxy, ethoxy, or propoxy). The term "dialkylamino" includes groups of the formula —$NR_2$, where R is an alkyl as defined herein. In some embodiments, the alkyl groups of a dialkylamino independently can have one to three carbons.

In general, the term "aryl" includes substituted or unsubstituted aromatic rings, including 5- and 6-membered single-ring aromatic groups, such as benzene and phenyl. Further, the term "aryl" includes multicyclic aryl groups, e.g., tricyclic, bicyclic, such as naphthalene and anthracene. In some embodiments, aryls can have from six to ten (e.g., six, seven, eight, nine, or ten) ring atoms.

The term "heteroaryl" means a substituted or unsubstituted mono-, bi-, tri- or polycyclic group having four to 14 ring atoms, alternatively five, six, nine, or ten ring atoms; having six, ten, or 14 pi electrons shared in a cyclic array; wherein at least one ring in the system is aromatic, and at least one ring in the system contains one or more heteroatoms independently selected from the group consisting of N, O, and S. Exemplary heteroaryl groups include, for example, pyrrole, furan, thiophene, thiazole, isothiaozole, imidazole, triazole, tetrazole, pyrazole, oxazole, isooxazole, pyridine, pyrazine, pyridazine, and pyrimidine, and the like. Further, the term "heteroaryl" includes multicyclic heteroaryl groups, e.g., tricyclic or bicyclic groups, such as benzoxazole, benzodioxazole, benzothiazole, benzoimidazole, benzothiophene, methylenedioxyphenyl, quinoline, isoquinoline, napthyridine, indole, benzofuran, purine, benzofuran, quinazoline, deazapurine, indazole, or indolizine.

The term "heterocycloalkyl" includes substituted or unsubstituted groups, including but not limited to, three- to ten-membered single or multiple rings having one to five heteroatoms, for example, piperazine, pyrrolidine, piperidine, or homopiperazine. In certain embodiments, a heterocycloalkyl can have from four to ten ring atoms. The term "substituted" means that an atom or group of atoms replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position. In some cases, two sites of substitution may come together to form a 3-10 membered cycloalkyl or heterocycloalkyl ring. Non-limiting examples of substituents include: $(C_1-C_6)$alkyl, halo, $(C_1-C_6)$haloalkyl, —CN, —$NR^8R^9$, —$NO_2$, —$O(C_1-C_6)$haloalkyl, —$OC(O)R^8$, —$C(O)R^8$, —$C(O)OR^8$, —$C(O)NR^8R^9$, —$S(O)R^8$, —$SO_2R^8$, —$SO_2NR^8R^9$, $(C_3-C_7)$cycloalkyl, $(C_3-C_7)$heterocycloalkyl, $(C_5-C_{14})$aryl, and $(C_5-C_{14})$heteroaryl, wherein $R^8$ and $R^9$ are independently selected from H and $(C_1-C_6)$ alkyl.

Modulators of Mitochondrial Function

This document provides compounds that can modulate mitochondrial function and induce metabolic reprogramming, as well as methods and materials for using such compounds to treat disorders such as AD and other neurological conditions. Thus, in some embodiments, this document provides compounds that can be used to restore mitochondrial function in cells (e.g., primary neurons) that express Aβ peptides. Provided herein are, inter alia, the following compounds:

(also referred to herein as C455)

(also referred to herein as C458)

(also referred to herein as C460)

(also referred to herein as C472)

or a pharmaceutically acceptable salt thereof.

It is to be noted that this document encompasses not only the various isomers, diastereomers, enantiomers, and tautomers that may exist, but also the various mixtures of isomers, diastereomers, enantiomers, and tautomers that may be formed.

The scope of this document also encompasses solvates and salts of the compounds described herein, as well as prodrugs of the compounds, such as esters, amides, and acylated groups, among others. In some embodiments, for example, this document provides prodrugs of the compounds disclosed herein, which may contain, for example, acylated phenols or acyl derivatives of amines. By "prodrug" is meant, for example, any compound (whether itself active or inactive) that is converted chemically in vivo into a biologically active compound as provided herein, following administration of the prodrug to a subject. In some embodiments, a prodrug is a covalently bonded carrier that releases the active parent drug when administered to a subject. Prodrugs can be prepared by modifying functional groups present in the compounds in such a way that the modifications are cleaved, either in routine manipulation or in vivo, to the parent compounds. Prodrugs can include compounds in which hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, without limitation, acetate, formate and benzoate derivatives of alcohol and amine functional groups in the compounds provided herein. The suitability and techniques involved in making and using prodrugs are discussed in Higuchi and Stella, "Pro-drugs as Novel Delivery Systems," Vol. 14 of the ACS Symposium Series, and in *Bioreversible Carriers in Drug Design*, ed. Edward B. Roche, American Pharmaceutical Association and Pergamon Press, 1987, both of which are hereby incorporated by reference in their entirety.

Also provided herein is a compound of Formula (I):

(I)

or a pharmaceutically acceptable salt thereof, where:
X is absent or selected from the group consisting of $CH_2$ and $C(O)$;
$R^1$ is selected from the group consisting of H, OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino;
$R^2$ is selected from the group consisting of H and $C_{1-6}$ alkyl;
$R^3$ is selected from the group consisting of H, $C_{1-6}$ alkyl, —$C(O)(C_{1-3}$ alkyl), and —$C(O)O(C_{1-3}$ alkyl);
$R^4$ is selected from the group consisting of $C_{3-10}$ cycloalkyl, $C_{6-10}$ aryl, 5-10 membered heteroaryl, and 5-10 membered heterocycloalkyl, each optionally substituted by 1, 2, 3, or 4 independently selected $R^5$ groups; and
$R^5$ is selected from the group consisting of OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino.

In some embodiments, X is $CH_2$. In some embodiments, $R^1$ is $C_{1-3}$ alkyl. For example, $R^1$ can be methyl. In some embodiments, $R^2$ is $C_{1-6}$ alkyl. For example, $R^2$ can be methyl. In some embodiments, $R^3$ is H. In some embodiments, $R^4$ is unsubstituted 5-10 membered heteroaryl. For example, $R^4$ can be phenyl, pyridinyl, cyclohexanyl, and benzoimidazolyl. In some embodiments, $R^4$ is aryl (e.g., phenyl) and $R^5$ is halo (e.g., chloro) or OH.

In some embodiments, the compound of Formula (I) can have the following stereochemistry:

(I)

where $R^1$, $R^2$, $R^3$, and $R^4$ are as set forth above.

In some embodiments, the compound of Formula (I) can be a compound of Formula (II):

(II)

or a pharmaceutically acceptable salt thereof,
where:
X is absent or selected from the group consisting of $CH_2$ and $C(O)$;
$R^1$ is selected from the group consisting of H, OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino;
$R^2$ is selected from the group consisting of H and $C_{1-6}$ alkyl;
$R^3$ is selected from the group consisting of H, $C_{1-6}$ alkyl, —$C(O)(C_{1-3}$ alkyl), and —$C(O)O(C_{1-3}$ alkyl);
$R^4$ is selected from the group consisting of $C_{3-10}$ cycloalkyl, $C_{6-10}$ aryl, 5-10 membered heteroaryl, and 5-10 membered heterocycloalkyl, each optionally substituted by 1, 2, 3, or 4 independently selected $R^5$ groups; and
$R^5$ is selected from the group consisting of OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino.

In some embodiments, $R^1$ is $C_{1-3}$ alkyl. For example, $R^1$ can be methyl. In some embodiments, $R^2$ is $C_{1-6}$ alkyl. For example, $R^2$ can be methyl. In some embodiments, $R^3$ is H. In some embodiments, $R^4$ is unsubstituted 5-10 membered heteroaryl. For example, $R^4$ can be phenyl, pyridinyl, cyclohexanyl, and benzoimidazolyl. In some embodiments, $R^4$ is aryl (e.g., phenyl) and $R^5$ is halo (e.g., chloro) or OH.

In some embodiments, the compound of Formula (II) can have the following stereochemistry:

(II)

where $R^1$, $R^2$, $R^3$, and $R^4$ are as set forth above.

Also provided herein is a compound of Formula (III):

(III)

or a pharmaceutically acceptable salt thereof,
where:
V, W, Y, and Z are independently selected from the group consisting of CH and N;
X is absent or selected from the group consisting of $CH_2$ and $C(O)$;
m is an integer from 0 to 2;
n is an integer from 0 to 2;
$R^1$ is selected from the group consisting of H, OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino;
$R^2$ is selected from the group consisting of H and $C_{1-6}$ alkyl;

$R^3$ is selected from the group consisting of H and $C_{1-6}$ alkyl;

$R^4$ is selected from the group consisting of H, $C_{1-6}$ alkyl, —C(O)($C_{1-3}$ alkyl), and C(O)O($C_{1-3}$ alkyl);

$R^5$ is selected from the group consisting of $C_{3-10}$ cycloalkyl, $C_{6-10}$ aryl, 5-10 membered heteroaryl, and 5-10 membered heterocycloalkyl, each optionally substituted by 1, 2, 3, or 4 independently selected $R^6$ groups; and $R^6$ is selected from the group consisting of OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino.

As indicated in Formula (III), the central cycloalkyl ring can be a cyclopentyl, cyclohexyl, or cycloheptyl ring. It is to be noted that in some embodiments, the central ring may be a phenyl ring or a heterocyclic structure (e.g., a pyridyl ring). Thus, in some embodiments, this document also provides compounds of Formulae (IV)-(VII):

(IV)

(V)

(VI)

(VII)

or a pharmaceutically acceptable salt thereof,
where:
the central aromatic ring contains 1 or more nitrogen atoms;

X is absent or selected from the group consisting of $CH_2$ and C(O);

$R^1$ is selected from the group consisting of H, OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino;

$R^2$ is selected from the group consisting of H and $C_{1-6}$ alkyl;

$R^3$ is selected from the group consisting of H, $C_{1-6}$ alkyl, —C(O)($C_{1-3}$ alkyl), and —C(O)O($C_{1-3}$ alkyl);

$R^4$ is selected from the group consisting of $C_{3-10}$ cycloalkyl, $C_{6-10}$ aryl, 5-10 membered heteroaryl, and 5-10 membered heterocycloalkyl, each optionally substituted by 1, 2, 3, or 4 independently selected $R^5$ groups; and $R^5$ is selected from the group consisting of OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino.

Also provided herein is a compound of Formula (VIII):

(VIII)

or a pharmaceutically acceptable salt thereof,
where:
A, B, D, E, W, Y, and Z are independently selected from the group consisting of
CH and N;

X is absent or selected from the group consisting of $CH_2$ and C(O);

n is an integer from 0 to 2;

$R^1$ is selected from the group consisting of H, OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino;

$R^2$ is selected from the group consisting of H and $C_{1-6}$ alkyl;

$R^3$ is selected from the group consisting of H and $C_{1-6}$ alkyl;

$R^4$ is selected from the group consisting of H, $C_{1-6}$ alkyl, —C(O)($C_{1-3}$ alkyl), and C(O)O($C_{1-3}$ alkyl);

$R^5$ is selected from the group consisting of $C_{3-10}$ cycloalkyl, $C_{6-10}$ aryl, 5-10 membered heteroaryl, and 5-10 membered heterocycloalkyl, each optionally substituted by 1, 2, 3, or 4 independently selected $R^6$ groups; and $R^6$ is selected from the group consisting of OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino.

Again, it is to be noted that this document encompasses not only the various isomers, diastereomers, enantiomers, and tautomers that may exist for the compounds described herein, but also the various mixtures of isomers, diastereomers, enantiomers, and tautomers that may be formed Non-limiting examples of compounds according to the above Formulae include:

-continued or a pharmaceutically acceptable salt thereof.

Most of these compounds also are shown in TABLE 3 below. Methods for making such compounds include those known in the art and described herein.

In some embodiments, these compounds can have the following stereochemistry:

-continued

As used herein, chemical structures that contain one or more stereocenters depicted with bold and dashed bonds are meant to indicate absolute stereochemistry of the stereocenter(s) present in the chemical structure. As used herein, bonds symbolized by a simple line do not indicate a stereopreference. Unless indicated to the contrary, chemical structures that include one or more stereocenters and are illustrated herein without indicating absolute or relative stereochemistry encompass all possible steroisomeric forms of the compound (e.g., diastereomers and enantiomers) and mixtures thereof. Structures with a single bold or dashed line, and at least one additional simple line, encompass a single enantiomeric series of all possible diastereomers.

A compound provided herein, including a pharmaceutically acceptable salt thereof, can be purchased commercially or prepared using organic synthesis techniques. See, for example, the Examples herein.

A reaction for preparing a compound provided herein can be carried out in suitable solvents that can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of a compound can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry*, 1st Ed., Oxford University Press, 2000; and *March's Advanced Organic chemistry: Reactions, Mechanisms, and Structure*, 5th Ed., Wiley-Interscience Publication, 2001 (each of which is incorporated herein by reference in its entirety).

Pharmaceutically Acceptable Salts and Compositions

This document also provides pharmaceutically acceptable salts of the compounds provided herein. Examples of pharmaceutically acceptable salts of the compounds provided herein include acid addition salts and base salts of the compounds.

Suitable acid addition salts are formed from acids that form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, oxalate, palmitate, pamoate, phosphate/hydrogen, phosphate/phosphate dihydrogen, pyroglutamate, saccharate, stearate, succinate, tannate, D- and L-tartrate, 1-hydroxy-2-naphthoate tosylate, and xinafoate salts.

Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine, and zinc salts.

Hemisalts (e.g., hemisulphate and hemicalcium salts) of acids and bases may also be formed.

A compound provided herein intended for pharmaceutical use can be administered as a crystalline or amorphous product. In some cases, such a product can be obtained, for example, as a solid plug, powder, or film by methods such as precipitation, crystallization, freeze drying, spray drying, or evaporative drying. Microwave or radio frequency drying may be used for this purpose.

A compound can be formulated for administration by any route, including orally, rectally, sublingually, and parenterally. Parenteral administration includes, for example, intravenous, intramuscular, intraarterial, intraperitoneal, intranasal, intravaginal, intravesical (e.g., to the bladder), intradermal, transdermal, topical or subcutaneous administration. Also contemplated is the installation of a compound in the body of a patient in a controlled formulation, with systemic or local release of a compound to occur at a later time. For example, a compound can be localized in a depot for controlled release to the circulation, or for release to a local site. Advantageously, a compound can be administered in the form of a pharmaceutical composition.

This document also provides pharmaceutical compositions containing one or more compounds as described herein, or an individual isomer, racemic or non-racemic mixture of isomers, or a pharmaceutically acceptable salt or solvate thereof, together with at least one pharmaceutically acceptable carrier, and optionally other therapeutic and/or prophylactic ingredients.

A compound as provided herein can be administered alone or in combination with one or more other compounds provided herein, or in combination with one or more other drugs (or as any combination thereof). Generally, a compound will be administered as a formulation in association with one or more pharmaceutically acceptable excipients. The term "excipient" is used herein to describe any ingredient other than a compound(s) provided herein. The choice of excipient will to a large extent depend on factors such as the particular mode of administration, the effect of the excipient on solubility and stability, and the nature of the dosage form.

Non-limiting examples of pharmaceutical excipients suitable for administration of the compounds provided herein include any such carriers known to those skilled in the art to be suitable for the particular mode of administration. Pharmaceutically acceptable excipients include, without limitation, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of a compound provided herein. In some embodiments, the excipient is a physiologically acceptable saline solution.

In some embodiments, a pharmaceutical composition can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal ointments, creams, gels, and patch preparations and dry powder inhalers (see, e.g., *Ansel Introduction to Pharmaceutical Dosage Forms*, Fourth Edition 1985, 126).

The concentration of a compound in a pharmaceutical composition will depend on absorption, inactivation, and excretion rates of the compound, the physicochemical characteristics of the compound, the dosage schedule, and the amount administered, as well as other factors known to those of skill in the art.

A pharmaceutical composition can be administered at once, or can be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions can be provided for administration to humans and animals in unit dosage forms, such as tablets, capsules, pills, powders, granules, sterile parenteral solutions or suspensions, oral solutions or suspensions, and oil-water emulsions containing suitable quantities of the compound(s). The pharmaceutically therapeutically active compounds are, in some embodiments, formulated and administered in unit-dosage forms or multiple-dosage forms. Unit-dose forms as used herein refers to physically discrete units suitable for human and animal patients and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses that are not segregated in packaging.

Liquid pharmaceutically administrable compositions can be prepared by, for example, dissolving, dispersing, or otherwise mixing a compound as provided herein and optional pharmaceutical adjuvants in a carrier such as, without limitation, water, saline, aqueous dextrose, glycerol, glycols, ethanol, and the like, to form a solution or suspension. If desired, a pharmaceutical composition to be administered also can contain minor amounts of nontoxic auxiliary substances such as wetting agents, emulsifying agents, solubilizing agents, pH buffering agents and the like (e.g., acetate, sodium citrate, cyclodextrine derivatives, sorbitan monolaurate, triethanolamine sodium acetate, triethanolamine oleate, and other such agents).

Dosage forms or compositions can contain a compound as provided herein in the range of 0.005% to 100%, with the balance made up from one or more non-toxic carriers. Methods for preparation of these compositions are known to those skilled in the art. The contemplated compositions may contain 0.001%-100% active ingredient. In some embodiments, for example, a composition can contain 0.1-95% active ingredient, and in other embodiments, a composition can contain 75-85% active ingredient.

Pharmaceutical compositions suitable for the delivery of compounds provided herein, as well as methods for their preparation, will be readily apparent to those skilled in the art. Such compositions and methods for their preparation can be found, for example, in *Remington's Pharmaceutical Sciences,* 19th Edition (Mack Publishing Company, 1995).

Methods of Use

This document also provides methods and materials for using compounds that modulate (e.g., increase or decrease) the activity of mitochondrial Complex I and affect cellular energetics. Mitochondrial bioenergetics include the production of energy from nutrients in the form of glucose and fat, and are conducted in the mitochondrial matrix using enzymatic complexes of oxidative phosphorylation machinery (e.g., Complex I). Thus, via modulation of Complex I activity, cellular energetics as a whole can be modulated. For example, a compound as provided herein can decrease the activity of Complex I that results in decreased basal respiration of mitochondria, thus affecting bioenergetics. It is to be noted that decreasing the activity of Complex I also may improve recovery from ischemia or reperfusion, which can result in inflammation and oxidative damage through the induction of oxidative stress as blood returns to the tissue after a period of ischemia or lack of oxygen. Thus, the compounds and compositions described herein can provide cardioprotection from hypoxia/ischemia, and can be used to treat subjects identified as being in need of such cardioprotection.

In some cases, a compound as provided herein can be used to treat a disease or disorder that involves mitochondrial dysfunction. For example, mitochondrial motility can be restored in a patient by administering a therapeutically effective amount of a compound provided herein. In addition, mitochondrial function can be increased in a cell by contacting the cell with an effective amount of a compound provided herein.

Diseases and disorders that involve mitochondrial dysfunction include, for example, neurodegenerative diseases such as AD, HD, PD, various types of dementia (e.g., frontotemporal dementia), MS, amyotrophic lateral sclerosis (ALS), diabetes, metabolic syndrome, cancer, chemotherapy-induced peripheral neuropathies, and Down Syndrome, as well as aging. In some embodiments, the compounds provided herein also can promote healthy aging, and increase longevity and fecundity.

Compounds provided herein are effective to modulate mitochondrial function in a cell, for example, in a neural cell. Therefore, this document also provides a method of modulating (e.g., restoring) mitochondrial dynamics in a cell, comprising contacting the cell with an effective amount of a compound provided herein, or a pharmaceutically acceptable salt form thereof. The method can be performed by contacting the cell with a compound as described herein, or a pharmaceutically acceptable salt form thereof, in vitro, thereby modulating mitochondrial dynamics and function in vitro. Uses of such an in vitro method include, without limitation, use in a screening assay (e.g., wherein a compound described herein is used as a positive control or standard compared to compounds of unknown activity or potency in modulating mitochondrial function).

In the methods provided herein, any appropriate method can be used to administer a compound to a subject. Administration can be, for example, parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In some embodiments, administration can be topical (e.g., transdermal, sublingual, ophthalmic, or intranasal), pulmonary (e.g., by inhalation or insufflation of powders or aerosols), or oral.

A compound provided herein can be administered to a subject in an appropriate amount, at an appropriate frequency, and for an appropriate duration effective to achieve a desired outcome (e.g., to reduce one or more clinical symptoms or molecular/cellular hallmarks of a neurodegenerative disease such as AD, to protect or restore mitochondrial function in cells within a subject with the disease, or to reduce the likelihood of the disease or delay or prevent the onset of the disease in a subject at risk of developing the disease, such as a subject carrying a mutation in a PS1, PS2, or APP gene that is associated with AD, or carrying an ApoE4 allele that predisposes a subject to the development of AD). When the disease is AD, symptoms and hallmarks that can be reduced by treatment with a compound or composition as provided herein include, for example, cognitive decline, formation of extracellular A$\beta$ plaques and/or intracellular NFTs, and abnormal processing of APP. Thus, administration of an effective amount of a compound or composition as provided herein can result in improved cognitive function, reduced formation or numbers of A$\beta$ plaques and/or NFTs (e.g., reduced by at least about 5 percent, about 10 percent, about 25 percent, about 50 percent, about 75 percent, about 90 percent, or more than 90 percent, as compared to the formation or number of A$\beta$ plaques and/or NFTs in the subject prior to administration of the compound or composition, or in a control subject or population of subjects to whom the compound or composition was not administered), and/or reduced abnormal processing of APP in a subject. Any suitable method can be used to assess cognitive function/decline, A$\beta$ plaque formation or number, NFT formation or number, and APP processing in a subject. Such methods can include, without limitation, neuropsychological tests (e.g., question-and-answer tests or other tasks) that measure memory, language skills, ability to do arithmetic, and other abilities related to brain functioning; tests of blood and/or cerebrospinal fluid, or other medical tests to assess neurological functioning associated with dementia; computed tomography (CT) scan or magnetic resonance imaging (MRI) tests that can reveal changes in brain structure that indicate AD; other imaging techniques, such as positron emission tomography (PET) and single photon emission computed tomography (SPECT); PIB-PET imaging that can detect amyloid in the brain of a living patient; and emerging methods of diagnosis such as metabolic and epigenetic profiling.

Further, administration of an effective amount of a compound or composition as provided herein can result in enhanced ability to sustain oxidative damage or produce energy under stress conditions, and/or in restored mitochondrial dynamics in cells of a subject, where the mitochondrial function is increased by at least about 5% (e.g., about 25%, about 50%, about 75%, or more than about 75%). Mitochondrial function in cells of a subject can be assessed by, for example, evaluating levels of spare respiratory capacity, axonal motility, ATP production, coupling efficiency of respiratory chain, level of proton leak, Complex I activity, and/or $NAD^+/NADH$ ratios, using methods such as those described herein. In some embodiments, mitochondrial function can be assessed in peripheral cells (e.g., fibroblasts or lymphocytes) using methods described herein, including evaluation of Complex I-V activity, ATP production, and resistance to oxidative damage and stress. Parameters of mitochondrial energetics in cells from treated AD patients also can be evaluated using, e.g., a Seahorse Extracellular Flux Analyzer (see, Lange et al., *Frontiers Neurol,* 3:175, 2012). Mitochondrial function in AD patients also can be assessed using FDG-PET to monitor levels of glucose utilization in affected brain regions, and by measuring levels of mitochondrial metabolites using proton magnetic resonance (MR) spectroscopy such as lactate, N-acetyl aspartate (NAA), and mio-inositol. In addition, mitochondrial function can be assessed in blood, plasma, CSF, and/or peripheral cells/tissue by application of metabolomics profiling (see, e.g., Trushina et al., *PLOS ONE,* 8:e63644, 2013).

Optimum dosages of a compound or composition as provided herein can vary depending on the relative potency of individual compounds, and can generally be estimated based on $EC_{50}$ found to be effective in in vitro and in vivo animal models. Dosages may fall within the range from 0.5 mg to 500 mg. For example, an effective amount of a compound as provided herein can be from about 0.5 mg to about 1 mg, about 1 mg to about 5 mg, about 5 mg to about 10 mg, about 10 mg to about 25 mg, about 25 mg to about 50 mg, about 50 to about 100 mg, about 100 mg to about 250 mg, or about 250 mg to about 500 mg. If a particular subject fails to respond to a particular amount, then the amount of the compound or composition can be increased by, for example, two fold. After receiving this higher concentration, the subject can be monitored for both responsiveness to the treatment and toxicity symptoms, and adjustments made accordingly. The effective amount can remain constant or can be adjusted as a sliding scale or variable dose depending on the subject's response to treatment. Various factors can influence the actual effective amount used for a particular application. For example, the frequency of administration, duration of treatment, and severity of disease may require an increase or decrease in the actual effective amount administered.

The frequency of administration can be any frequency that has a desired effect (e.g., reducing one or more clinical symptoms or molecular/cellular hallmarks of AD, increasing or restoring mitochondrial function in cells within a subject with AD, or delaying or preventing the onset of AD in a subject at risk of AD), without producing significant toxicity. For example, the frequency of administration can be once or more daily, biweekly, weekly, monthly, or even less. The frequency of administration can remain constant or can be variable during the duration of treatment. A course of treatment can include rest periods. For example, a composition containing one or more compounds as provided herein can be administered over a two week period followed by a two week rest period, and such a regimen can be repeated multiple times. As with the effective amount, various factors can influence the actual frequency of administration used for a particular application. For example, the effective amount, duration of treatment, route of administration, and severity of disease may require an increase or decrease in administration frequency.

An effective duration for administering a compound provided herein can be any duration that has a desired effect (e.g., for AD, reducing one or more clinical symptoms or molecular/cellular hallmarks of AD, enhancing or restoring mitochondrial function in cells within a subject with AD, or delaying or preventing the onset of AD in a subject at risk of AD), without producing significant toxicity. Thus, an effective duration can vary from several days to several weeks, months, or years, but in general, an effective duration for treatment of AD can extend for number of years, such that an effective duration can be for as long as an individual subject is alive. Multiple factors can influence the actual effective duration used for a particular treatment. For example, an effective duration can vary with the frequency of administration, effective amount, use of multiple treatment agents, route of administration, and severity of the disease.

After administering a compound as provided herein to subject having or at risk for developing a disorder such as AD, the subject can be monitored to determine whether or not the disorder has been treated or prevented. For AD, for example, a subject can be assessed after treatment to determine whether or not a symptom of AD has been reduced, or whether any symptoms or hallmarks of AD have developed (e.g., in the case of a person at risk for developing AD). Methods for assessing symptoms and hallmarks of AD are described herein.

In some embodiments, an effective amount of a compound as described herein, or a composition containing a compound as described herein, can be any amount that reduces the severity, progression, or recurrence of cancer (e.g., pancreatic cancer, cervical cancer, or lymphoma) in a subject (e.g., a human or a non-human mammal), without producing significant toxicity to the subject. Effective doses can vary depending on the severity of the cancer, the route of administration, the age and general health condition of the subject, excipient usage, the possibility of co-usage with other therapeutic treatments, and the judgment of the treating physician. If a recipient fails to respond to a particular amount, then the amount of a compound or composition can be increased by, for example, two fold. After receiving this higher amount, the subject can be monitored for both responsiveness to the treatment and toxicity symptoms, and adjustments made accordingly. The effective amount can remain constant or can be adjusted as a sliding scale or variable dose depending on the response to treatment. Various factors can influence the actual effective amount used for a particular application. For example, the frequency of administration, duration of treatment, use of multiple treatment agents, route of administration, and severity of the cancer may require an increase or decrease in the actual effective amount administered.

The frequency of administration can be any frequency that reduces the severity, progression, or recurrence of cancer (e.g., pancreatic cancer, cervical cancer, or lymphoma) in a subject (e.g., a human or a non-human mammal) without producing significant toxicity to the subject. For example, the frequency of administration can be from about once a week to about three times a day. The frequency of administration can remain constant or can be variable during the duration of treatment. A course of treatment with a composition containing one or more of the compounds described herein can include rest periods. For example, a composition can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer may require an increase or decrease in administration frequency.

An effective duration for administering a composition containing one or more compounds as described herein can be any duration that reduces the severity, progression, or recurrence of cancer (e.g., pancreatic cancer, cervical cancer, or lymphoma) without producing significant toxicity to the recipient. Thus, the effective duration can vary from several days to several weeks, months, or years. In general, the effective duration for the treatment with one or more compounds as described herein to reduce the severity, progression, or recurrence of cancer (e.g., pancreatic cancer, cervical cancer, or lymphoma) can range in duration from one week to one year (e.g., one month to six months). Multiple factors can influence the actual effective duration used for a particular treatment. For example, an effective duration can vary with the frequency of administration, effective amount, use of multiple treatment agents, route of administration, and severity of the cancer being treated.

In some embodiments, a course of treatment and the severity of one or more symptoms related to the cancer being treated (e.g., pancreatic cancer, cervical cancer, or lymphoma) can be monitored. Any appropriate method can be used to determine whether or not the severity of a symptom is reduced. For example, the severity of a symptom of pancreatic cancer (e.g., cancer recurrence) can be assessed using imaging techniques.

Also provided herein are articles of manufacture containing one or more compounds as described herein, or a pharmaceutical composition containing one or more compounds as described herein, in combination with a pharmaceutically acceptable carrier, for example. The compound or composition can be within a container (e.g., a bottle, vial, or syringe). The article of manufacture also can include a label with directions for reconstituting and/or using the compound(s) or composition. In some embodiments, an article of manufacture can include one or more additional items (e.g., one or more buffers, diluents, filters, needles, syringes, and/or package inserts with further instructions for use).

The invention will be further described in the following examples, which do not limit the scope of the invention described in the claims.

EXAMPLE

Example 1—Identification of Small Molecule Compounds for Restoring Mitochondrial Function An array of 24 compounds was synthesized and purified. CP2 (FIG. 1), a tricyclic pyrone compound that protects against amyloid and mutant huntingtin toxicity in cellular and animals models of AD and HD (Trushina et al., *BMC Neurosci*, 10:73, 2009; Rana et al., *Bioorg Med Chem Lett*, 19:670-674, 2009; Maezawa et al., *J Neurochem*, 98:57-67, 2006; Hong et al., *J Neurochem*, 108(4):1097-1108, 2009 (published online 25 Dec. 2008); and Zhang et al., *eBioMedicine*, 2015), was synthesized as a TFA salt and free base to provide a reference compound for biological testing. All synthesized compounds were HPLC purified and had a final purity over 95%.

All 24 compounds were screened to test their toxicity and efficacy. Specifically, the toxicity of the compounds was evaluated in (1) the SK-N-MC cell line, a parental cell line for the Tet on/off MC65 cells, and (2) primary mouse cortical neurons. In addition, the efficiency of each compound (along with CP2) was evaluated against Aβ toxicity in MC65 cells, Tet on/off cells generated to express Aβ.

Example 2—Toxicity in SK-N-MC Neuroepithelioma Cells

Figure 2B:
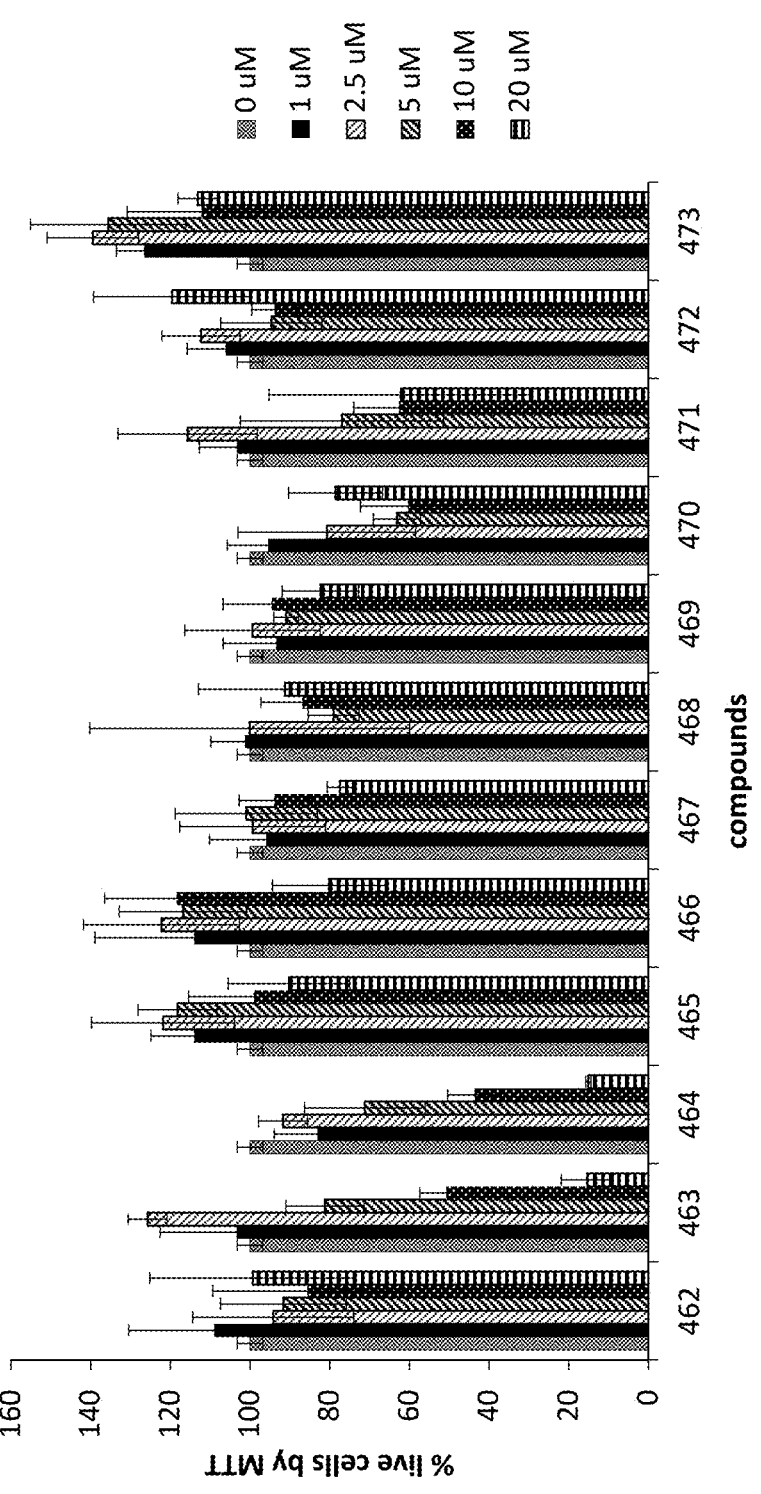

Toxicity of the 24 new compounds, CP2 free base, and CP2 TFA salt was evaluated in the SK-N-MC neuroepithelioma cell line. SK-N-MC is a parental cell line for MC65 cells that conditionally express Aβ and have been used previously to test the effect of CP2 against Aβ toxicity (Maezawa et al., *J Neurochem*, 98:57-67, 2006). SK-N-MC were treated at 1 µM, 2.5 µM, 5 µM, 10 µM and 20 µM with each compound or vehicle (DMSO 0.05%-water). Cell viability was measured using a 3-(4,5-dimethylthiazole-2-yl)-2,5-dyphenyltetrazolium bromide (MTT assay) after 48 hours. As shown in FIGS. 2A and 2B, most of the compounds did not cause toxicity at 1-20 except for compounds 463 and 464, where treatment with 10 µM resulted in 50% cell death. Compounds 452-454, 456-462, 470, and 471 became modestly toxic (—20%) in the range of 2.5 µM to 5 µM. Thus, this range of concentrations was selected for the rest of the screening studies.

Example 3—Toxicity in Primary Mouse Cortical Neurons

Figure 3A:
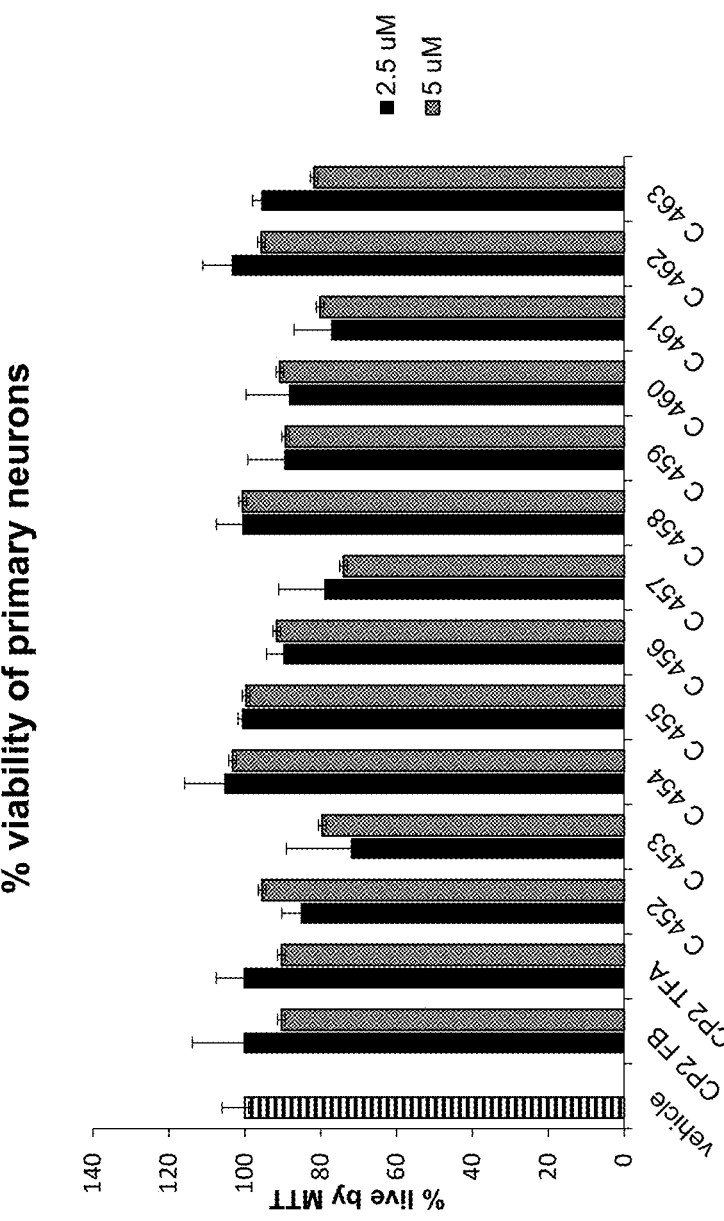
FIGS. 3A and 3B are a pair of graphs plotting survival of primary neurons after treatment with the indicated compounds. Primary embryonic cortical neurons were isolated as described elsewhere (Trushina et al., *Proc Natl Acad Sci USA*, 100:12171-12176, 2003) and seeded on 96-well plates at 30,000 cells per well. Seven days later, cells were treated with 2.5 μM and 5 μM of the indicated compounds (FIG. 3A, vehicle, CP2 free base, CP2 TFA salt, and C452-C463.
Figure 3B:
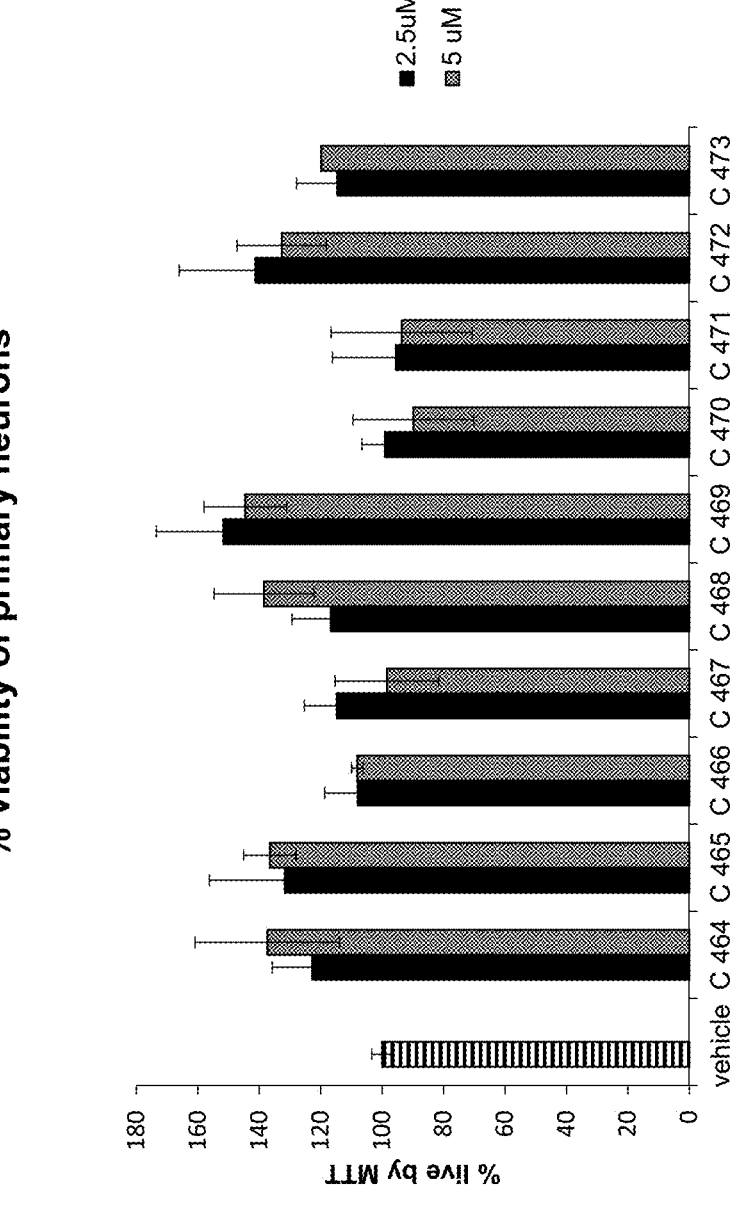
Figure 4A:
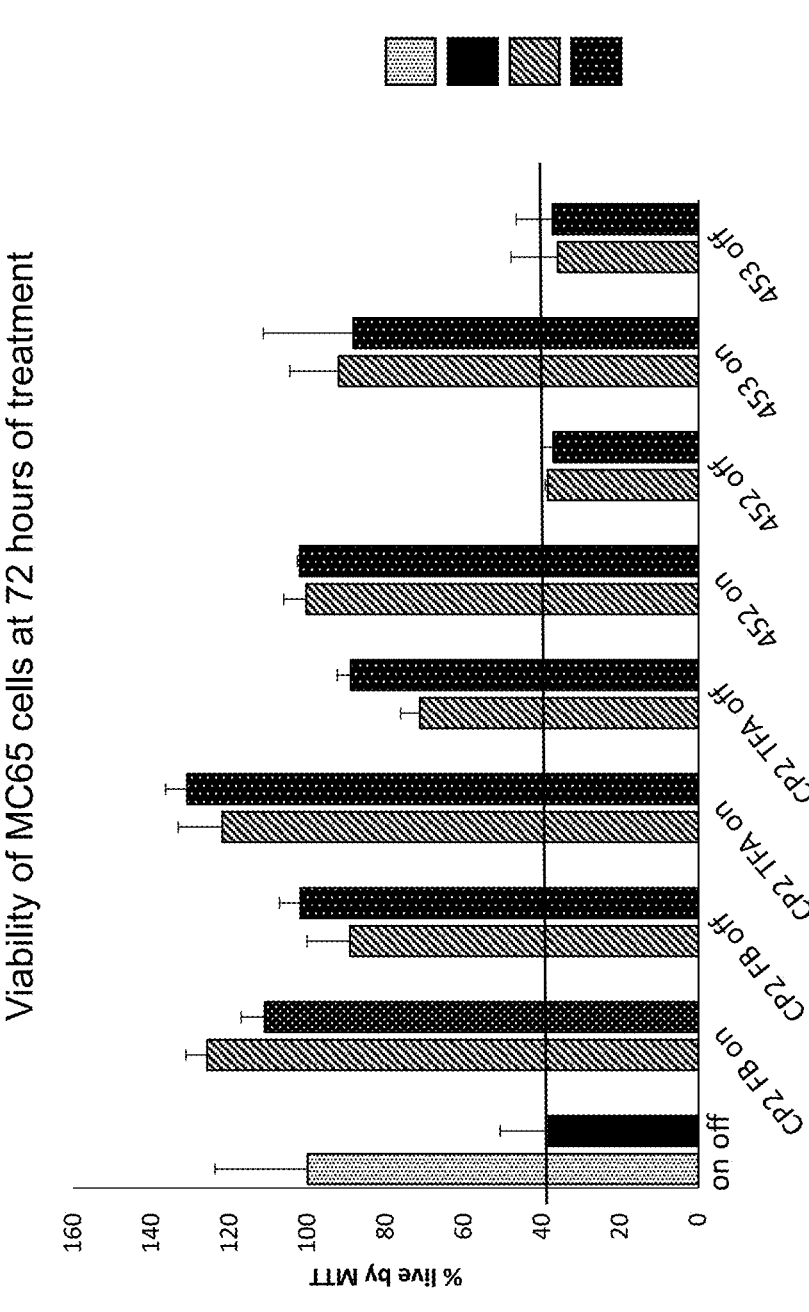
FIGS. 4A and 4B are a pair of graphs plotting survival of MC65 cells after treatment with the indicated compounds, in the presence (Tet/off) or absence (Tet/on) of Aβ expression. MC65 cells were cultured for 72 hours in the presence (on) or absence (off) of tetracycline in OPTI-MEM media without serum. Cells (Tet/on and Tet/off) at the time of plating were treated every 24 hours with vehicle (0.05% final DMSO) or experimental compounds (FIG. 4A, CP2 free base, CP2 TFA salt, C452, and C453.
Figure 4B:
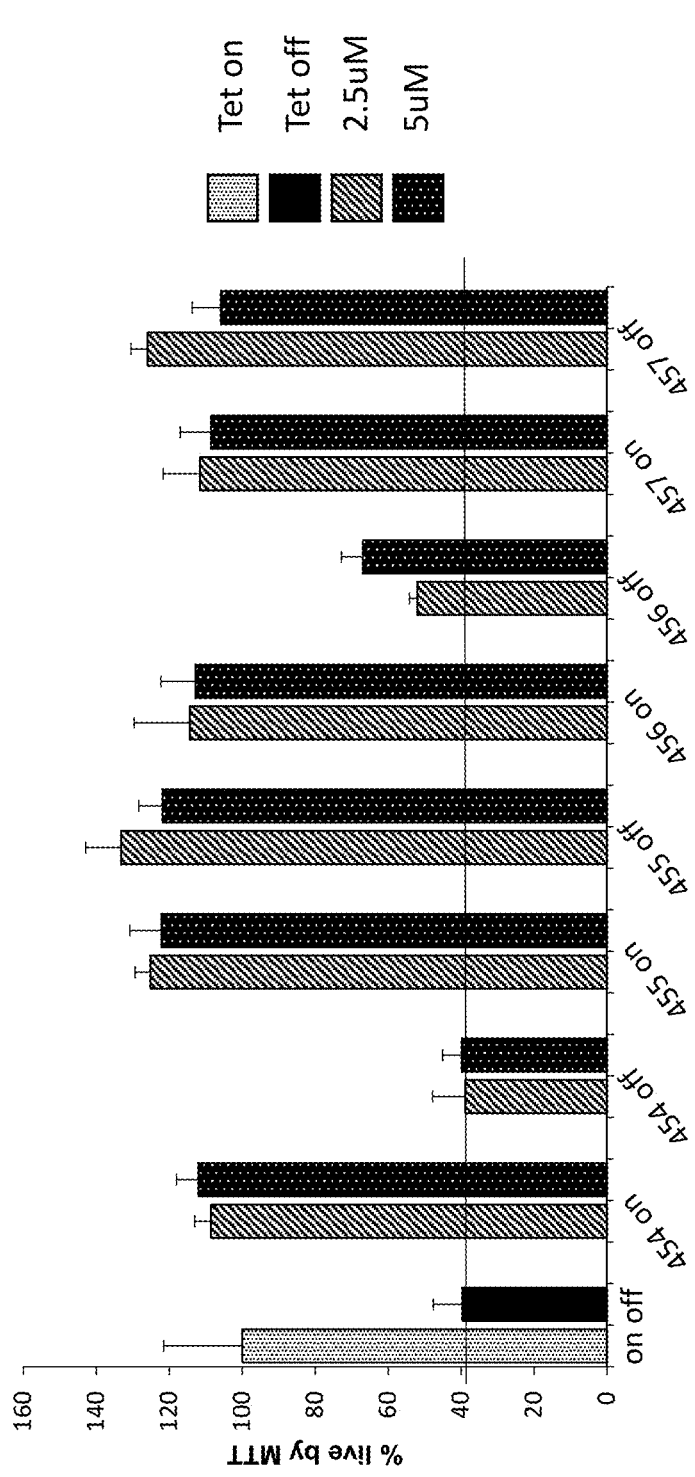
Figure 5B:
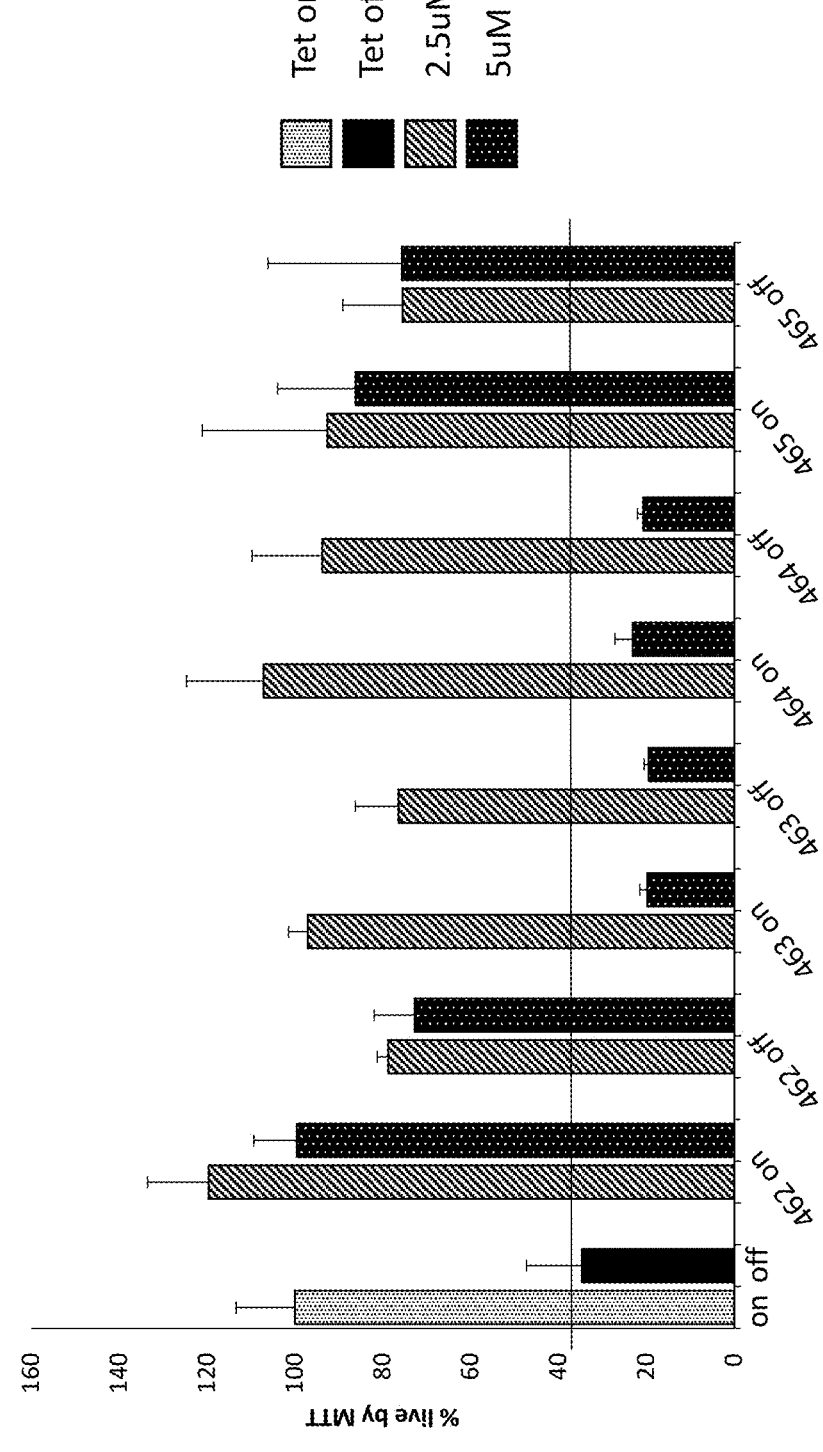
Figure 6B:
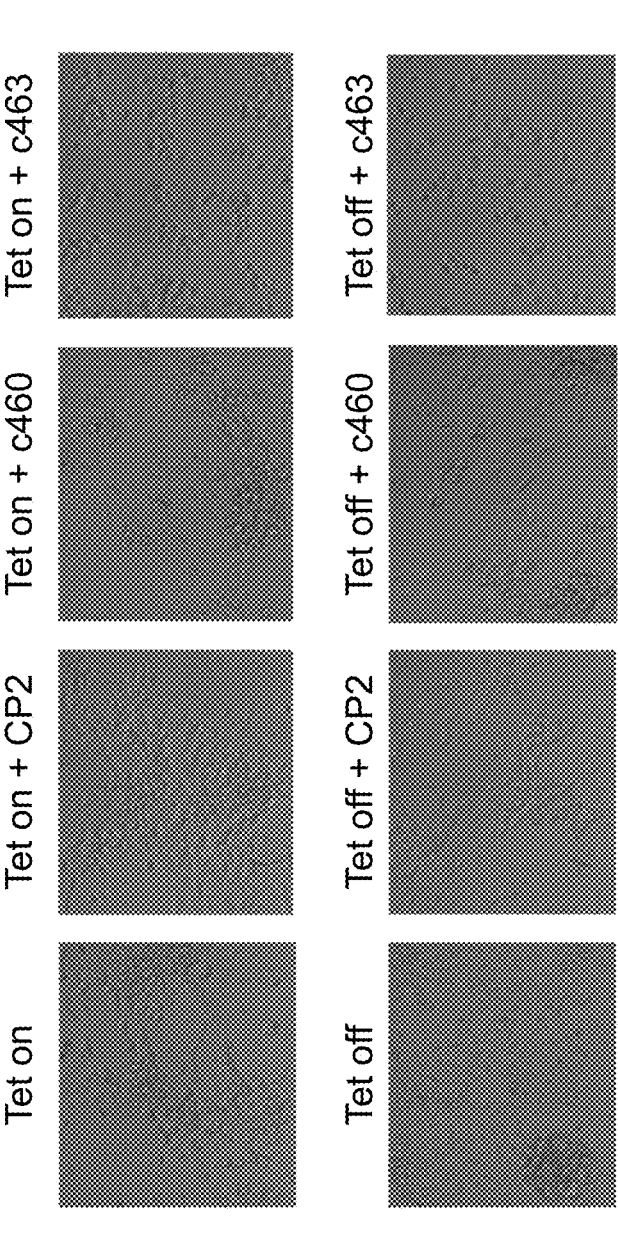
FIG. 6B is a series of representative images of MC65 cells after 72 hours in culture under Tet/on and Tet/off conditions, demonstrating efficacy of CP2 and C460 against Aβ toxicity. Toxicity of C463 under the same experimental conditions is shown for comparison. Cells were treated with 5 μM of each compound.

Toxicity of the 24 compounds, CP2 free base, and CP2 TFA salt was evaluated in primary mouse embryonic (E17) cortical neurons (FIGS. 3A and 3B). Most of the compounds were not toxic or had low (~20%) toxicity (C453, C457, C460 at concentrations of 2.5 µM to 5 µM.

Example 4—Efficacy of Novel Compounds Against Aβ Toxicity in MC65 Cell Line

The efficacy of all 24 compounds against Aβ toxicity was evaluated in MC65 cells. These cells are stably transfected with Aβ expression vector under tetracycline control, and were used to study CP2 properties against Aβ toxicity as described elsewhere (Maezawa et al., *J Neurochem*, 98:57-67, 2006). The viability of MC65 cells expressing Aβ (Tet/off, 40% viability) or not expressing Aβ (Tet/on, 100% viability) was measured after treatment with individual compounds. Results for all 24 compounds against Aβ toxicity are presented in FIGS. 4A, 4B, 5A, 5B, 6A, and 6B.

Figure 7:
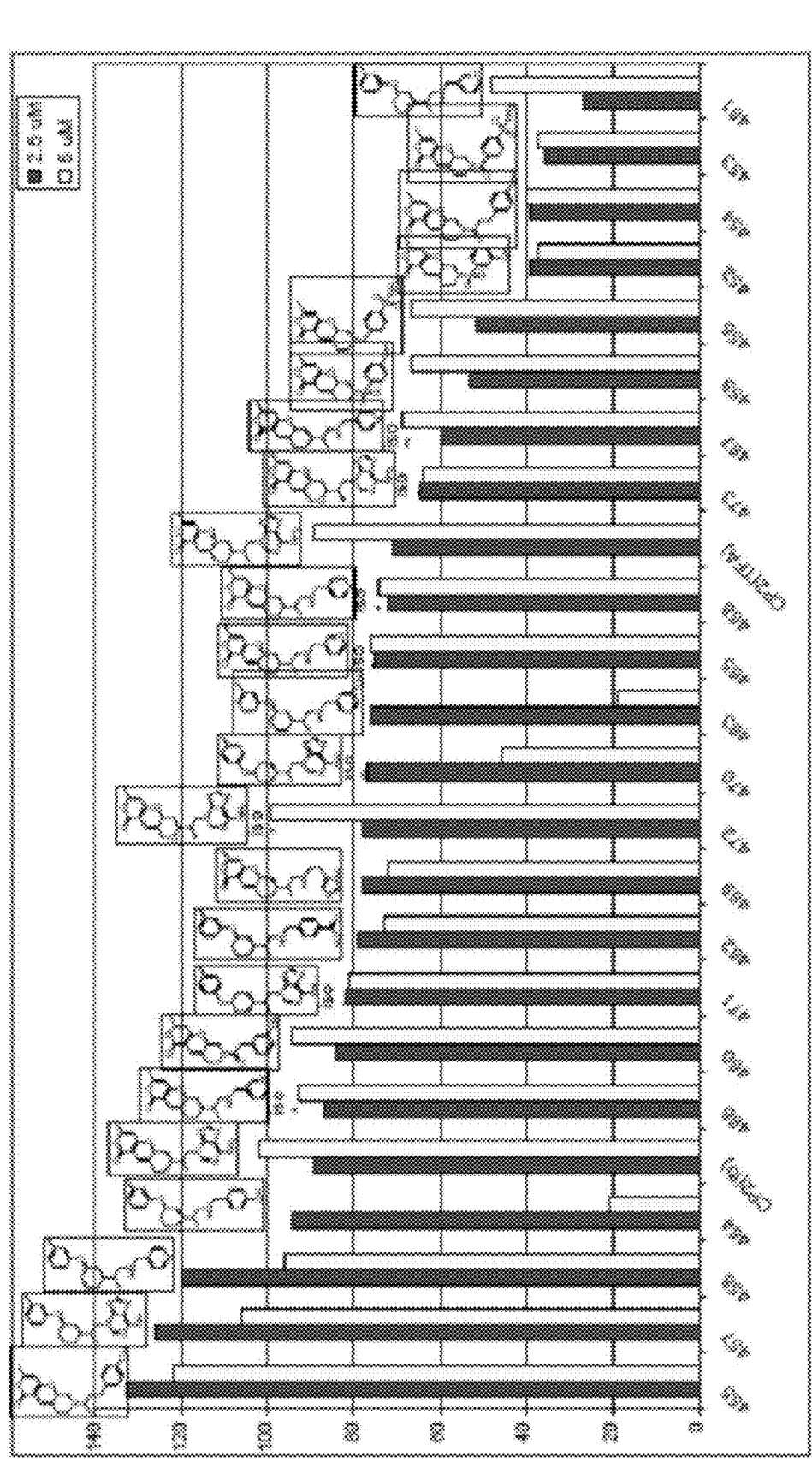
FIG. 7 is a graph plotting survival of Aβ-producing MC65 cells treated with each of the indicated compounds at 2.5 μM and 5 as compared to survival after treatment with CP2 free base or CP2 TFA salt.
Figure 8:
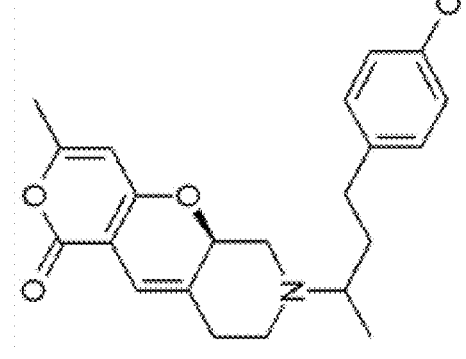
FIGS. 8A-8D show structures representing four classes of compounds that had promising cell-protective activity in Aβ-producing MC65 cells.
Figure 9:
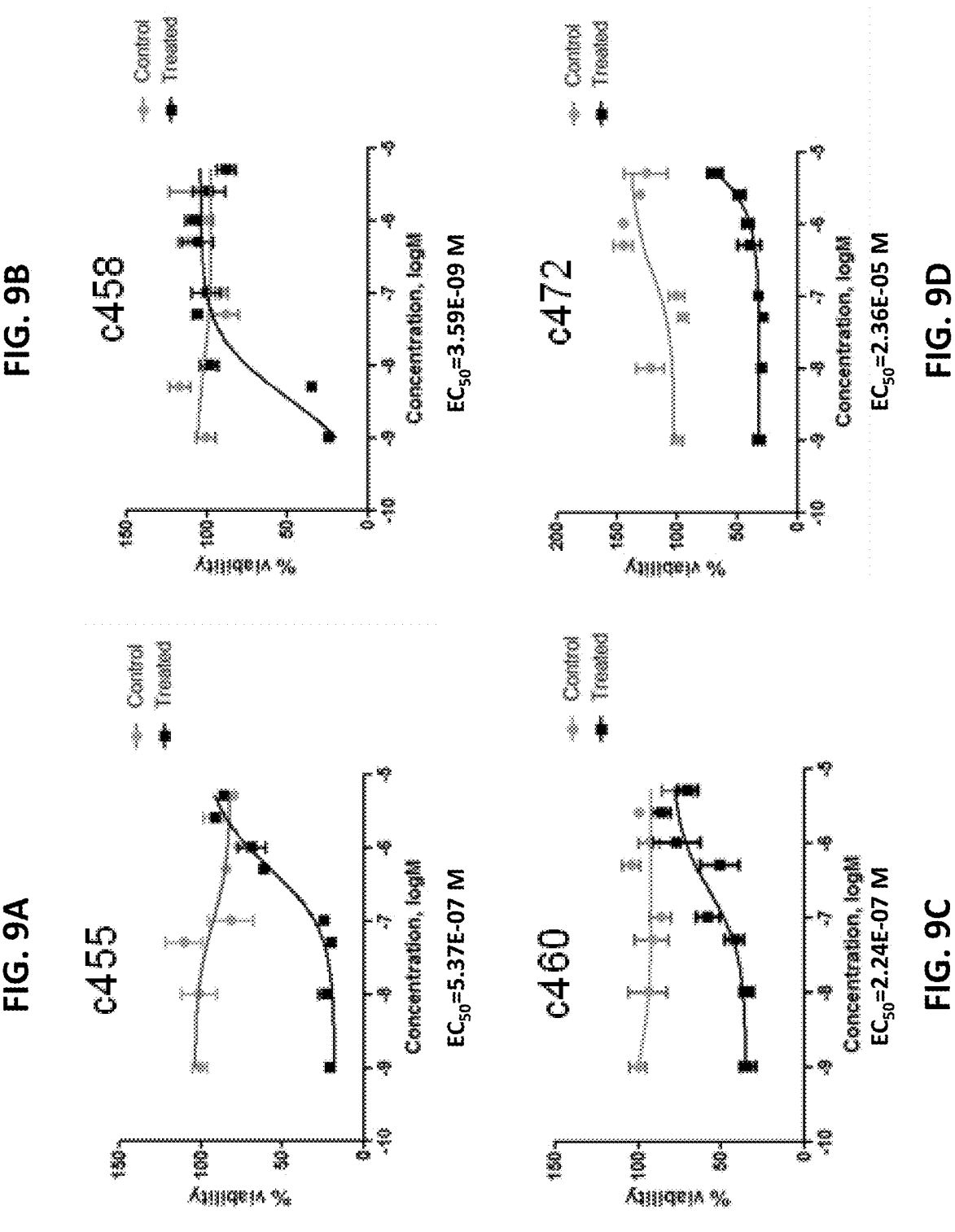
FIGS. 9A-9D are a series of graphs plotting the half maximal effective concentration ($EC_{50}$) for each of four experimental compounds against Aβ toxicity in MC65 Tet on/off cells.

The efficacy of all 24 compounds against Aβ toxicity was compared to that of CP2 free base and CP2 TFA salt (FIG. 7). These studies led to the identification of four compounds (FIGS. 8A-8D; C455, C458, C460, and C472, respectively) that had promising cell protective activity in Aβ-producing MC65 cells. Various properties of these four compounds are presented in TABLE 1. The four compounds were selected for further studies to assess mitochondrial function and dynamics in neurons.

TABLE 1

| Drug-like properties of hit molecules | | | | |
|---|---|---|---|---|
|  | C455 | C458 | C460 | C472 |
| Calculated log P | 3.1 | 4.4 | 0.81 | 0.3 |
| Calculated log $D_{7.4}$ | 2.0 | 2.0 | 0.2 | 0.3 |
| Total polar surface area | 62.9 | 34.2 | 92.0 | 118.3 |
| H-bond acceptors | 5 | 3 | 7 | 9 |

TABLE 1-continued

Drug-like properties of hit molecules

|  | C455 | C458 | C460 | C472 |
|---|---|---|---|---|
| H-bond donors | 1 | 1 | 2 | 2 |
| Molecular weight | 367.45 | 338.50 | 382.42 | 341.90 |

Example 5—Measurement of $EC_{50}$ for Four Selected Compounds

To further characterize the efficacy of these four compounds, the half maximal effective concentration ($EC_{50}$) against Aβ toxicity in MC65 cells was measured using an MTT assay. $EC_{50}$ values were calculated by fitting experimental data to calculated data for nonlinear regression using GraphPad Prizm5 software. The results are presented in FIGS. 9A-9D. Compound C458 demonstrated 100-fold higher efficacy than C455 and C460, and 20- to 30-fold higher efficacy than CP2, with $EC_{50}$ near 4 nM.

Example 6—Toxicity, Histology, and Pharmacokinetics (PK) of C458

The feasibility of developing the $C_{458}$ series was evaluated by determining the in vivo PK profile for C458. Re-synthesized C458 was administered intravenously to wild type mice at 2 mg/kg. Frozen serum and brain tissue samples were analyzed using a bioanalytical LC-MS/MS method. The resulting PK data showed that the compound persisted in the blood with an apparent $t_{1/2}$ of 48 min (TABLE 2). Further, the compound showed significant CNS penetration, as evidenced concentrations in the brain tissue that were 7-10 times higher (w/v) than in plasma.

Treatment of wild type (WT) mice with C458 (50 mg/kg for one month ad libitum in drinking water) did not cause histological abnormalities in animals. As noted above, C458 demonstrated the highest efficacy against Aβ toxicity in an MC65 cell-based assay, with $EC_{50}$=3.59 nM (30-fold lower than CP2, which had an $EC_{50}$=120 nM). To evaluate the toxicity of C458 in vivo, 2-month old breeding WT mice were treated with 50 mg/kg of C458 via drinking water. Untreated littermates were used as controls. After one month of treatment, adult and newborn animals were sacrificed and tissue was collected for histological examination. Histology results demonstrated lack of any developmental or tissue pathology, as organs of C458-treated mice were indistinguishable from those of untreated animals. Similarly, no pathological abnormalities were detected in newborn mice conceived by breeding WT mice treated with C458 (50 mg/kg for one month ad libitum in drinking water).

Example 7—Elimination Rate and Half-Life of C458 in Plasma and Brain Tissue

The elimination rate and half-life of C458, measured in plasma and brain, demonstrated good bioavailability of C458, and again suggested that C458 penetrates the blood brain barrier. A rough estimation of elimination rate and half-life of C458 was determined in vivo by delivering a dose of 2.5 mg/kg to each mouse via intrafemoral vein injection. Each group of animals (n=2) was sacrificed at 30 minutes, 1 hour, and 2 hours post injection. Blood and brain tissue was collected, flash frozen, and the concentration of C458 was estimated using a LC-MS/MS assay with a linear calibration curve from 1 ng/ml to 1 ug/ml in both plasma and brain. The concentration of C458 in the brain was 7-8 times higher than in plasma, suggesting that C458 penetrates the blood brain barrier and accumulates in the brain.

Figure 10:
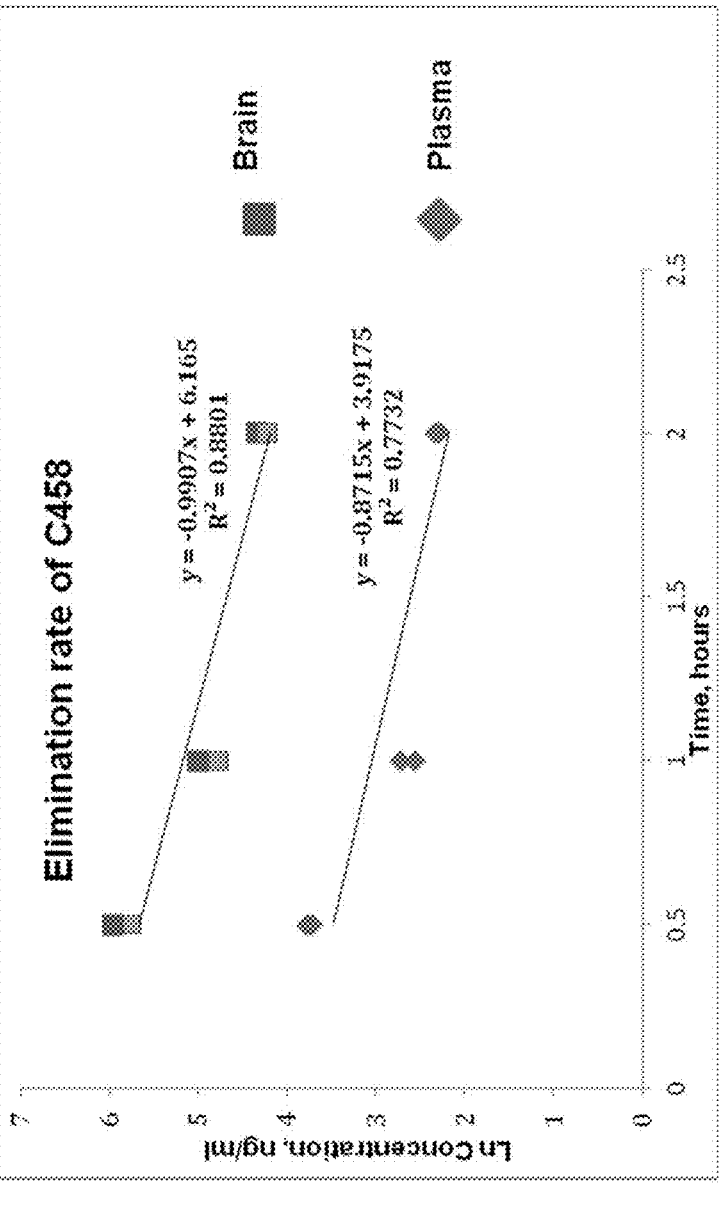
FIG. 10 is a graph plotting the elimination rate for C458 in brain and plasma of mice treated with 2.5 mg/kg of the compound via intrafemoral vein injection. Animals were sacrificed at 30 minutes, 1 hour, and 2 hours post injection.

For rough estimation of elimination rate and half-life, a one-compartment model and the first rate elimination was assumed. Plotting (Ln) of concentration vs. time provided the elimination rate and half-life of C458 in plasma and the brain (FIG. 10). The estimated half-life of C458 for the first rate elimination (defined as $t_{1/2}$=ln 2/k) in plasma and brain was 48 minutes and 42 minutes, respectively.

TABLE 2

PK data for C458

| Sample ID | Mouse ID | Time (hr.) | Plasma Concentration (ng/mL) | Brain Concentration (ng/g) |
|---|---|---|---|---|
| 0001 | WT 116 | 0.5 | 43.7 | 316 |
| 0002 | WT 121 | 0.5 | 41.4 | 390 |
| 0003 | WT 130 | 1 | 15.2 | 149 |
| 0004 | WT 131 | 1 | 13.0 | 118 |
| 0005 | WT 145 | 2 | 9.83 | 68.2 |
| 0006 | WT 156 | 2 | 10.3 | 76.4 |

Example 8—Expansion of the C458 Series

An array of 23 compounds as synthesized and purified (TABLE 3). Compound C458 was re-synthesized as both the TFA and HCl salt to provide a reference compound. All synthesized compounds were HPLC purified and had a final purity over 95%.

TABLE 3

C458 series compounds

| Structure | % Purity | MW (free base) | FW(salt) | salt | Comments |
|---|---|---|---|---|---|
| 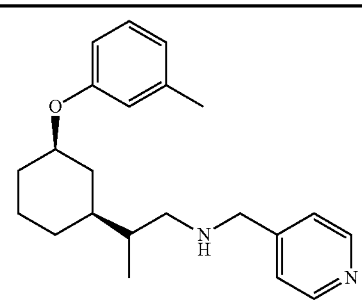 | 99.5 | 338.50 | 452.52 | TFA | Highly hygroscopic |

TABLE 3-continued

| C458 series compounds | | | | | |
|---|---|---|---|---|---|
| Structure | % Purity | MW (free base) | FW(salt) | salt | Comments |
| | 100.0 | 338.50 | 374.96 | HCl | HCl form of control compound |
| | 76.9 | 351.54 | 388.00 | HCl | Control compound for PK |
| | 99.9 | 338.50 | 374.96 | HCl | Sent for PK |
| | 100.0 | 338.50 | 374.96 | HCl | |
| | 97.6 | 324.47 | 360.93 | HCl | One less $CH_2$ |

TABLE 3-continued

C458 series compounds

| Structure | % Purity | MW (free base) | FW(salt) | salt | Comments |
|---|---|---|---|---|---|
| | 100.0 | 343.56 | 380.02 | HCl | Non-aromatic |
| 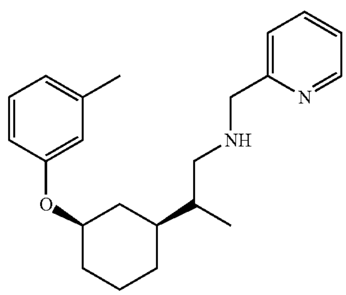 [SMILES: Cc1cccc(O[C@@H]2CCC[C@H](C(C)CNCc3ccccn3)C2)c1] | 96.7 | 338.50 | 338.50 | HCl | 2-pyridyl isomer |
| | 100.0 | 371.95 | 371.95 | HCl | |
| 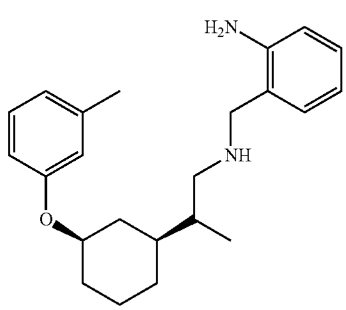 [SMILES: Cc1cccc(O[C@@H]2CCC[C@H](C(C)CNCc3ccccc3N)C2)c1] | 98.5 | 352.52 | 388.98 | HCl | |
| 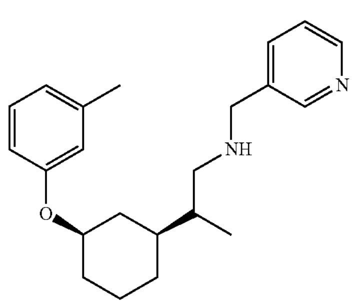 [SMILES: Cc1cccc(O[C@@H]2CCC[C@H](C(C)CNCc3cccnc3)C2)c1] | 99.7 | 338.50 | 374.96 | HCl | |

TABLE 3-continued

C458 series compounds

| Structure | % Purity | MW (free base) | FW(salt) | salt | Comments |
|---|---|---|---|---|---|
| (2-Cl-benzyl structure) | 100.0 | 371.95 | 408.41 | HCl | |
| (3-NH2-benzyl structure) | 98.1 | 352.52 | 388.98 | HCl | |
| (4-Cl-benzyl structure) | 100.0 | 371.95 | 408.41 | HCl | |
| (4-Cl-benzyl N-methyl structure) | 98.6 | 385.98 | 422.44 | HCl | |
| (2-HO-benzyl structure) | 100.0 | 353.51 | 389.97 | HCl | |

TABLE 3-continued

C458 series compounds

| Structure | % Purity | MW (free base) | FW(salt) | salt | Comments |
|---|---|---|---|---|---|
| 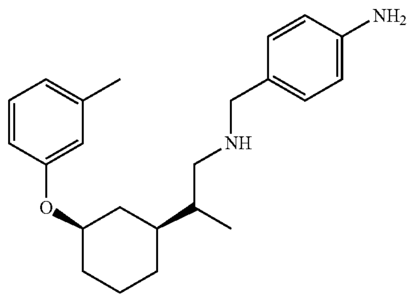 [SMILES: Cc1cccc(O[C@@H]2CCC[C@H](C(C)CNCc3ccc(N)cc3)C2)c1] | 98.6 | 352.52 | 388.98 | HCl | Aniline version |
| 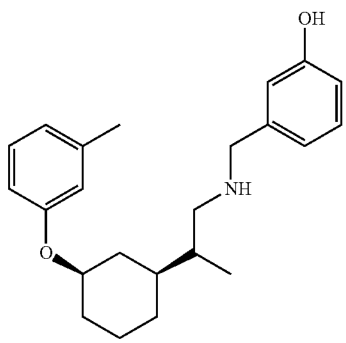 [SMILES: Cc1cccc(O[C@@H]2CCC[C@H](C(C)CNCc3cccc(O)c3)C2)c1] | 99.1 | 353.51 | 389.97 | HCl | |
| 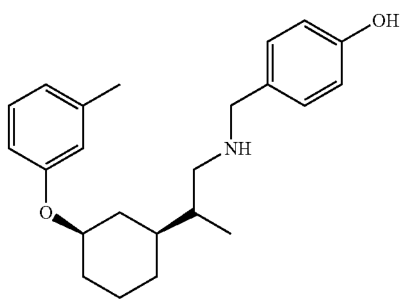 [SMILES: Cc1cccc(O[C@@H]2CCC[C@H](C(C)CNCc3ccc(O)cc3)C2)c1] | 98.8 | 353.51 | 389.97 | HCl | |
| 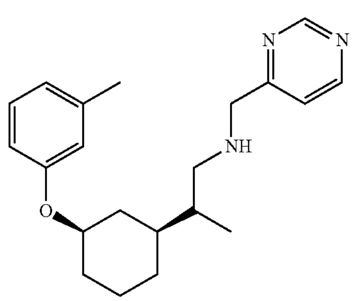 [SMILES: Cc1cccc(O[C@@H]2CCC[C@H](C(C)CNCc3ccncn3)C2)c1] | 97.8 | 339.48 | 375.94 | HCl | Adjust pKB |
| 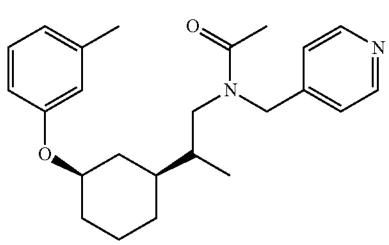 [SMILES: CC(=O)N(Cc1ccncc1)CC(C)[C@H]1CCC[C@@H](Oc2cccc(C)c2)C1] | 100.0 | 380.53 | 416.99 | HCl | |

TABLE 3-continued

C458 series compounds

| Structure | % Purity | MW (free base) | FW(salt) | salt | Comments |
|---|---|---|---|---|---|
| 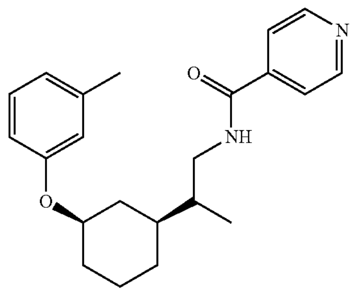 [SMILES: Cc1cccc(O[C@@H]2CCC[C@H](C(C)CNC(=O)c3ccncc3)C2)c1] | 96.5 | 352.48 | 388.94 | HCl | Non-basic N |
| 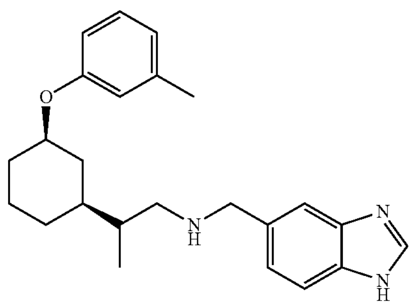 [SMILES: Cc1cccc(O[C@@H]2CCC[C@H](C(C)CNCc3ccc4[nH]cnc4c3)C2)c1] | 99.0 | 377.53 | 413.99 | HCl | Fused ring |

Example 9—Preparation of Starting Material—cis-(2-(3-(m-tolyloxy)cyclohexyl)propan-1-ol)

Step 1: Preparation of prop-1-en-2-ylmagnesium Bromide

Magnesium turnings (6.2 g, 252.6 mmol, 1.05 equiv.) were suspended in dry tetrahydrofuran (500 mL) in a one liter flask fitted with a magnetic stirring bar and an $N_2$ inlet. Isopropenyl bromide (5 mL, 57.2 mmol, 0.24 equiv.) and a small iodine crystal (~1 mm dia.) were added and the mixture was heated to 60° C. The reaction initiated in about fifteen minutes: the heating bath was then turned off and more isopropenyl bromide (16 mL, 182.9 mmol, 0.76 equiv.) was added in 4 mL portions. The vigorous reaction was allowed to subside in between additions. The resulting pale yellow solution of prop-1-en-2-ylmagnesium bromide was allowed to cool to room temperature and used in the next step. The theoretical concentration of the solution is 0.48M. Only a trace of undissolved magnesium remained.

Step 2—Preparation of 3-(prop-1-en-2-yl)cyclohexan-1-one

Copper iodide (11.4 g, 60.0 mmol, 0.6 equiv) was slurried in 750 mL dry tetrahydrofuran and chilled in a dry ice-acetone bath. Compound II (0.48M in tetrahydrofuran, 250 mL, 120 mmol, 1.2 equiv) was added dropwise over the course of one hour to the copper iodide slurry while the temperature was kept below −70° C. during the addition. Cyclohexen-1-one (9.6 g, 100.0 mmol, 1.0 equiv) and chlorotrimethylsilane (15.2 mL, 120.0 mmol, 1.2 equiv) were dissolved in 50 mL dry tetrahydrofuran. The resulting solution was added dropwise over the course of 45 minutes to the chilled alkyl copper slurry. The mixture was stirred for an additional fifteen minutes at which time TLC (30% ethyl acetate/hexane) revealed a mixture of desired product, some unreacted cyclohexen-1-one, and two minor side products.

The reaction was quenched with 250 mL of saturated ammonium chloride solution. The cold bath was then removed and the slurry was allowed to warm to approx. 5 C and was poured into a mixture of 50 mL 30% ammonium hydroxide dissolved in 2.5 L of water. The mixture was extracted with 3×1 L ethyl acetate and the aqueous phase discarded. The combined organic phases were washed with 2×1 L brine then the aqueous phases were discarded. The organic phase was concentrated to approx. 200 mL under reduced pressure, diluted to approx. 1 L with diethyl ether then dried over sodium sulfate. The solids were removed by filtration and discarded and the mother liquor was concentrated to obtain an orange oil that was purified using a CombiFlash (330 g column, 0-10% ethyl acetate/hexane) to obtain Compound III as a pale yellow oil. Yield: 6.6 g (48% from II).

Step 3—Preparation of cis-3-(prop-1-en-2-yl)cyclohexan-1-ol IV

Compound III (11.8 g, 85.4 mmol, 1.0 equiv.) was dissolved in 300 mL of tetrahydrofuran. Sodium borohydride (9.7 g, 256.1 mmol, 3.0 equiv) was added and the resulting mixture was stirred at room temperature and the reaction was determined to be complete after two hours by TLC (30% ethyl acetate/hexane). The reaction was quenched with a minimal amount of 3M aqueous hydrochloric acid until the pH was approx. 2. The solids were filtered and discarded and the mother liquor was concentrated to an oil using a rotary evaporator (25 mm Hg, bath temperature 20° C.). The oil was diluted with 500 mL diethyl ether and dried over sodium sulfate: the solids were removed by filtration and discarded and the mother liquor was concentrated to obtain a yellow oil. The material was combined with a previous batch (14 g scale) and purified using a CombiFlash (330 g column, 0-20% ethyl acetate/hexane) to obtain Compound IV as a pale yellow oil. Yield: 13.6 g cis isomer and 1.5 g trans isomer (58% from III).

Step 4—Preparation of Compound trans-3-(prop-1-en-2-yl)cyclohexyl 4-nitrobenzoate V Note: this procedure was carried out with 9.5 g of Compound IV, split into two 4.75 g batches that were run in parallel.

Compound IV (4.75 g, 33.9 mmol, 1.0 equiv.), was dissolved in 250 mL tetrahydrofuran, followed by 4-nitrobenzoic acid (22.6 g, 135.5 mmol, 4.0 equiv) and triphenylphosphine (35.5 g, 135.5 mmol, 4.0 equiv). The resulting solution was chilled in an ice water bath, after which N,N'-diisopropylazodicarboxylate (26.7 mL, 135.5 mmol, 4.0 equiv) was added in small portions over a one hour period, taking care to keep the temperature below 10° C. during the addition. The ice bath was removed and the reaction was stirred for fifteen hours at room temperature, then at 40° C. for three hours. After cooling to room temperature, the reaction was diluted with 250 mL diethyl ether and extracted with 2×150 mL saturated sodium bicarbonate solution. The combined aqueous phases were back extracted with 150 mL diethyl ether: the aqueous phase was discarded and the combined organics were dried over sodium sulfate and concentrated to obtain a yellow semi-solid. At this point the material from both batches was combined and was suspended in 100 mL diethyl ether and allowed to stand overnight. The resulting slurry was diluted with 50 mL diethyl ether and 150 mL hexane, and the solids were removed by filtration and discarded. The mother liquor was concentrated to obtain yellow oil that was split into three portions and purified by CombiFlash (330 g column, 0-15% ethyl acetate/hexane) to obtain 17.4 g pale yellow solid (Compound V). Yield: 89%.

Step 5—Preparation of Compound trans-3-(prop-1-en-2-yl)cyclohexan-1-ol VI

Compound V (17.4 g, 60.1 mmol, 1.0 equiv.) was dissolved in 200 mL of tetrahydrofuran. A solution of lithium hydroxide (8.7 g, dissolved in 125 mL of water) was added, and the resulting solution was stirred at room temperature. The mixture was stirred for fifteen hours and determined to be complete by TLC. The reaction mixture was partitioned between ether and water and the aqueous phase extracted twice with ether. The combined organics were dried over sodium sulfate and concentrated under reduced pressure to afford a yellow oil, which was dissolved in 50 mL of dichloromethane and filtered through a 1 cm deep silica gel pad. The pad was rinsed with a little additional dichloromethane, and the combined organics were concentrated to dryness to obtain a pale yellow oil that was purified by CombiFlash (120 g column, 0-20% ethyl acetate/hexane, 1 hr) to obtain 6.7 g Compound VI as a colorless oil. Yield: (79%).

Step 6—Preparation of cis-1-(3-tolyloxy)-3-isopropenyl-cyclohexane VII

Compound IV (4.75 g, 33.9 mmol, 1.0 equiv), was dissolved in 250 mL tetrahydrofuran, followed by m-cresol (14.2 mL, 135.5 mmol, 4.0 equiv) and 35.5 g triphenylphosphine (135.5 mmol, 4.0 equiv). The resulting solution was chilled in an ice water bath, and then N,N'-diisopropylazodicarboxylate (26.7 mL, 135.5 mmol, 4.0 equiv) was added in small portions over a one hour period, taking care to keep the temperature below 10° C. during the addition. The ice bath was removed and the reaction was stirred for fifteen hours at room temperature, then at 40° C. for three hours. After cooling to room temperature, the reaction was diluted with 250 mL diethyl ether and extracted with 2×150 mL saturated sodium bicarbonate solution. The combined aqueous phases were back extracted with 150 mL diethyl ether: the aqueous phase was discarded and the combined organics were dried over sodium sulfate. The solids were filtered and discarded, and the mother liquor was concentrated to obtain orange oil, which was dissolved in 150 mL of 1:1 diethyl ether/hexane stirred at room temperature for one hour. The solids were removed by filtration and discarded. The mother liquor was concentrated to obtain an orange oil that was purified by CombiFlash (330 g column, 0-10% ethyl acetate/hexane) to obtain 5.7 g pale oil (Compound VII). Yield: 73%.

Step 7—Preparation of cis-1-(3-methylphenyl)-3-(1-hydroxyprop-2-yl)cyclohexane VIII Note: this procedure was carried out with 5.7 g of Compound VII, split into three 1.9 g batches that were run in parallel.

Compound VII (1.9 g, 8.2 mmol, 1.0 eq.) was dissolved in 8.5 mL of dry tetrahydrofuran. The solution was chilled in an ice water bath, and then borane-dimethyl sulfide complex ([2.0M] in tetrahydrofuran, 4.1 mL, 8.2 mmol, 1.0 equiv) was added dropwise over a 25 minute period. The resulting mixture was stirred in the ice water bath for three hours, then aqueous sodium hydroxide solution (3M, 3.3 mL, 9.9 mmol, 1.2 equiv) was added dropwise over a fifteen minute period. Aqueous hydrogen peroxide (35 wt. %, 2.4 mL, 29.5 mmol, 3.6 equiv) was added over a five minute period, then the ice bath was removed and the resulting mixture was stirred at room temperature. TLC (20% ethyl acetate/hexane) in fifteen minutes showed starting material was consumed. The reaction was quenched with 1M aqueous hydrochloric acid, extracted with 3×25 mL diethyl ether. The combine organics were dried over sodium sulfate: the solids were removed by filtration and discarded; the mother liquor was concentrated to oil and purified by CombiFlash (80 g column, 0-30% ethyl acetate/hexane) to obtain 5.4 g of a clear oil (Compound VIII). Yield: 75%.

Step 8—Preparation of cis-2-(-3-(m-tolyloxy)cyclohexyl)propanal IX

Compound VIII (50 mg, 0.2 mmol, and 1.0 equiv) was dissolved in 0.75 mL dichloromethane: the resulting solution was chilled in an ice water bath and Dess-Martin periodinane (111 mg, 0.26 mmol, 1.3 equiv) was added and the mixture stirred in the ice water bath for two hours. TLC (20% ethyl acetate/hexane) showed reaction nearly complete. The mixture was stirred at room temperature for 30 minutes, quenched with 1 mL sodium thiosulfate solution and then extracted with 2×2 mL ethyl acetate. The combined organics were extracted with 2 mL of saturated sodium bicarbonate: the phases were separated and the aqueous phase was back extracted with 4 mL of ethyl acetate. The combined organics were dried over sodium sulfate and the solids were removed by filtration and discarded. The mother liquor was concentrated on a rotary evaporator to obtain 50 mg of a yellow oil (Compound IX). The crude material was used without further purification in the next step (Example 9).

Step 8a. Preparation of cis-2-(3-(3-(methoxy)phenoxy)cyclohexyl)propanal

Using the same procedures as described in Steps 6, 7 and 8, but with the substitution of m-methoxyphenol in place of m-cresol in Step 6, cis-2-(3-(3-(methoxy)phenoxy)cyclohexyl)propanal was prepared.

Step 8b Preparation of cis-2-(3-(3-(trifluoromethyl)phenoxy)cyclohexyl)propanal Using the same procedure as described in Steps 6, 7, and 8, but with the substitution of m-trifluoromethoxyphenol in place of m-cresol in Step 6, cis-2-(3-(3-(trifluoromethyl)phenoxy)cyclohexyl)propanal was prepared.

Example 9a—Preparation of cis-(N-(pyridin-4-ylmethyl)-2-(3-(m-tolyloxy)cyclohexyl)propan-1-amine)

Cis-2-(-3-(m-tolyloxy)cyclohexyl)propanal (82 mg, 0.33 mmol) was dissolved in anhydrous THF (3 mL). To this solution was added 4-(aminomethyl)pyridine (51 μL, 0.5 mmol) followed by titanium tetraisopropoxide (202 μL, 0.67 mmol). The mixture was stirred at room temperature for 45 min and then cooled in an ice bath. Sodium triacetoxyborohydride (212 mg, 1 mmol) was added and the ice bath was removed. After 45 minutes at room temperature, LC/MS analysis showed the reaction to be complete. The reaction was quenched with 1 M HCl and most of the solvent was removed under reduced pressure. The residue was dissolved in DMSO (1 mL) and purified by HPLC to afford the title product (LC/MS=339.2 [M+H]$^+$).

Example 9b—Alternate Preparation of cis-(N-(pyridin-4-ylmethyl)-2-(3-(m-tolyloxy)cyclohexyl)propan-1-amine)

Cis-2-(-3-(m-tolyloxy)cyclohexyl)propanal (82 mg, 0.33 mmol) was dissolved in anhydrous dichloroethane (3 mL).

To this solution was added 4-(aminomethyl)pyridine (51 μL, 0.5 mmole) and the mixture was stirred at room temperature for 45 min after which sodium triacetoxyborohydride (212 mg, 1 mmol) was added and reaction mixture brought to reflux. After 45 minutes, LC/MS analysis showed the reaction to be complete. The reaction was quenched with 1 M HCl and most of the solvent was removed under reduced pressure. The residue was dissolved in DMSO (1 mL) and purified by HPLC to afford the title product (LC/MS=339.2 [M+H]$^+$).

Example 10—Preparation of cis-N-(4-methylbenzyl)-2-(3-(m-tolyloxy)cyclohexyl)propan-1-amine Using the same procedure described in Example 9, step 2 using p-tolylmethanamine in place of 4-(aminomethyl)pyridine, cis-N-(4-methylbenzyl)-2-(3-(m-tolyloxy)cyclohexyl)propan-1-amine was prepared analogously (LC/MS=352.2 [M+H]$^+$).

Example 11—Preparation of cis-N-(2-(3-(m-tolyloxy)cyclohexyl)propyl)pyridin-4-amine Using the same procedure described in Example 9, using pyridin-4-amine in place of 4-(aminomethyl)pyridine, cis-N-(2-(3-(m-tolyloxy)cyclohexyl)propyl)pyridin-4-amine was prepared analogously (LC/MS=325.2 [M+H]$^+$).

Example 12—Preparation of cis-N-(cyclohexylmethyl)-2-(3-(m-tolyloxy)cyclohexyl)propan-1-amine Using the same procedure described in Example 9, using cyclohexylmethanamine in place of 4-(aminomethyl)pyridine, cis-N-(cyclohexylmethyl)-2-(3-(m-tolyloxy)-cyclohexyl)propan-1-amine was prepared analogously (LC/MS=344.2 [M+H]$^+$).

Example 13—Preparation of cis-N-(pyridin-2-ylmethyl)-2-(3-(m-tolyloxy)cyclohexyl)propan-1-amine Using the same procedure described in Example 9, using pyridin-2-ylmethanamine in place of 4-(aminomethyl)pyridine, cis-N-(pyridin-2-ylmethyl)-2-(3-(m-tolyloxy)cyclohexyl)propan-1-amine was prepared analogously (LC/MS=339.2 [M+H]$^+$).

Example 14—Preparation of cis-N-(3-chlorobenzyl)-2-(3-(m-tolyloxy)cyclohexyl)propan-1-amine Using the same procedure described in Example 9, using (3-chlorophenyl) methanamine in place of 4-(aminomethyl)

pyridine, cis-N-(3-chlorobenzyl)-2-(3-(m-tolyloxy)cyclohexyl)propan-1-amine was prepared analogously (LC/MS=372.2 [M+H]$^+$).

Example 15—Preparation of cis-2-(((2-(3-(m-tolyloxy)cyclohexyl)propyl)amino)methyl)aniline Using the same procedure described in Example 9, using 2-(aminomethyl)aniline in place of 4-(aminomethyl)pyridine, cis-N-(3-chlorobenzyl)-2-(3-(m-tolyloxy)cyclohexyl)propan-1-amine was prepared analogously (LC/MS=353.2 [M+H]$^+$).

Example 16—Preparation of cis-N-(pyridin-3-ylmethyl)-2-(3-(m-tolyloxy)cyclohexyl)propan-1-amine Using the same procedure described in Example 9, using pyridin-3-ylmethanamine in place of 4-(aminomethyl)pyridine, cis-N-(pyridin-3-ylmethyl)-2-(3-(m-tolyloxy)cyclohexyl)propan-1-amine was prepared analogously (LC/MS=339.2 [M+H]$^+$).

Example 17—Preparation of cis-N-(2-chlorobenzyl)-2-(3-(m-tolyloxy)cyclohexyl)propan-1-amine Using the same procedure described in Example 9, using (2-chlorophenyl) methanamine in place of 4-(aminomethyl)pyridine, cis-N-(2-chlorobenzyl)-2-(3-(m-tolyloxy)cyclohexyl)propan-1-amine was prepared analogously (LC/MS=372.2 [M+H]$^+$).

Example 18—Preparation of cis-3-(((2-(3-(m-tolyloxy)cyclohexyl)propyl)amino)methyl)aniline Using the same procedure described in Example 9, using 3-(aminomethyl)aniline in place of 4-(aminomethyl)pyridine, cis-3-(((2-(3-(m-tolyloxy)cyclohexyl)propyl)-amino)methyl)aniline was prepared analogously (LC/MS=353.2 [M+H]$^+$).

Example 19—Preparation of cis-N-(4-chlorobenzyl)-2-(3-(m-tolyloxy)cyclohexyl)propan-1-amine Using the same procedure described in Example 9, using (4-chlorophenyl) methanamine in place of 4-(aminomethyl)pyridine, cis-N-(4-chlorobenzyl)-2-(3-(m-tolyloxy)cyclohexyl)propan-1-amine was prepared analogously (LC/MS=371.2[M+H]$^+$).

Example 20—Preparation of cis-N-(4-chlorobenzyl)-N-methyl-2-(3-(m-tolyloxy)cyclohexyl)propan-1-amine Using the same procedure described in Example 9, using 1-(4-chlorophenyl)-N-methylmethanamine in place of 4-(aminomethyl)pyridine, cis-N-(4-chlorobenzyl)-N-methyl-2-(3-(m-tolyloxy)cyclohexyl)propan-1-amine was prepared analogously (LC/MS=386.2 [M+H]$^+$).

Example 21—Preparation of cis-2-(((2-(3-(m-tolyloxy)cyclohexyl)propyl)amino)methyl)phenol Using the same procedure described in Example 9, using 2-(aminomethyl)phenol in place of 4-(aminomethyl)pyridine, cis-2-(((2-(3-(m-tolyloxy)cyclohexyl)propyl)-amino)methyl)phenol was prepared analogously (LC/MS=354.2 [M+H]$^+$).

Example 22—Preparation of cis-4-(((2-(3-(m-tolyloxy)cyclohexyl)propyl)amino)methyl)aniline Using the same procedure described in Example 9, using 4-(aminomethyl)aniline in place of 4-(aminomethyl)pyridine, cis-4-(((2-(3-(m-tolyloxy)cyclohexyl)propyl)-amino)methyl)aniline was prepared analogously (LC/MS=353.2 [M+H]$^+$).

Example 23—Preparation of cis-3-(((2-(3-(m-tolyloxy)cyclohexyl)propyl)amino)methyl)phenol Using the same procedure described in Example 9, using 3-(aminomethyl)phenol in place of 4-(aminomethyl)pyridine, cis-3-(((2-(3-(m-tolyloxy)cyclohexyl)propyl)amino)methyl)phenol was prepared analogously (LC/MS=354.2 [M+H]$^+$).

Example 24—Preparation of cis-4-(((2-(3-(m-tolyloxy)cyclohexyl)propyl)amino)methyl)phenol Using the same procedure described in Example 9, using 4-(aminomethyl)phenol in place of 4-(aminomethyl)pyridine, cis-4-(((2-(3-(m-tolyloxy)cyclohexyl)propyl)amino)methyl)phenol was prepared analogously (LC/MS=354.2 [M+H]$^+$).

Example 25—Preparation of cis-N-(pyrimidin-4-ylmethyl)-2-(3-(m-tolyloxy)cyclohexyl)propan-1-amine Using the same procedure described in Example 9, using pyrimidin-4-ylmethanamine in place of 4-(aminomethyl) pyridine, cis-N-(pyrimidin-4-ylmethyl)-2-(3-(m-tolyloxy) cyclohexyl)propan-1-amine was prepared analogously (LC/MS=340.2 [M+H]$^+$).

Example 26—Preparation of cis-N-(pyridin-4-ylmethyl)-N-(2-(3-(m-tolyloxy)cyclohexyl)propyl)acetamide cis-(N-(pyridin-4-ylmethyl)-2-(3-(m-tolyloxy)cyclohexyl)propan-1-amine)(0.338 g, 1 mmol), prepared as in Example 9, was dissolved in dichloromethane (5 mL) and treated with acetyl chloride (0.117 g, 1.5 mmol) and triethylamine (0.152 g, 1.5 mmol), and stirred at 0° C. to room temperature for 3 h. The mixture was partitioned between ethyl acetate and sodium bicarbonate solution, and the organic layer was separated, dried and evaporated to dryness to afford the crude product. Purification by preparative HPLC afforded the pure cis-N-(pyridin-4-ylmethyl)-N-(2-(3-(m-tolyloxy)cyclohexyl)propyl)acetamide (LC/MS=381.2 [M+H]$^+$).

Example 27—Preparation of cis-2-(3-(m-tolyloxy)cyclohexyl)propan-1-amine

Using the same procedure described in Example 9, using 7N NH$_4$OH in methanol in place of 4-(aminomethyl)pyridine, cis-2-(3-(m-tolyloxy)cyclohexyl)propan-1-amine was prepared analogously (LC/MS=248.2 [M+H]$^+$).

Example 28—Preparation of cis-N-(2-(3-(m-tolyloxy)cyclohexyl)propyl)isonicotinamide 2-(3-(m-tolyloxy)cyclohexyl)propan-1-amine (prepared in Example 27) was coupled with iso-nicotinic acid using a standard coupling procedure (HATU/diisopropylethylamine/DMF) to afford cis-N-(2-(3-(m-tolyloxy)cyclohexyl) propyl) isonicotinamide after purification by preparative HPLC (LC/MS=353.2 [M+H]$^+$).

Example 29—Preparation of cis-N-((1H-benzo[d] imidazol-5-yl)methyl)-2-(3-(m-tolyloxy)cyclohexyl) propan-1-amine Using the procedure described in Example 9a, cis-2-(3-(m-tolyloxy)cyclohexyl)propan-1-amine, prepared in Example 27, was reacted with 1H-benzo[d]imidazole-5-carbaldehyde and purified by preparative HPLC to afford cis-N-((1H-benzo[d]imidazol-5-yl)methyl)-2-(3-(m-tolyloxy)cyclohexyl)-propan-1-amine (LC/MS=378.2 [M+H]$^+$).

Example 30—Preparation of cis-N-benzyl-2-(3-(3-methoxyphenoxy)cyclohexyl)propan-1-amine Using the procedure described in Example 9, substituting cis-2-(3-(3-(methoxy)phenoxy)cyclohexyl)propanal for cis-2-(-3-(m-tolyloxy)cyclohexyl)propanal, reaction with benzylamine afforded cis-2-(3-(3-methoxyphenoxy)cyclohexyl)-N-(pyridin-3-ylmethyl)propan-1-amine (LC/MS=354.2 [M+H]$^+$).

Example 31—Preparation of cis-2-(3-(3-methoxyphenoxy)cyclohexyl)-N-(pyridin-3-ylmethyl)propan-1-amine Using the procedure described in Example 16, substituting cis-2-(3-(3-(methoxy)phenoxy)cyclohexyl)propanal for cis-2-(-3-(m-tolyloxy)cyclohexyl)propanal, reaction with 3-(aminomethyl)pyridine afforded cis-2-(3-(3-methoxyphenoxy)cyclohexyl)-N-(pyridin-3-ylmethyl)propan-1-amine (LC/MS=355.2 [M+H]+).

Example 32—Preparation of cis-2-(3-(3-methoxyphenoxy)cyclohexyl)-N-(pyridin-4-ylmethyl)propan-1-amine Using the procedure described in Example 9, substituting cis-2-(3-(3-(methoxy)phenoxy)cyclohexyl)propanal for cis-2-(-3-(m-tolyloxy)cyclohexyl)propanal, reaction with 4-(aminomethyl)pyridine afforded cis-2-(3-(3-methoxyphenoxy)cyclohexyl)-N-(pyridin-4-ylmethyl)propan-1-amine (LC/MS=355.2 [M+H]+).

Example 33—Preparation of cis-N-benzyl-2-(3-(3-(trifluoromethyl)phenoxy)cyclohexyl)propan-1-amine Using the procedure described in Example 9, substituting cis-2-(3-(3-(trifluoromethyl)phenoxy)cyclohexyl)propanal for cis-2-(-3-(m-tolyloxy)cyclohexyl) propanal, reaction with benzylamine afforded cis-N-benzyl-2-(3-(3-(trifluoromethyl) phenoxy)cyclohexyl)propan-1-amine (LC/MS=392.2 [M+H]+).

Example 34—Preparation of cis-N-(pyridin-3-ylmethyl)-2-(3-(3-(trifluoromethyl)phenoxy)cyclohexyl)propan-1-amine Using the procedure described in Example 16, substituting cis-2-(3-(3-(trifluoromethyl)phenoxy)cyclohexyl)propanal for cis-2-(-3-(m-tolyloxy)cyclohexyl)propanal, reaction with 3-(aminomethyl)pyridine afforded cis-N-(pyridin-3-ylmethyl)-2-(3-(3-(trifluoromethyl)phenoxy)cyclohexyl)propan-1-amine (LC/MS=393.2[M+H]+).

Example 35—Preparation of cis-N-(pyridin-4-ylmethyl)-2-(3-(3-(trifluoromethyl)phenoxy)cyclohexyl)propan-1-amine Using the procedure described in Example 9, substituting cis-2-(3-(3-(trifluoromethyl)phenoxy)cyclohexyl)propanal for cis-2-(-3-(m-tolyloxy)cyclohexyl) propanal, reaction with 4-(aminomethyl)pyridine afforded cis-N-(pyridin-4-ylmethyl)-2-(3-(3-(trifluoromethyl)phenoxy)cyclohexyl)propan-1-amine (LC/MS=393.2 [M+H]+).

Example 36—Screening of C458 Analogs Against Aβ Toxicity in MC65 Cells

Figure 11A:
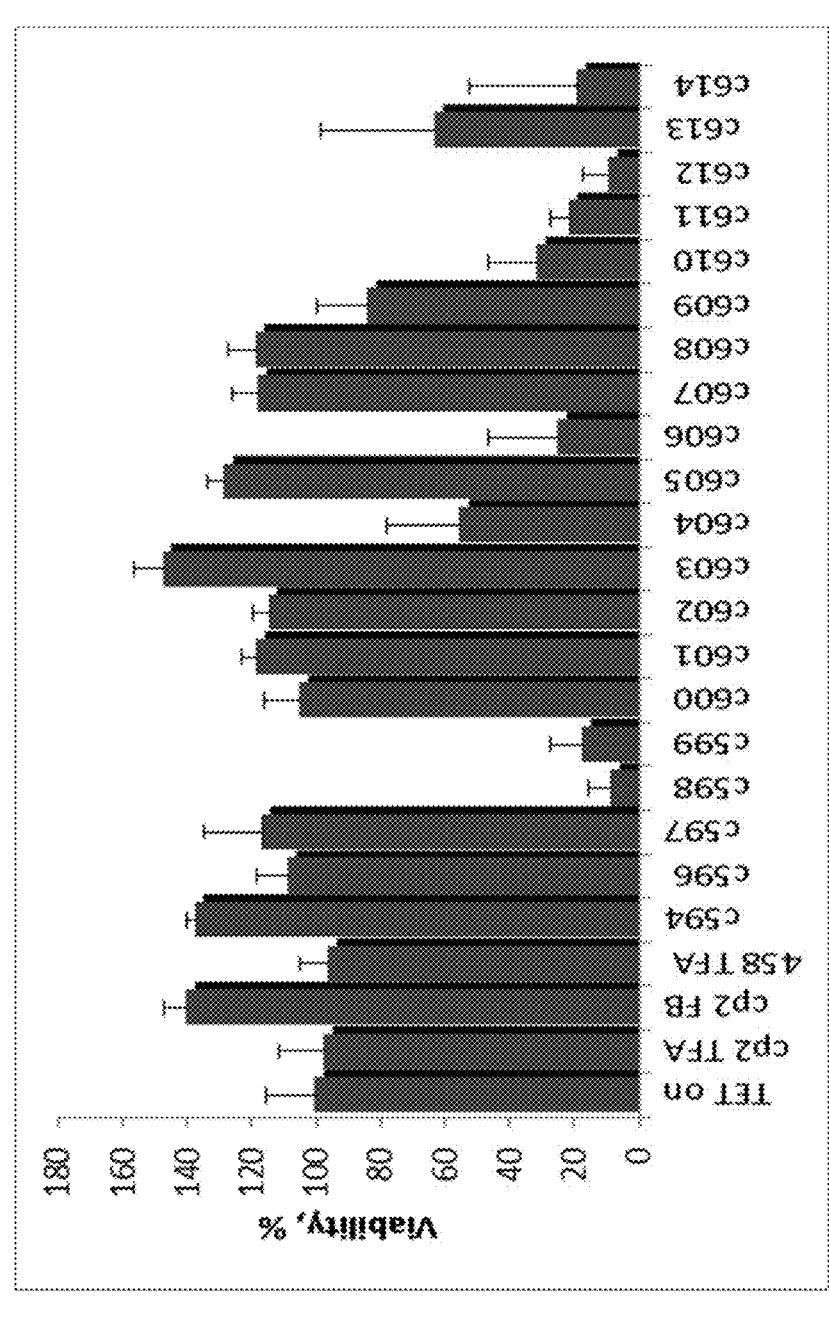
Figure 11B:
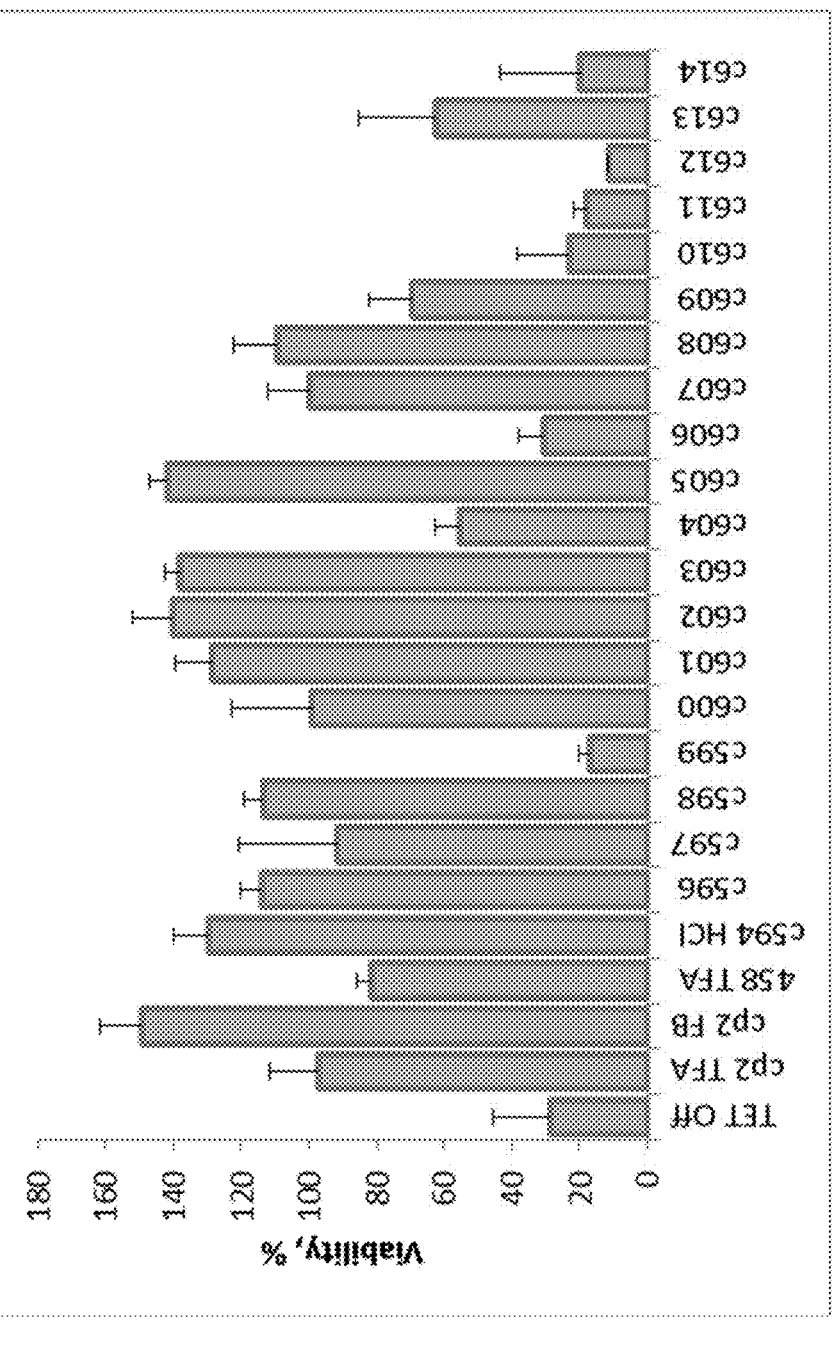

The C458-like compounds (TABLE 3) were evaluated using Aβ-producing MC65 cells. Several C458 analogs (C594, C596, C600-C603, C607, and C608) demonstrated efficacy against Aβ toxicity comparable to that of CP2 and C458 (FIGS. 11A and 11B).

Example 37—Molecular Mechanism of Action

Using in vitro and in vivo assays, as well as computational chemistry, the molecular mechanism for the action of CP2, C458, and C458 analogs was tested. These studies showed that the first enzymatic complex of the mitochondrial oxidative phosphorylation (OXPHOS) machinery that produces cellular energy in the form of ATP (Complex I) is a target for new CP2 and C458 analogs.

Figure 13:
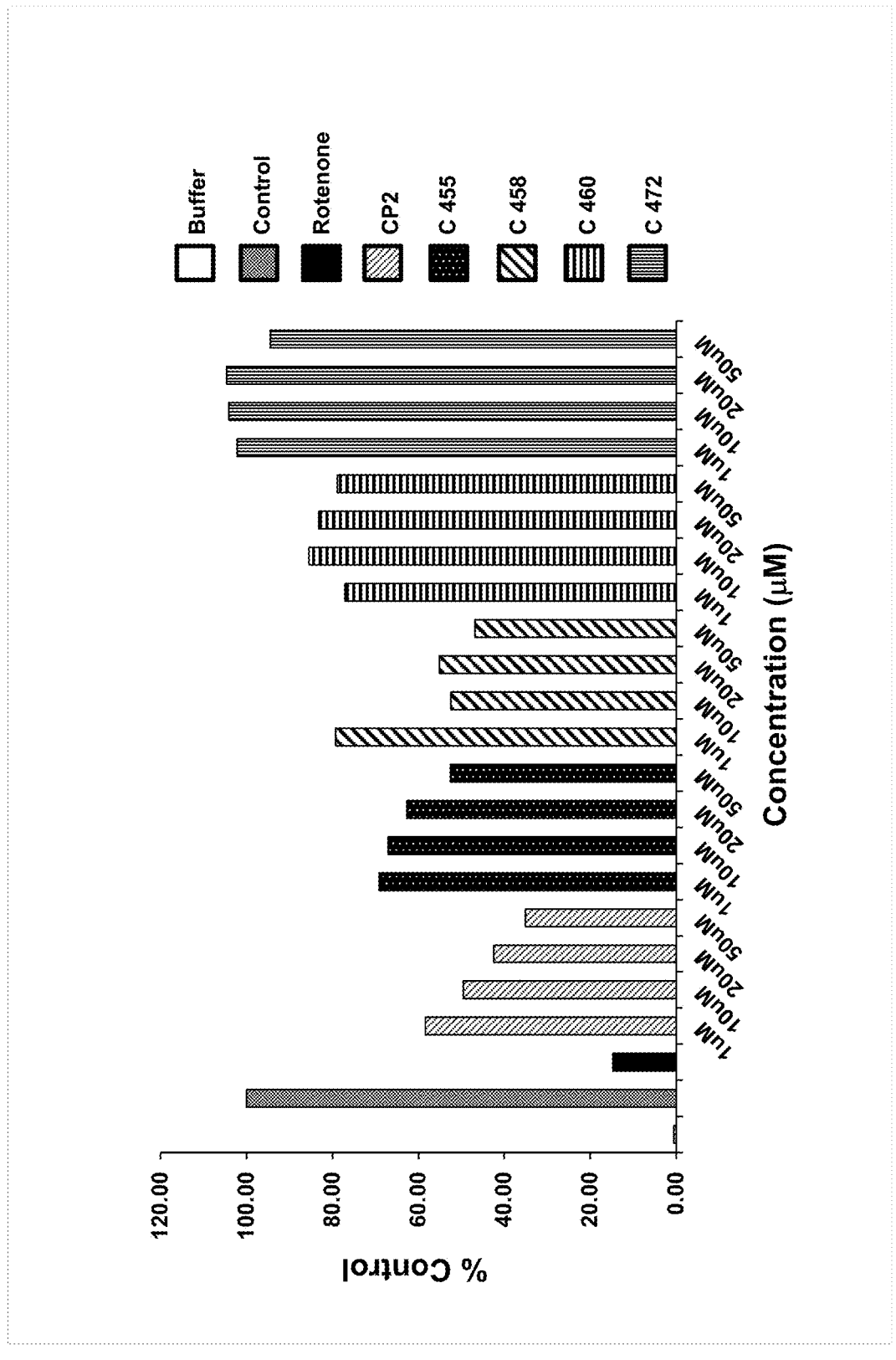
FIG. 13 is a graph plotting Complex I activity measured in isolated mitochondria from mouse brain after treatment with the indicated concentrations of the indicated compounds or controls. Mouse brain homogenates were prepared as described elsewhere (*Nature Protocols* 7(6), 2012; doi:10.1038/nprot.2012.058). Isolated mitochondria (40 μg) were treated with vehicle control (control), rotenone (Complex I inhibitor, negative control) or the indicated compound. Complex I activity was measured as the decrease in absorbance at 340 nm for 5 minutes, starting the reactions by adding ubiquinone (10 mM) to isolated mitochondria in the reaction mixture. All experiments were performed in duplicate.

Since CP2 targets Complex I, experiments were conducted to determine whether the CP2 and C458 analogs also can target Complex I and affect mitochondrial functions such as ATP production, Complex I activity, and NAD+/NADH ratios. ATP production was measured in primary cortical neurons treated with CP2 and four novel CP2 analogs (FIGS. 12A and 12B). Compounds C455, C458 and CP2 modestly reduced ATP production over a concentration range from 10 nM to 5 while C460 and C472 had little or no effect on ATP production. In good agreement, compounds C455, C458, and CP2 also resulted in 20 to 30 percent inhibition of Complex I activity (FIG. 13).

Figure 14A:
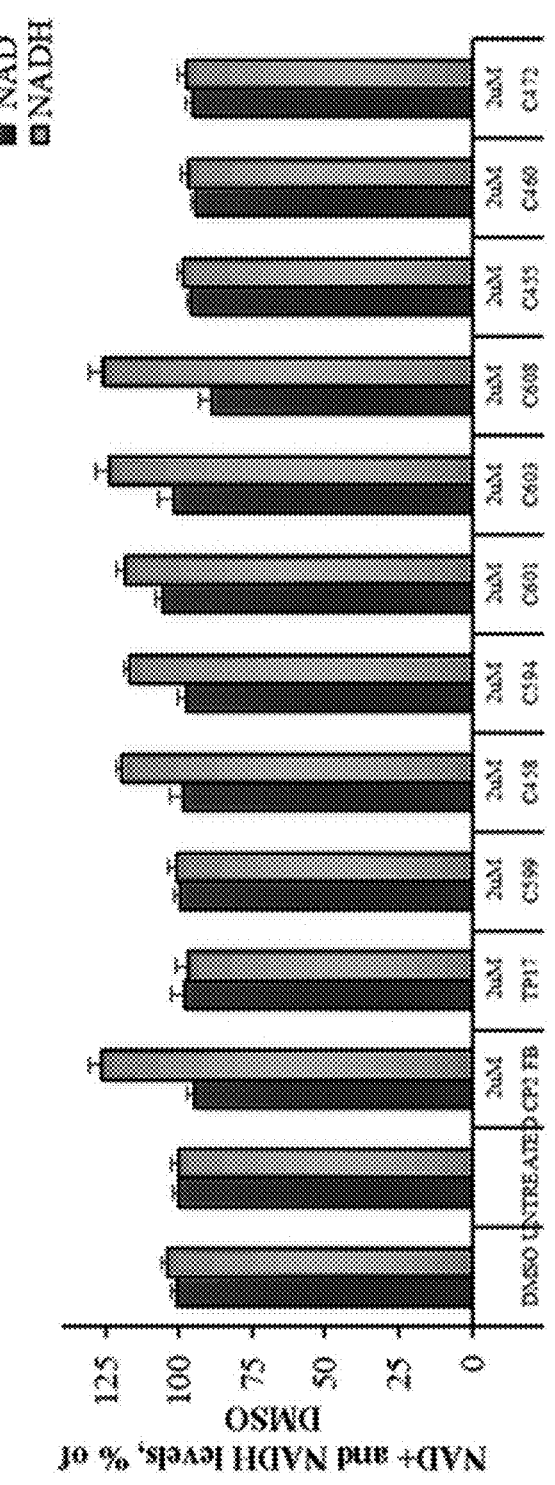
FIGS. 14A and 14B are graphs plotting $NAD^+$ and NADH levels (FIG. 14A) or the $NAD^+$/NADH ratio (FIG. 14B) in primary embryonic cortical neurons after treatment with the indicated compounds. Neurons were seeded on 96-well plates at 30,000 cells per well. Seven days later, cells were treated with each compound at 2 μM. $NAD^+$ and NADH levels were measured 24 hours later using the bioluminescent $NAD^+$/NADH-GLO assay (Promega; Madison, Wis.). $NAD^+$ and NADH levels are expressed as a percent of vehicle treated (control) cells (FIG. 14A). All experiments were performed in 6 replicates.
Figure 14B:
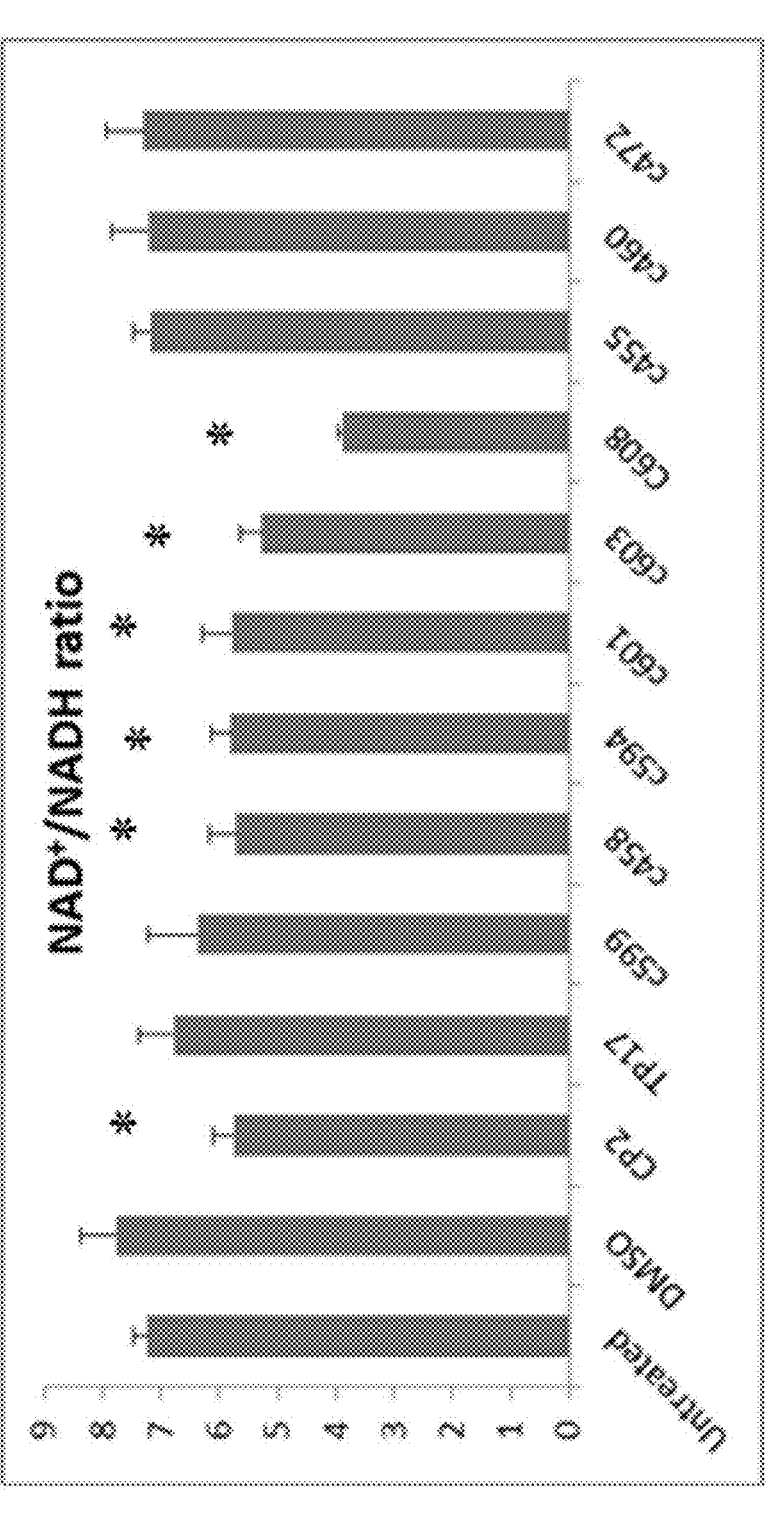

Further, CP2 and C458 analogs, but not an inactive CP2 analog (TP17) or an inactive C458 analog (C599), increased levels of NADH and decreased the NAD+/NADH ratio in primary neurons (Zhang et al., *eBioMedicine*, 2015). These studies indicated that active compounds targets Complex I activity (FIGS. 14A and 14B), resulting in mild modulation of its activity.

Figure 15A:
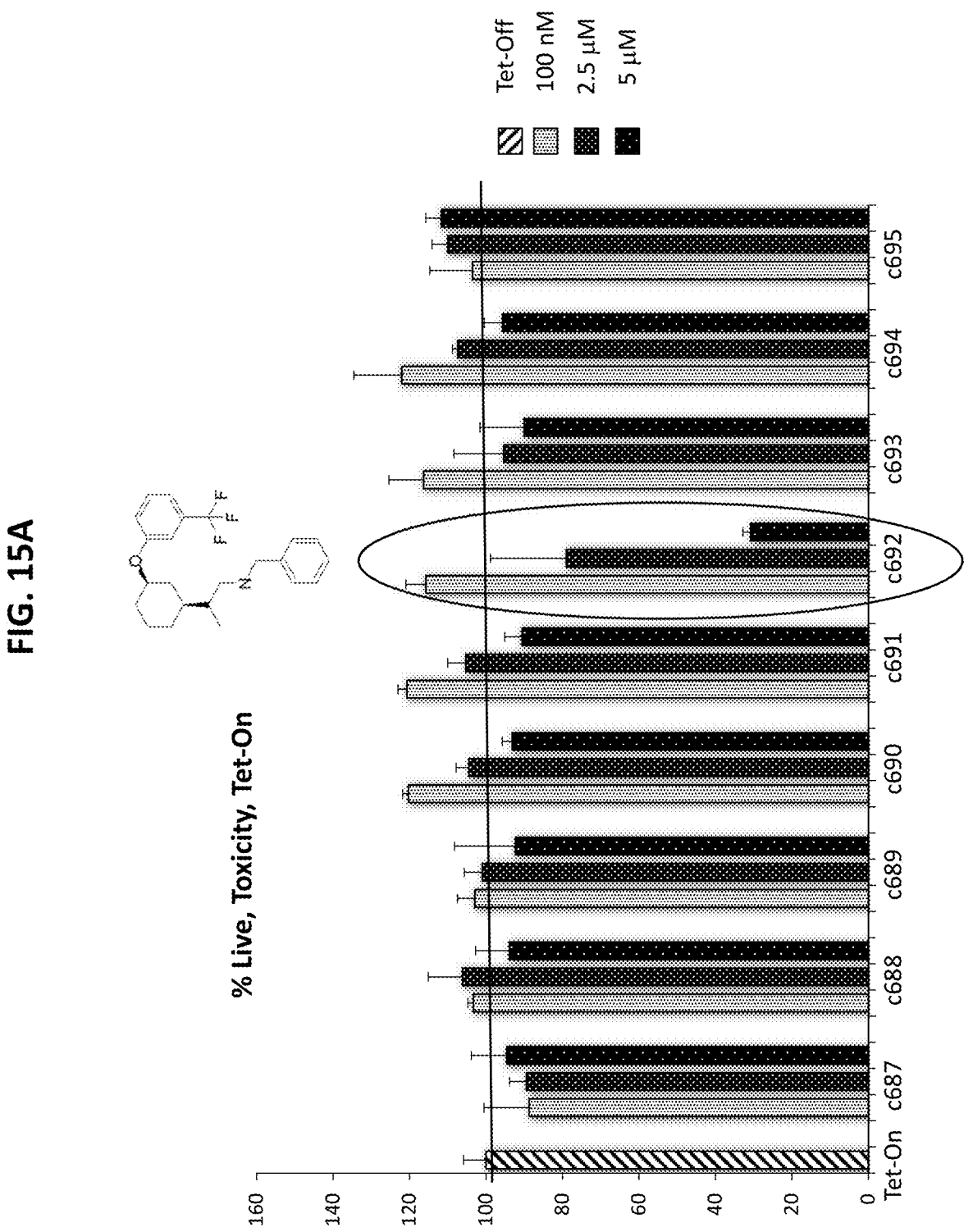
FIGS. 15A and 15B are graphs plotting percent survival of MC65 cells cultured in the presence of tetracycline (Tet-On) (FIG. 15A) or without tetracycline (Tet-off) (FIG. 15B) in OPTI-MEM media without serum. Cells at the time of plating were treated with either vehicle (0.05% final DMSO) or CP2, C458, C764 at 100 nM, 2.5 μM, and 5 μM concentrations. Cell viability was measured with an MTT assay 72 hours after plating. Experiments were performed in triplicate, and were repeated independently twice.
Figure 15B:
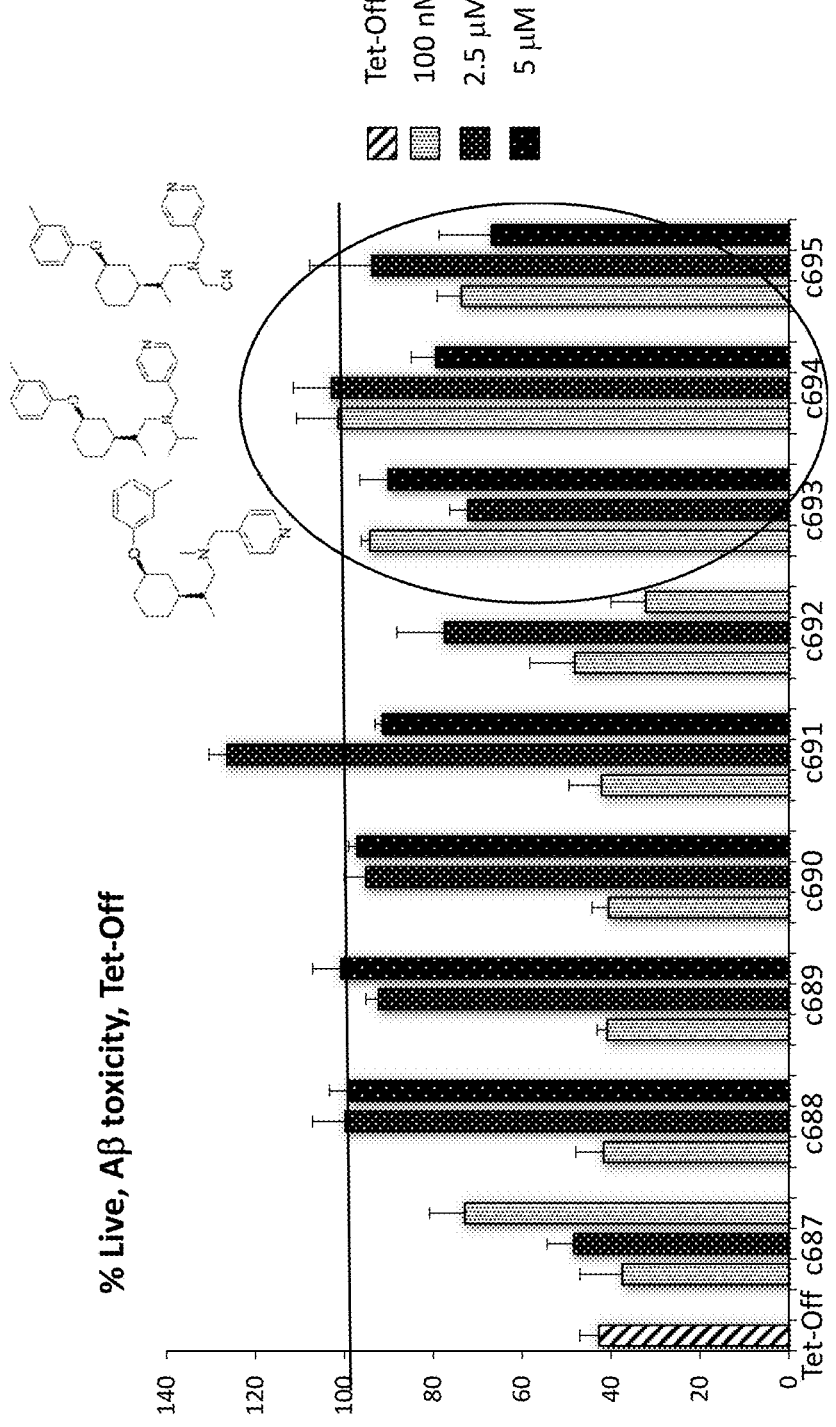

Example 38—Screening of Additional C458 Analogs Against Aβ Toxicity in MC65 Cells The activity of nine (9) new compounds (C687-C695) was tested in an Aβ toxicity assay in MC65 cells (FIGS. 15A and 15B). The structures of several of these compounds were as follows:

C692

C693

C694

C695

All of the new compounds, excluding compound C692, demonstrated a lack of toxicity and high efficacy against Aβ toxicity in these cells. Compounds C693-C695 demonstrated much higher efficacy against Aβ toxicity compared to the rest of the compounds (circled in FIG. 15B).

Figure 16:
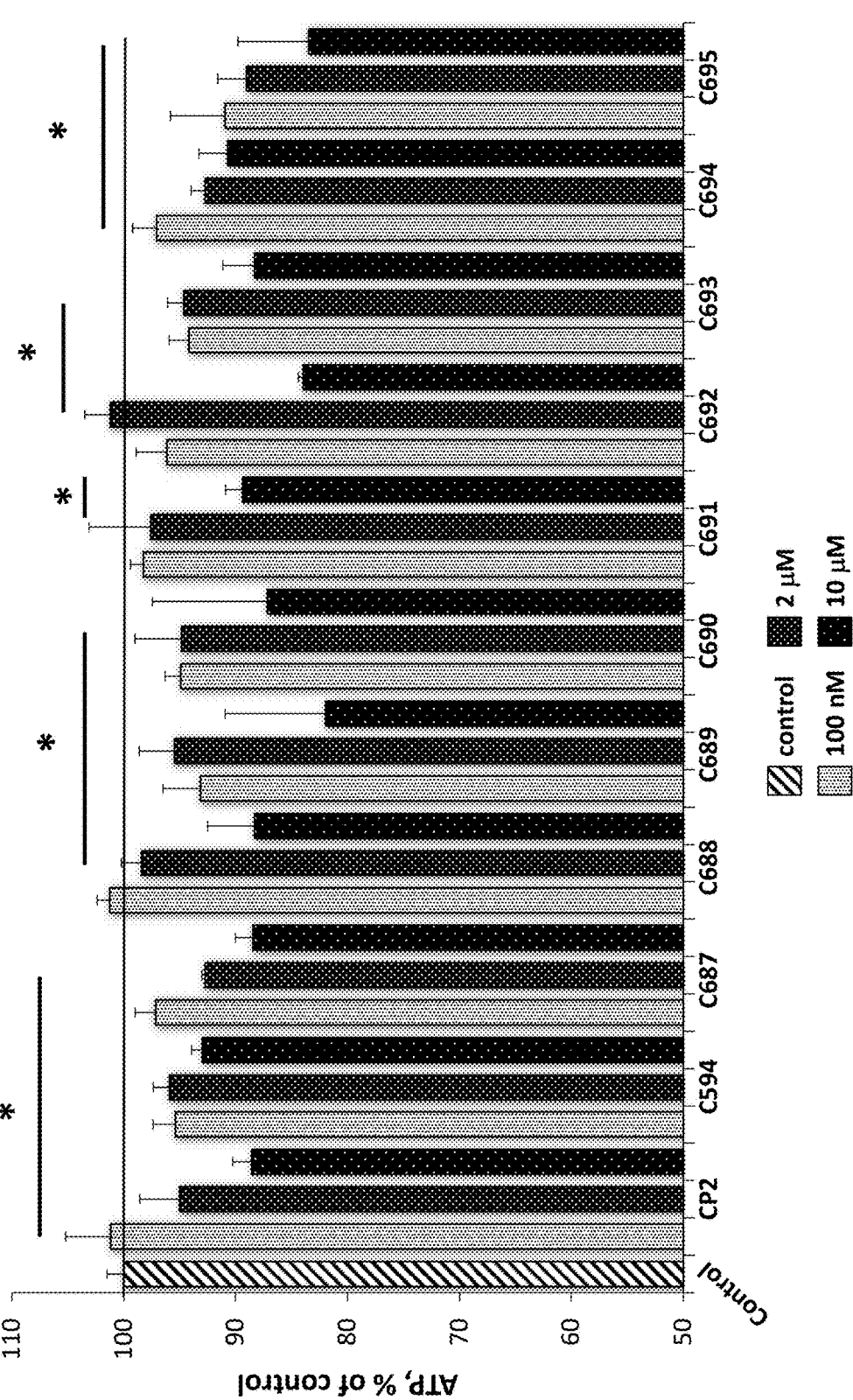
FIG. 16 is a graph plotting Complex I activity measured in isolated mitochondria from mouse brain homogenates. Isolated mitochondria (40 μg) were treated with vehicle (control), rotenone (Complex I inhibitor, negative control), and each of the indicated compounds at 100 nM and 5 μM concentrations. Complex I activity was measured for 5 minutes as the decrease in absorbance at 340 nm after the reaction was initiated by adding ubiquinone (10 mM) to isolated mitochondria in the reaction mixture. All experiments were performed in duplicate.
Figure 17:
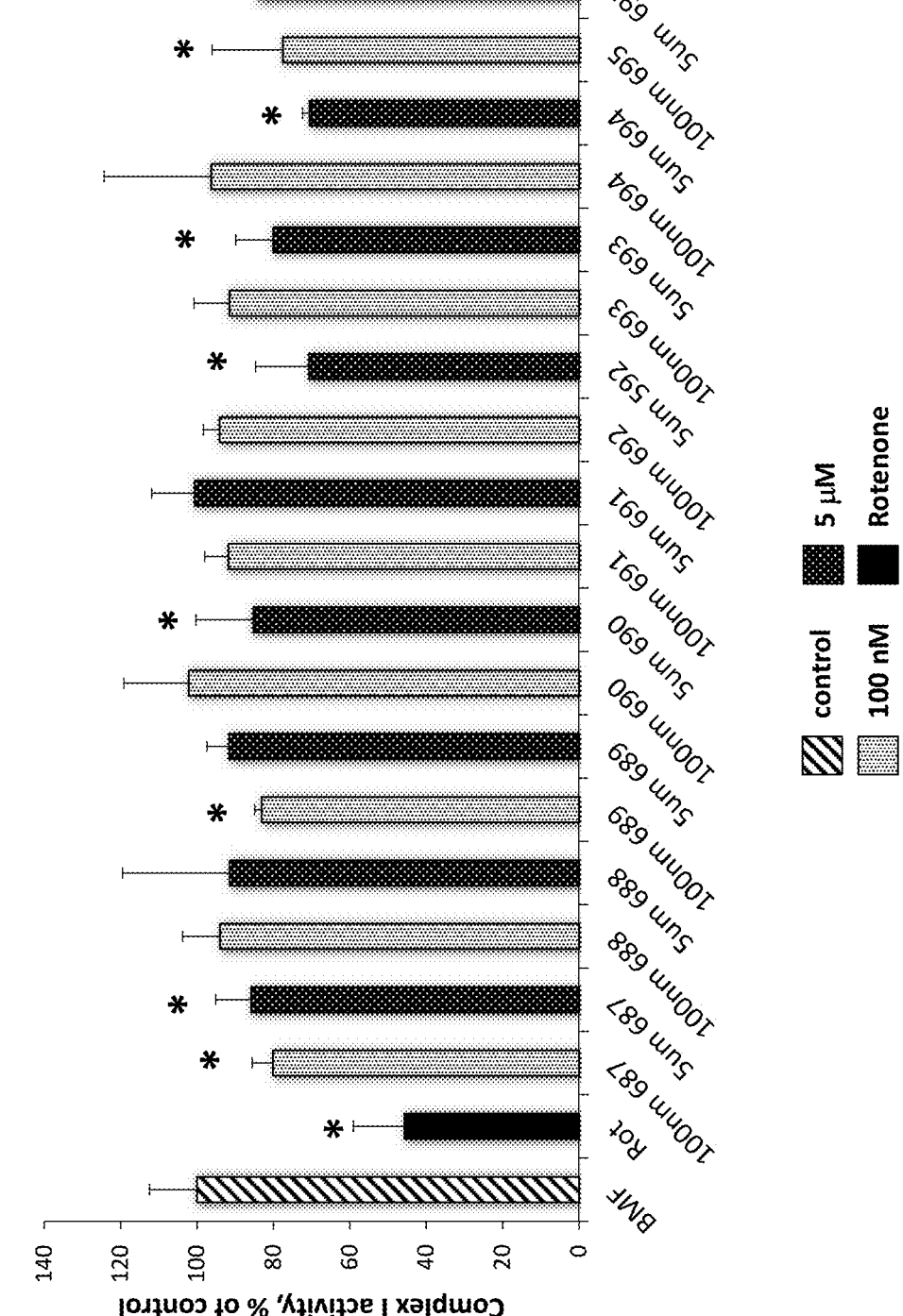
FIG. 17 is a graph plotting ATP levels in primary embryonic cortical neurons after seeding on a 96-well plate at 30,000 cells per well and being treated seven days later with the indicated compounds at concentrations of 100 nM, 2 and 5 μM. ATP levels were measured 24 hours after treatment using the bioluminescent CellTiter-GLO 2 assay (Promega, Madison, Wis.). All experiments were performed in 6 replicates.
Figure 18A:
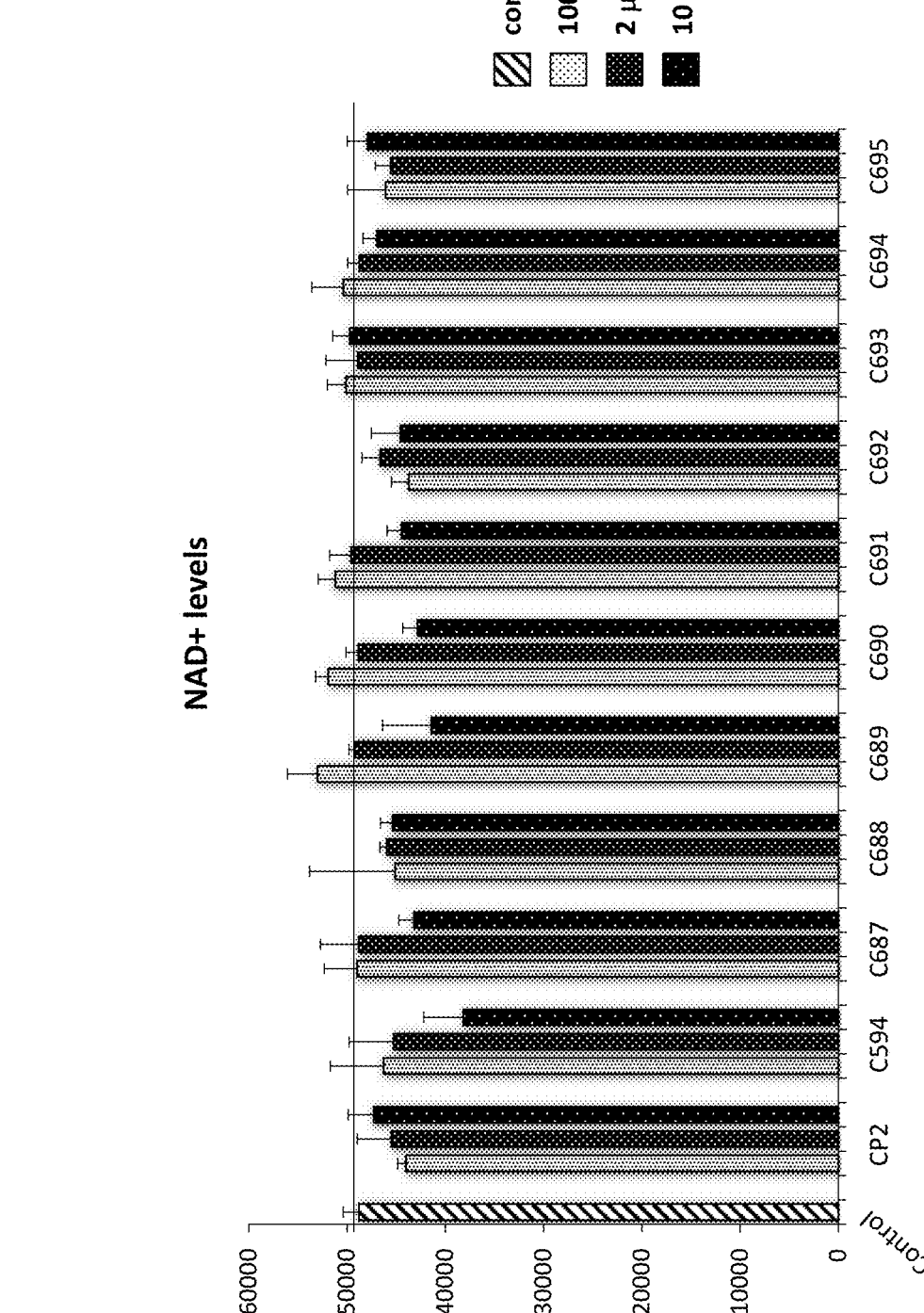
FIGS. 18A-18C are graphs plotting the level of NAD+ (FIG. 18A), the level of NADH (FIG. 18B), and the ratio of NAD+/NADH (FIG. 18C) in primary embryonic cortical neurons that were seeded on a 96-well plate at 30,000 cells per well and treated seven days later with the indicated compounds at concentrations 100 nM, 2 μM and 5 μM. NAD+, NADH, and NAD+/NADH ratio were measured using a bioluminescent NAD+/NADH-GLO assay (Promega). All experiments were performed in 6 replicates.
Figure 18B:
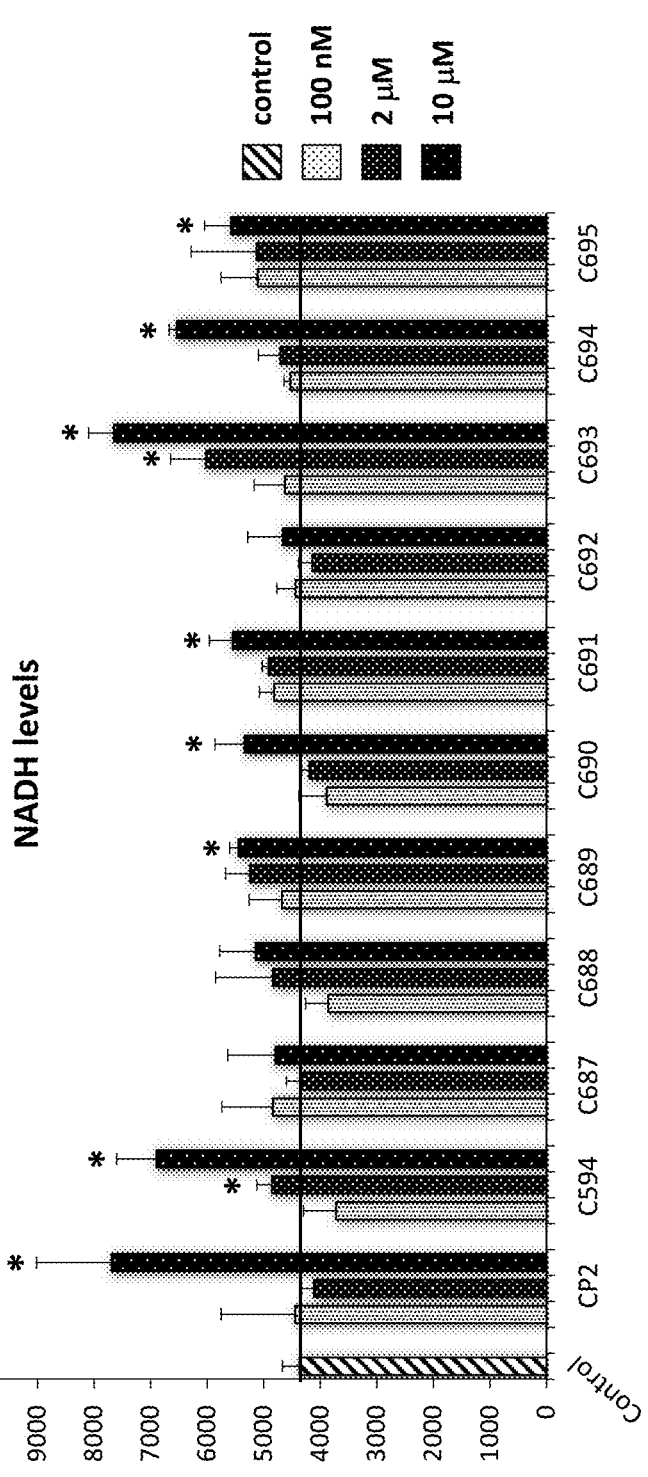
Figure 18C:
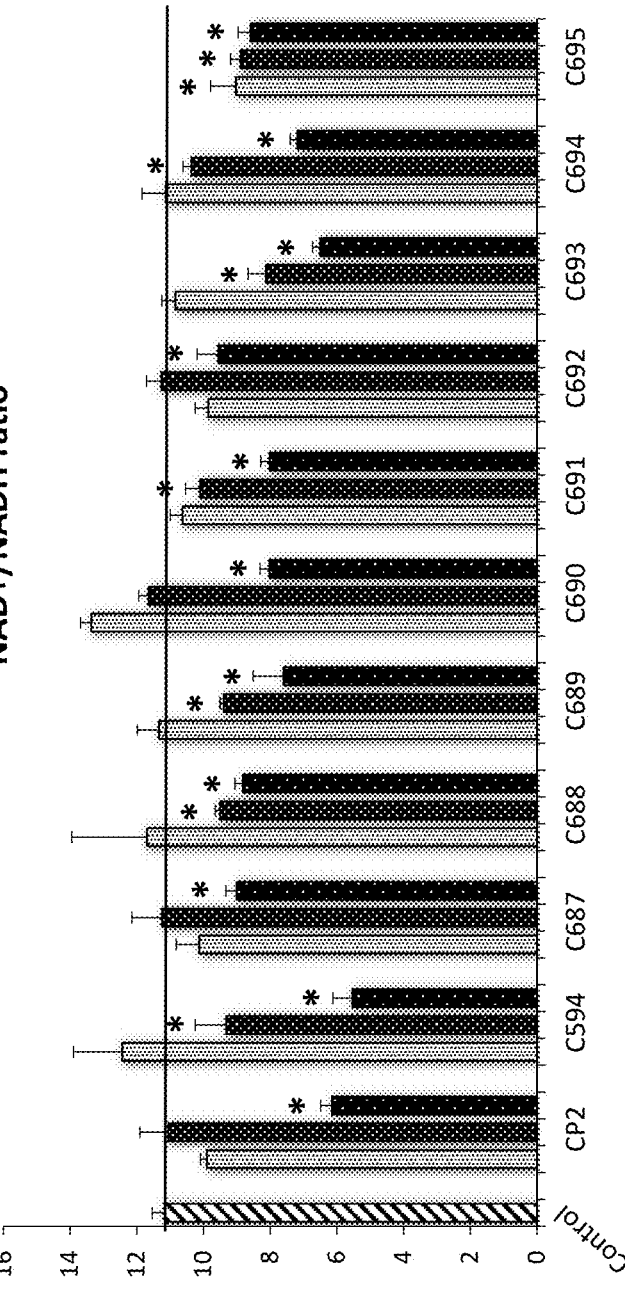

Example 39—Screening of Additional C458 Analogs for Complex I Inhibition and Production of ATP, NAD+, and NADH To further characterize these nine new compounds, Complex I activity was measured in isolated mitochondria, and levels of ATP, NAD+, and NADH were measured in primary mouse embryonic cortical neurons (FIGS. 16-18). All compounds decreased Complex I activity by 10-25% at 5 μM (FIG. 16). In agreement with the proposed molecular target and the mechanism, all compounds also mildly inhibited ATP production by 15-25% (FIG. 17). Finally, while all of the new compounds increased levels of NADH and decreased the NAD+/NADH ratio (FIGS. 18A-18C), C693 and C694 demonstrated the highest efficacy.

Figure 19:
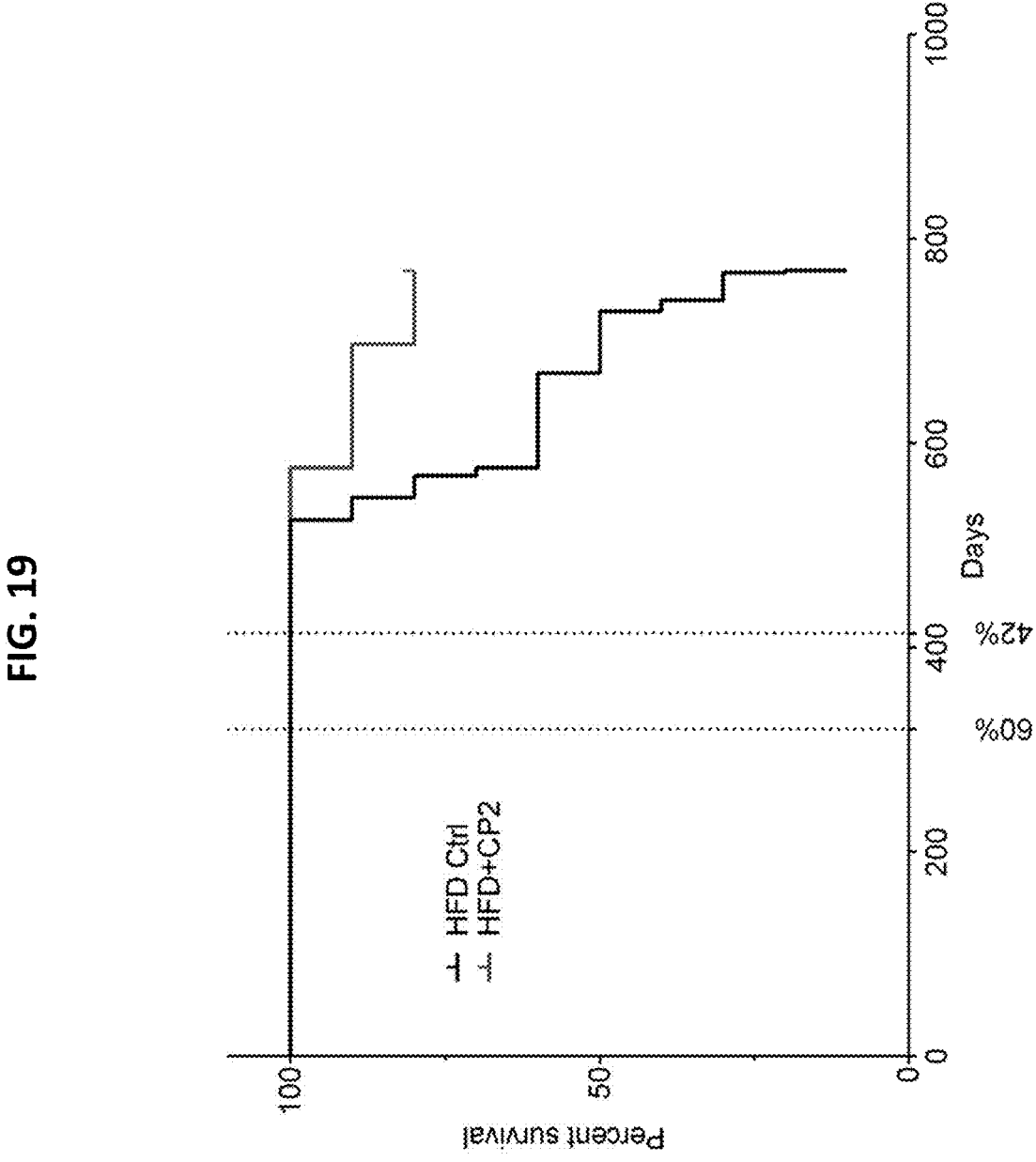
FIG. 19 is a graph plotting survival of mice that were fed a high fat diet (HFD) and untreated or treated with CP2, as indicated.

Example 40—Anti-Cancer Activity of Compounds that Modulate Mitochondrial Function The effect of CP2 and related compounds on cancer was tested in vitro and in vivo. First, CP2 and C458 were tested in WT mice fed a high fat diet (HFD). Two groups of female mice 288 days old (n=10 mice per group) were used; one group was given CP2 (25 mg/kg via drinking water) starting at 288 days of age (FIG. 19). At 320 days of age, CP2-treated and untreated mice were put on HFD (60%) for 94 days. After that, both groups were on 42% HFD for 272 days (until the age of 686 days). Within this period of time, most of the untreated WT mice developed different types of tumors (breast, liver, and abdominal tumors), and 90% of the untreated WT mice died. In contrast, the CP2-treated mice did not develop tumors, and demonstrated increased rates of survival (FIG. 19). Thus, these experiments suggested that CP2 may prevent the development of cancer.

Figure 20A:
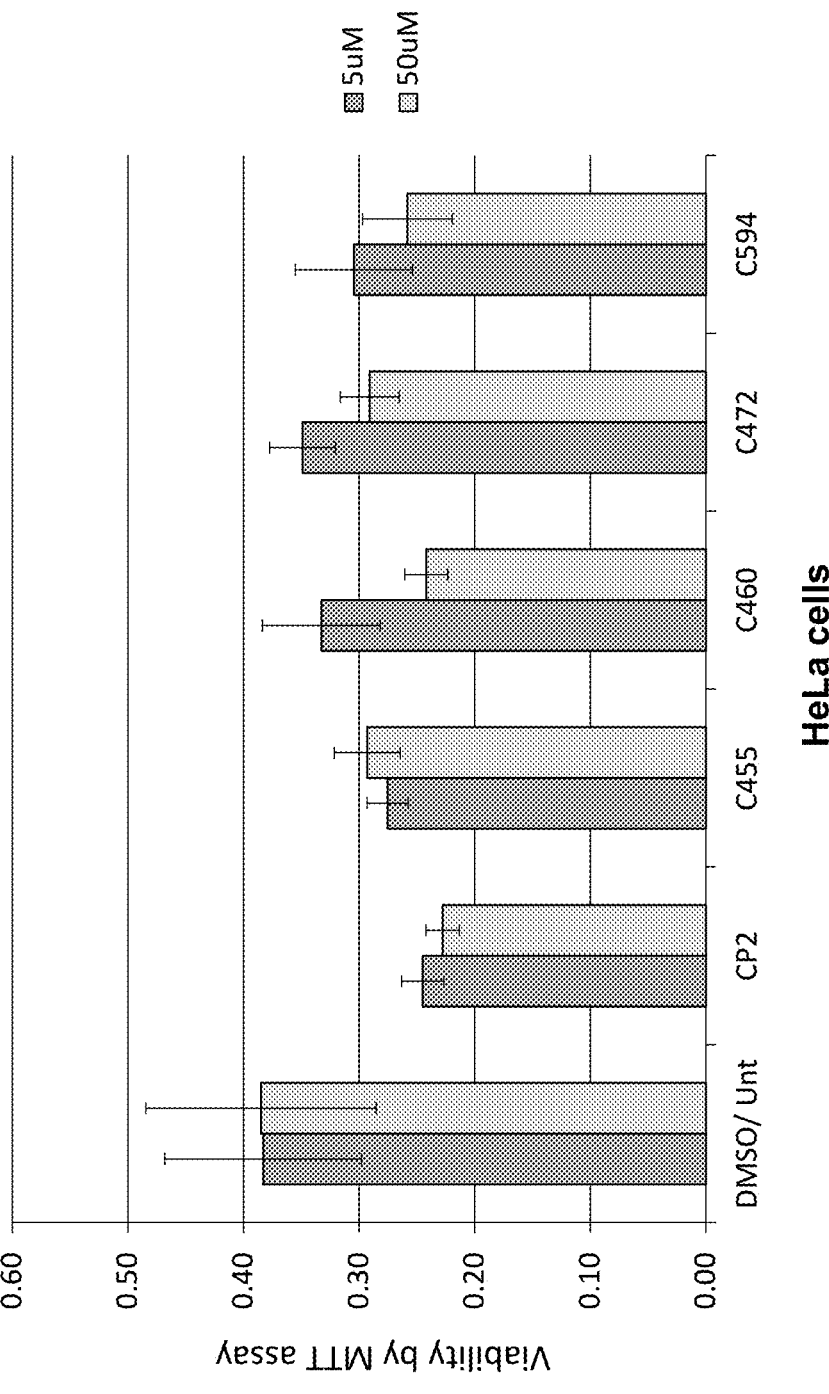
FIGS. 20A-20G are a series of graphs plotting the effect of the indicated compounds on survival of various cancer cells vs. control.
Figure 20B:
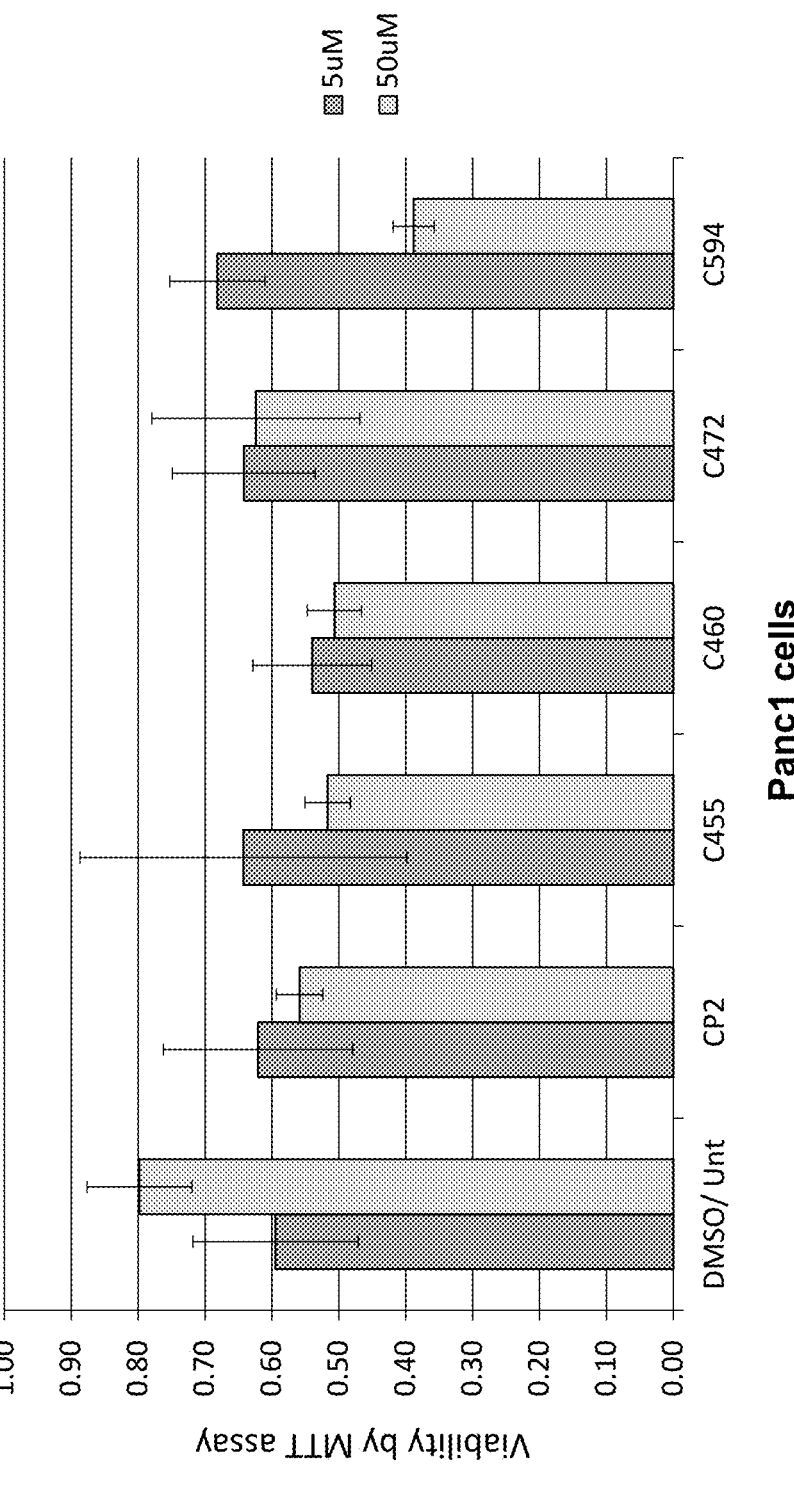
Figure 20C:
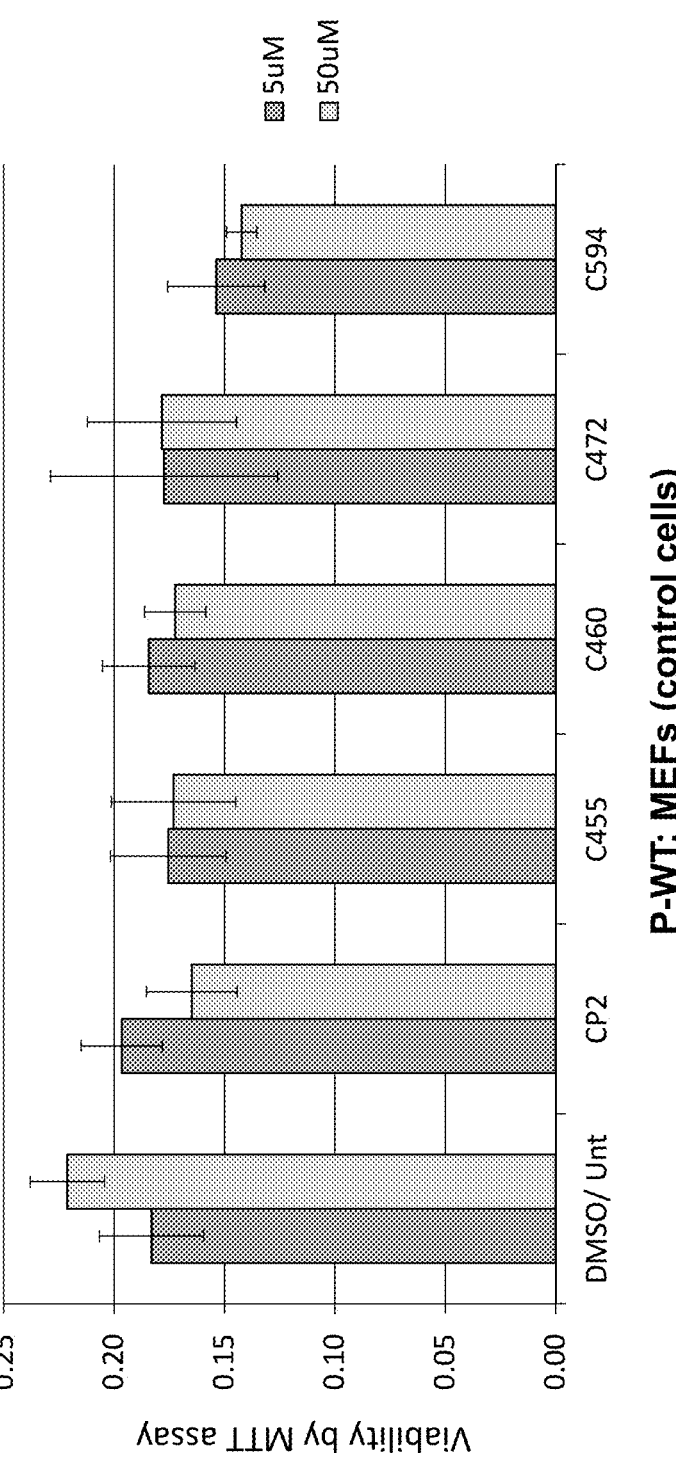
Figure 20D:
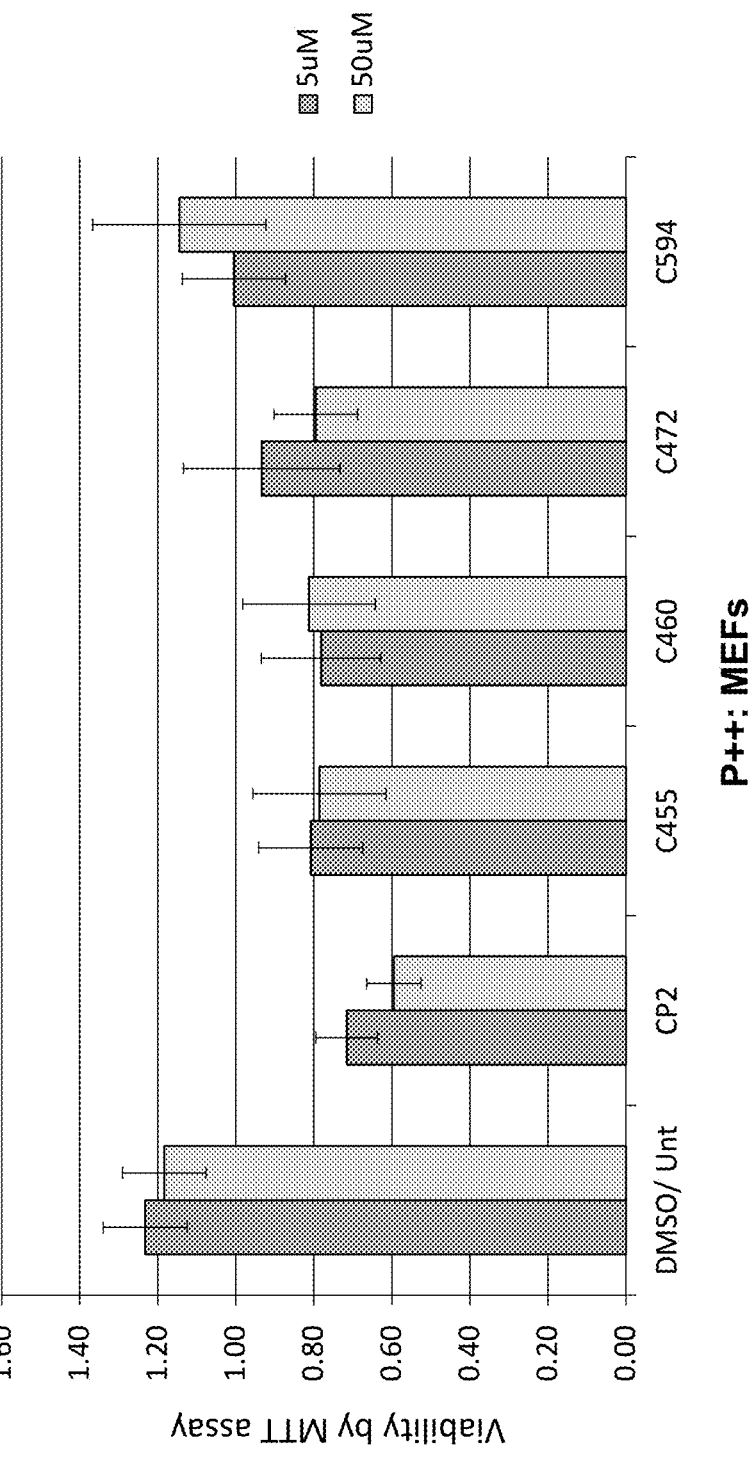
Figure 20E:
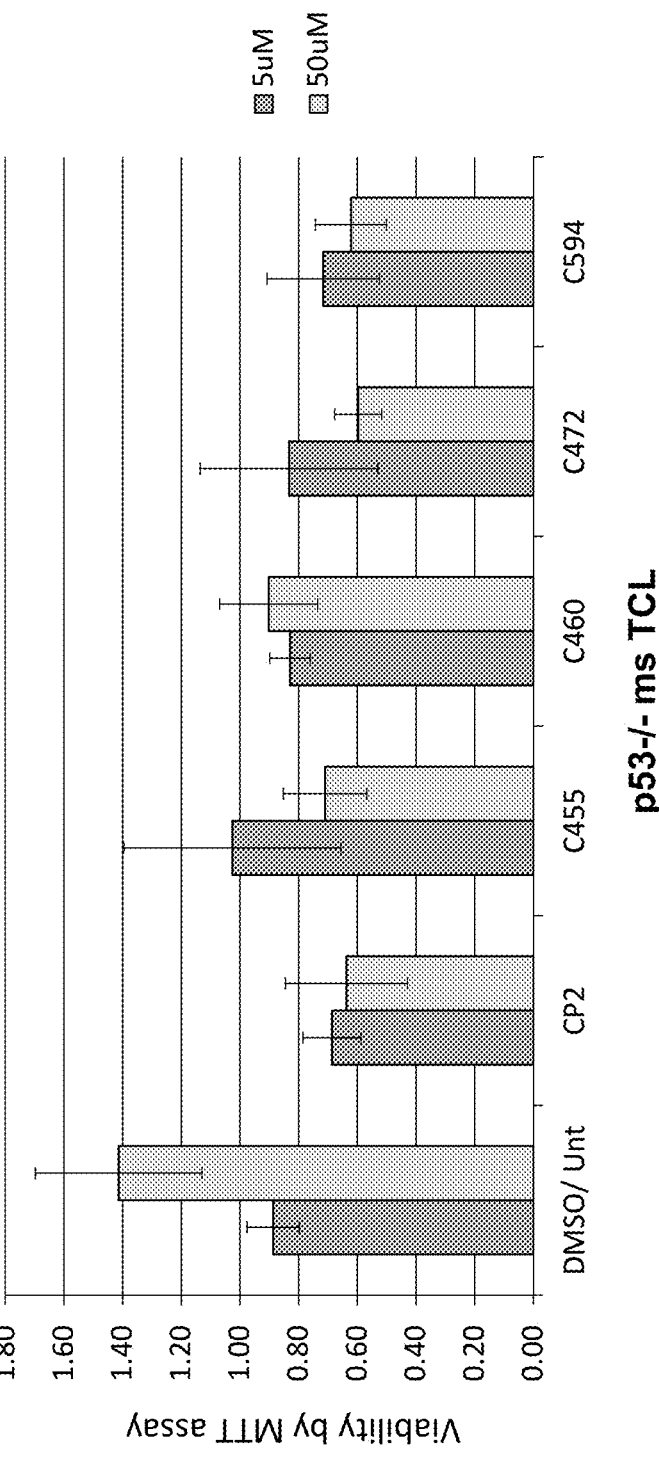
Figure 20F:
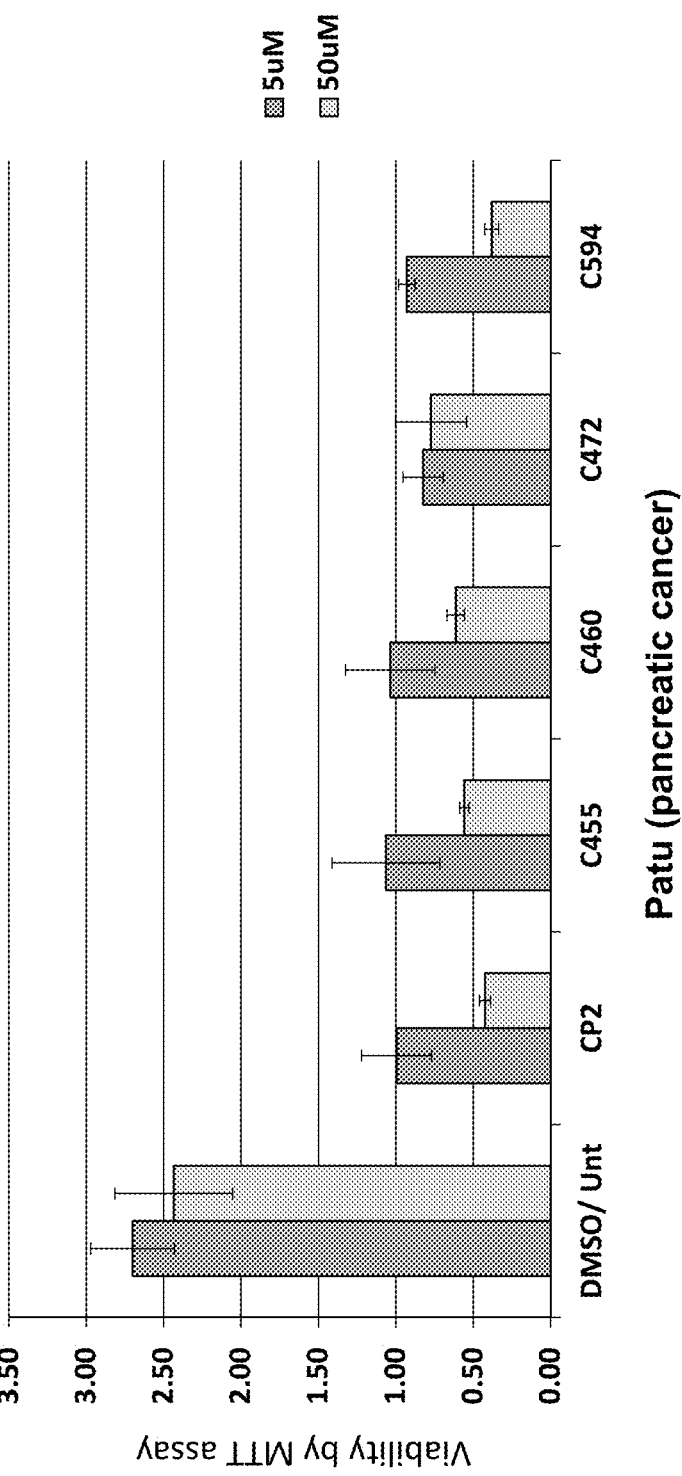
Figure 20G:
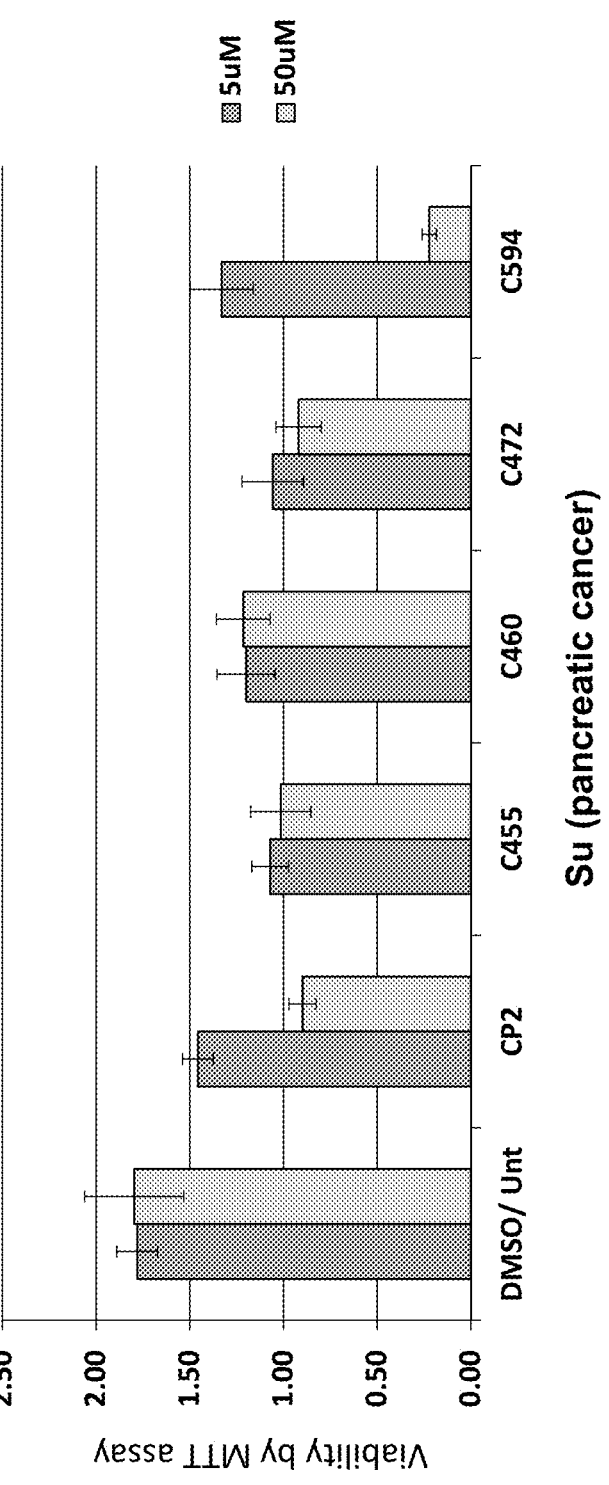

To further test this hypothesis, various cancer cell lines were treated with different doses (5 μM or 50 μM) of CP2 or compounds C455, C460, C472, or C594, and cell death was evaluated using an MTT assay. The following human cell lines were used: HeLa (cervical cancer, FIG. 20A); Panc1 (pancreatic cancer, FIG. 20B); P-WT MEFs (control, FIG. 20C), P++ MEFs (accelerated aging phenotype, FIG. 20D) p53–/– ms TCL (FIG. 20E); Patu (pancreatic cancer, FIG. 20F), and Su (pancreatic cancer, FIG. 20G). The compounds had varying effects on the different cell lines, but in general they suppressed growth of the cancer cell lines tested—particularly at the higher dose. The compounds did not affect the survival of WT mouse embryonic fibroblasts (FIG. 20C), but they did suppress the growth of MEFs that were P++(FIG. 20D).

Figure 21A:
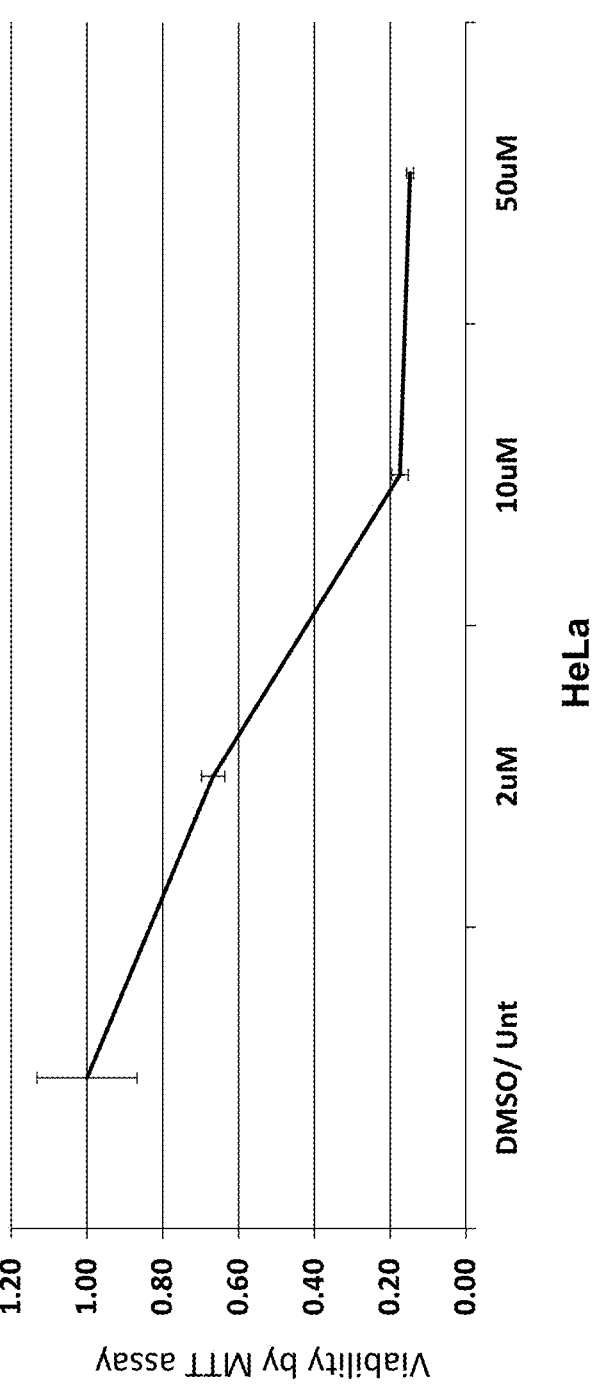
FIGS. 21A-21H are a series of graphs plotting the results of dose response studies for CP2 in the cells used in FIGS. 20A-20G, with an additional control.
Figure 21B:
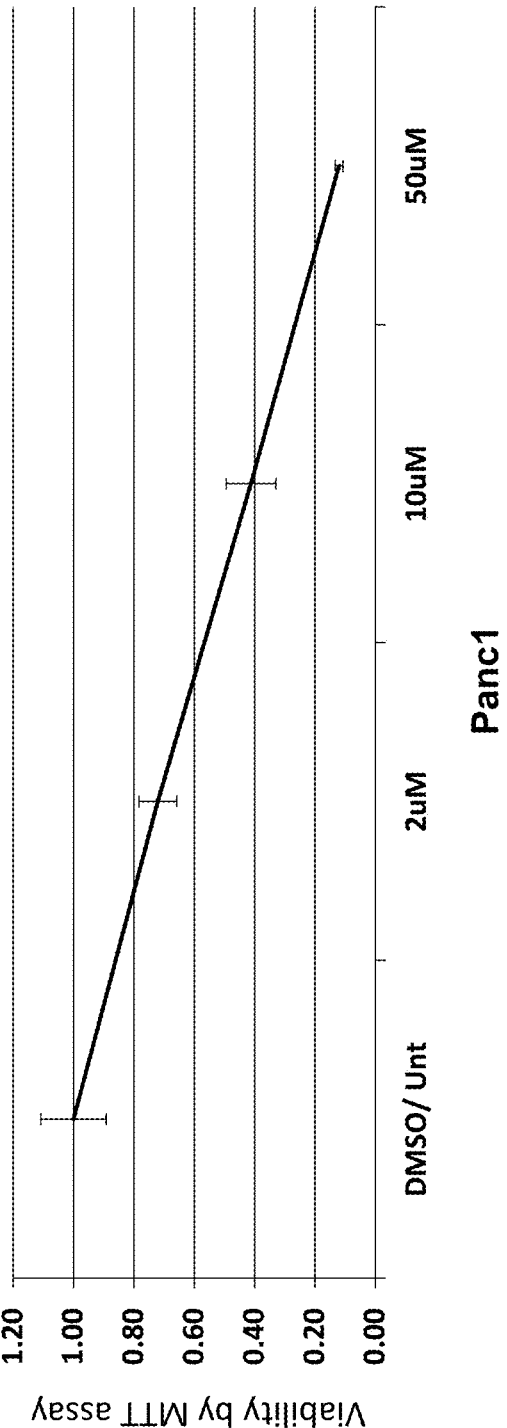
Figure 21C:
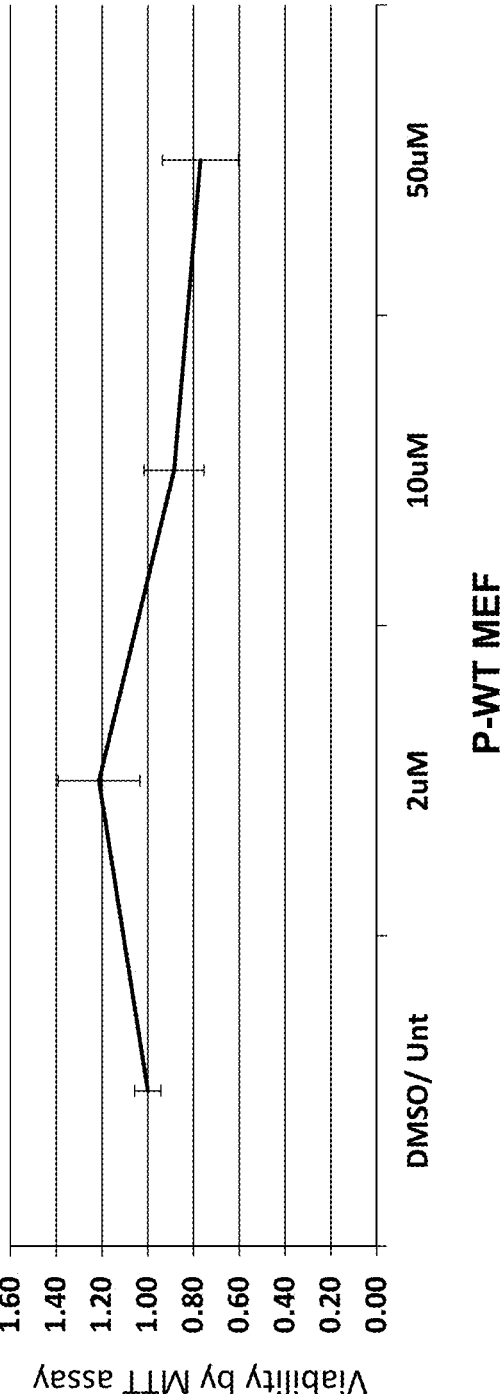
Figure 21D:
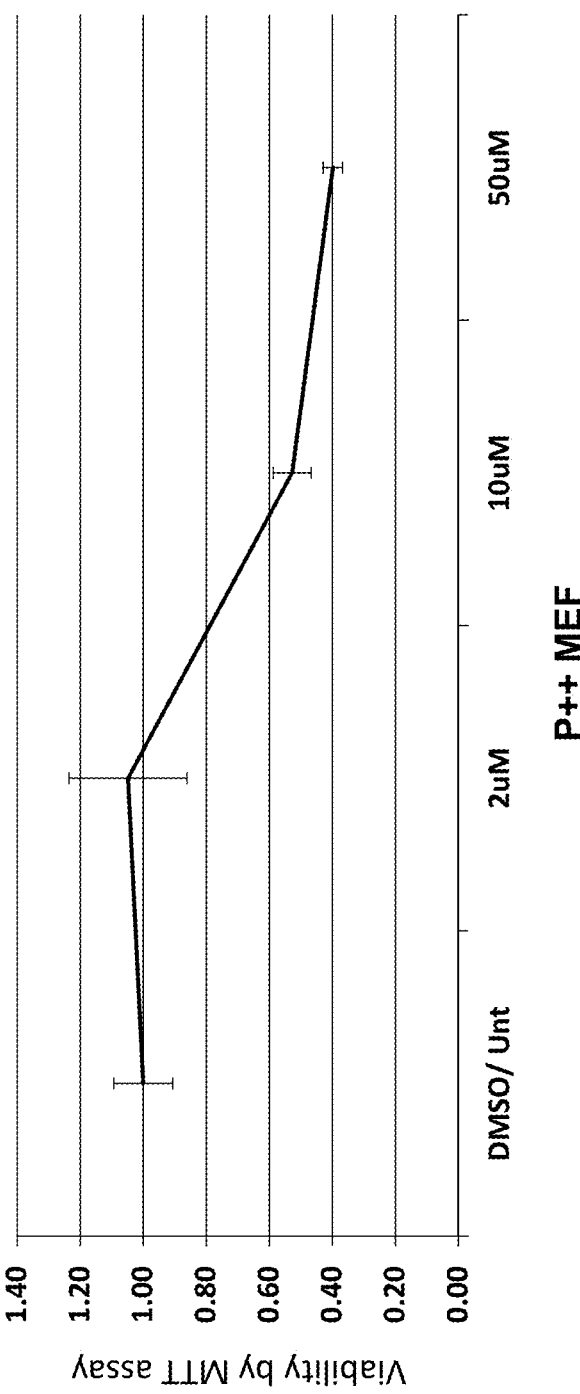
Figure 21E:
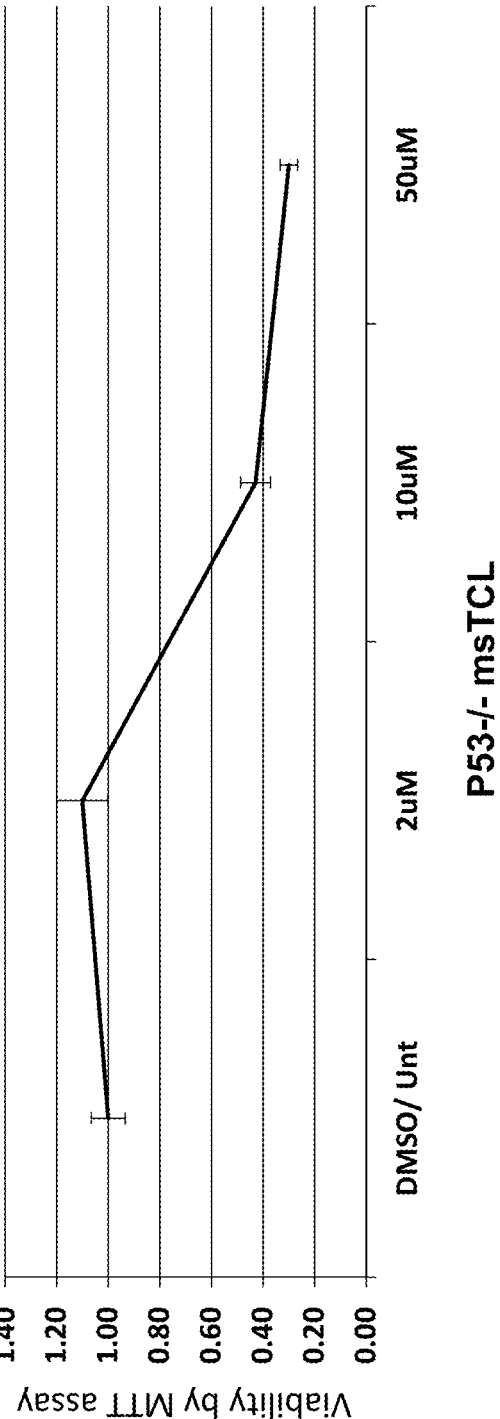
Figure 21F:
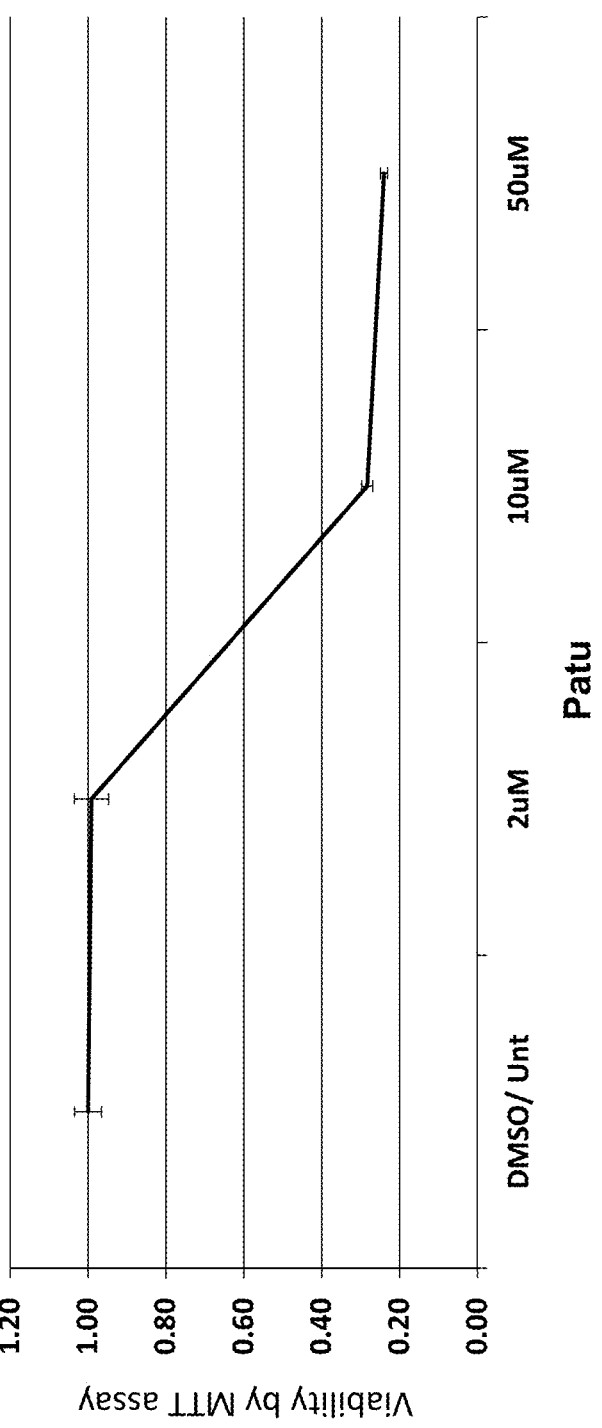
Figure 21G:
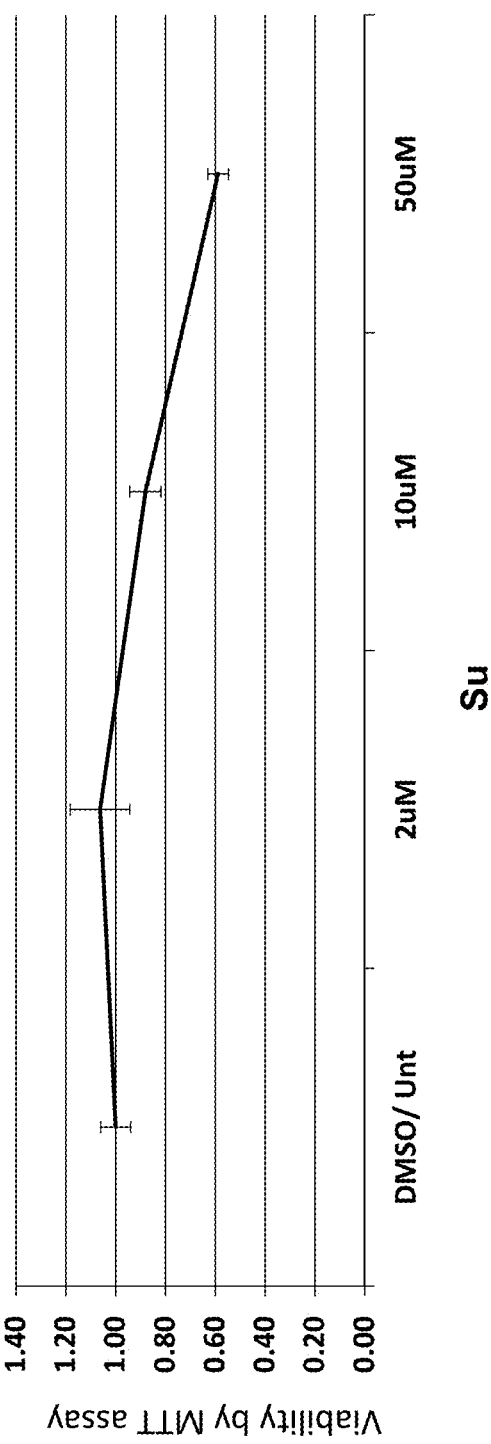
Figure 21H:
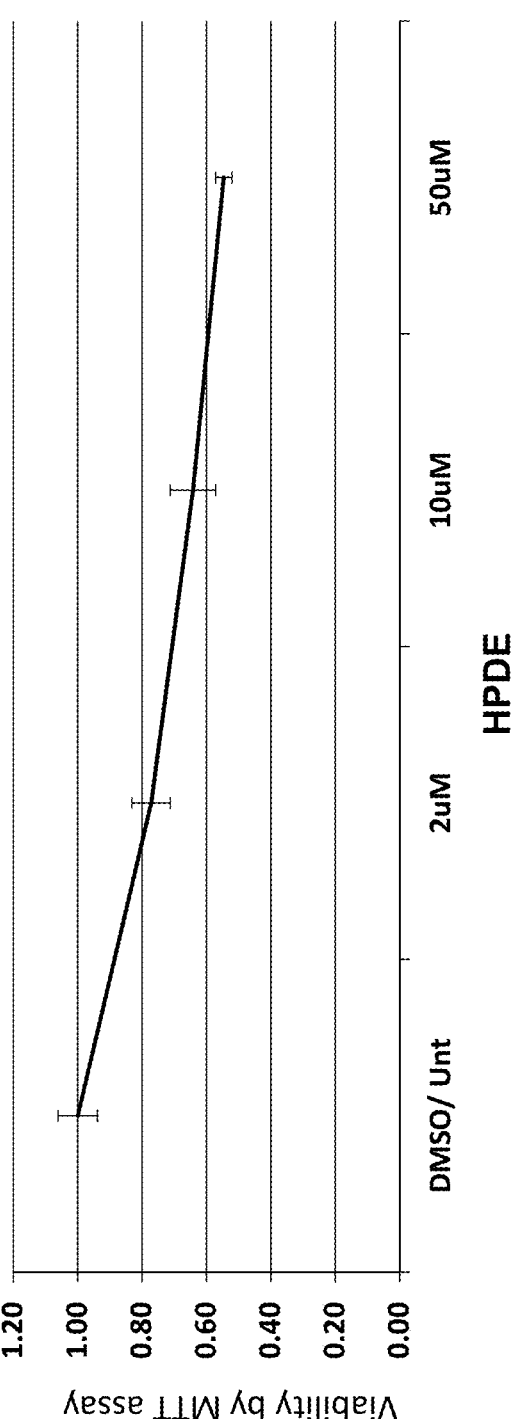

Additional dose response studies were conducted in the same cell lines using CP2; the results are plotted in FIGS. 21A-21I1 as follows: FIG. 21A, HeLa cervical cancer cells; FIG. 21B, Panc1 pancreatic cancer cells; FIG. 21C, P-WT: MEFs; control); FIG. 21D, P++: MEFs; FIG. 21E, p53–/– ms TCL; FIG. 21F, Patu pancreatic cancer cells; FIG. 21G, Su pancreatic cancer cells; FIG. 21I1, HPDE control.

Taken together, the data obtained in vivo in WT mice (HFD) and in vitro demonstrated that CP2 and related compounds can prevent the development of tumors and suppress the survival of multiple cancer cell lines.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a neurodegenerative disorder in a subject, wherein the neurodegenerative disorder is Alzheimer's disease (AD), and wherein the method comprises administering to the subject a therapeutically effective amount of a compound of Formula (I):

(I)

or a pharmaceutically acceptable salt thereof, wherein:
X is absent or selected from the group consisting of $CH_2$ and $C(O)$;
$R^1$ is selected from the group consisting of H, OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino;
$R^2$ is selected from the group consisting of H and $C_{1-6}$ alkyl;
$R^3$ is selected from the group consisting of H, $C_{1-6}$ alkyl, —C(O)($C_{1-3}$ alkyl), and —C(O)O($C_{1-3}$ alkyl);
$R^4$ is selected from the group consisting of $C_{3-10}$ cycloalkyl, $C_{6-10}$ aryl, 5-10 membered heteroaryl, and 5-10 membered heterocycloalkyl, each optionally substituted by 1, 2, 3, or 4 independently selected $R^5$ groups; and
$R^5$ is selected from the group consisting of OH, CN, $NO_2$, halo, $C_{1-3}$ alkyl, $C_{1-3}$ haloalkyl, $C_{1-3}$ alkoxy, $C_{1-3}$ haloalkoxy, $C_{3-7}$ cycloalkyl, amino, $C_{1-3}$ alkylamino, and di($C_{1-3}$ alkyl)amino.

2. The method of claim 1, wherein the subject is a human.

3. The method of claim 1, wherein the subject has a mutation in a PS1, PS2, or APP gene that is associated with AD.

4. The method of claim 1, wherein X is $CH_2$.

5. The method of claim 4, wherein $R^1$ is $C_{1-3}$ alkyl.

6. The method of claim 5, wherein $R^2$ is $C_{1-6}$ alkyl.

7. The method of claim 6, wherein $R^3$ is H.

8. The method of claim 7, wherein $R^4$ is unsubstituted 5-10 membered heteroaryl.

9. The method of claim 7, wherein $R^4$ is aryl and $R^5$ is halo or OH.

10. The method of claim 1, wherein the compound of Formula (I) is a compound of Formula (Ia):

(Ia)

or a pharmaceutically acceptable salt thereof.

11. The method of claim 1, wherein the compound of Formula (I) is a compound of Formula (II):

(II)

or a pharmaceutically acceptable salt thereof,
wherein:
$R^1$ is selected from the group consisting of H, OH, CN, $NO_2$, halo, $C_{1-3}$ alkyl, $C_{1-3}$ haloalkyl, $C_{1-3}$ alkoxy, C$_{1-3}$ haloalkoxy, C$_{3-7}$ cycloalkyl, amino, C$_{1-3}$ alkylamino, and di(C$_{1-3}$ alkyl)amino;

R$^2$ is selected from the group consisting of H and C$_{1-6}$ alkyl;

R$^3$ is selected from the group consisting of H, C$_{1-6}$ alkyl, —C(O)(C$_{1-3}$ alkyl), and —C(O)O(C$_{1-3}$ alkyl);

R$^4$ is selected from the group consisting of C$_{3-10}$ cycloalkyl, C$_{6-10}$ aryl, 5-10 membered heteroaryl, and 5-10 membered heterocycloalkyl, each optionally substituted by 1, 2, 3, or 4 independently selected R$^5$ groups; and R$^5$ is selected from the group consisting of OH, CN, NO$_2$, halo, C$_{1-3}$ alkyl, C$_{1-3}$ haloalkyl, C$_{1-3}$ alkoxy, C$_{1-3}$ haloalkoxy, C$_{3-7}$ cycloalkyl, amino, C$_{1-3}$ alkylamino, and di(C$_{1-3}$ alkyl)amino.

12. The method of claim 11, wherein R$^1$ is C$_{1-3}$ alkyl.

13. The method of claim 12, wherein R$^2$ is C$_{1-6}$ alkyl.

14. The method of claim 13, wherein R$^3$ is H.

15. The method of claim 14, wherein R$^4$ is unsubstituted 5-10 membered heteroaryl.

16. The method of claim 14, wherein R$^4$ is aryl and R$^5$ is halo or OH.

17. The method of claim 11, wherein the compound of Formula (II) is a compound of Formula (IIa)

(IIa)

or a pharmaceutically acceptable salt thereof.

18. The method of claim 1, wherein the compound of Formula (I) is selected from the group consisting of:

-continued

-continued

[chemical structure]

[chemical structure]

or a pharmaceutically acceptable salt thereof.

* * * * *